United States Patent
Langermann et al.

(10) Patent No.: US 9,790,277 B2
(45) Date of Patent: Oct. 17, 2017

(54) ANTI-H7CR ANTIBODIES

(71) Applicants: Amplimmune, Inc., Gaithersburg, MD (US); The Johns Hopkins University, Baltimore, MD (US)

(72) Inventors: Solomon Langermann, Baltimore, MD (US); Linda Liu, Clarksville, MD (US); Sheng Yao, Columbia, MD (US); Lieping Chen, Hamden, CT (US)

(73) Assignees: The Johns Hopkins University, Baltimore, MD (US); MedImmune, LLC, Gaithersburg, MD (US)

( * ) Notice: Subject to any disclaimer, the term of this patent is extended or adjusted under 35 U.S.C. 154(b) by 2 days.

(21) Appl. No.: 14/654,109

(22) PCT Filed: Dec. 23, 2013

(86) PCT No.: PCT/US2013/077586
§ 371 (c)(1),
(2) Date: Jun. 19, 2015

(87) PCT Pub. No.: WO2014/100823
PCT Pub. Date: Jun. 26, 2014

(65) Prior Publication Data
US 2016/0024210 A1  Jan. 28, 2016

Related U.S. Application Data

(60) Provisional application No. 61/745,296, filed on Dec. 21, 2012, provisional application No. 61/745,312, filed on Dec. 21, 2012, provisional application No. 61/827,279, filed on May 24, 2013, provisional application No. 61/827,269, filed on May 24, 2013.

(51) Int. Cl.
C07K 16/28 (2006.01)
A61K 39/395 (2006.01)
C12N 15/10 (2006.01)
G01N 33/574 (2006.01)

(52) U.S. Cl.
CPC ...... *C07K 16/2818* (2013.01); *C07K 16/2827* (2013.01); *C12N 15/1037* (2013.01); *G01N 33/57492* (2013.01); *C07K 2316/95* (2013.01); *C07K 2316/96* (2013.01); *C07K 2317/24* (2013.01); *C07K 2317/31* (2013.01); *C07K 2317/33* (2013.01); *C07K 2317/56* (2013.01); *C07K 2317/565* (2013.01); *C07K 2317/74* (2013.01); *C07K 2317/75* (2013.01); *C07K 2317/92* (2013.01); *C07K 2319/30* (2013.01); *G01N 2333/70521* (2013.01)

(58) Field of Classification Search
CPC ........................................ C07K 16/00–16/468
See application file for complete search history.

(56) References Cited

U.S. PATENT DOCUMENTS 8,840,889 B2 * 9/2014 Chen ................ C07K 14/70521
424/139.1
2016/0024211 A1 * 1/2016 Chen ................ C07K 14/70521
424/135.1

FOREIGN PATENT DOCUMENTS

WO      2011020024 A2     2/2011
WO    WO2011/020024 A2 *  2/2011

OTHER PUBLICATIONS

Patent Examination Report No. 1, issued in corresponding Australian Patent Application No. 2013363962, dated Nov. 19, 2015 (3 pages).

* cited by examiner

*Primary Examiner* — Jessica H Roark
(74) *Attorney, Agent, or Firm* — Melissa Hunter-Ensor; Leslie Serunian

(57) ABSTRACT

Antibodies and humanized variants thereof and their antigen-binding fragments and to other molecules that are capable of immunospecifically binding to the B7-H7 counter-receptor, H7CR, and their uses in enhancing immune responses and the treatment and diagnosis of cancer and other diseases are provided.

34 Claims, 26 Drawing Sheets

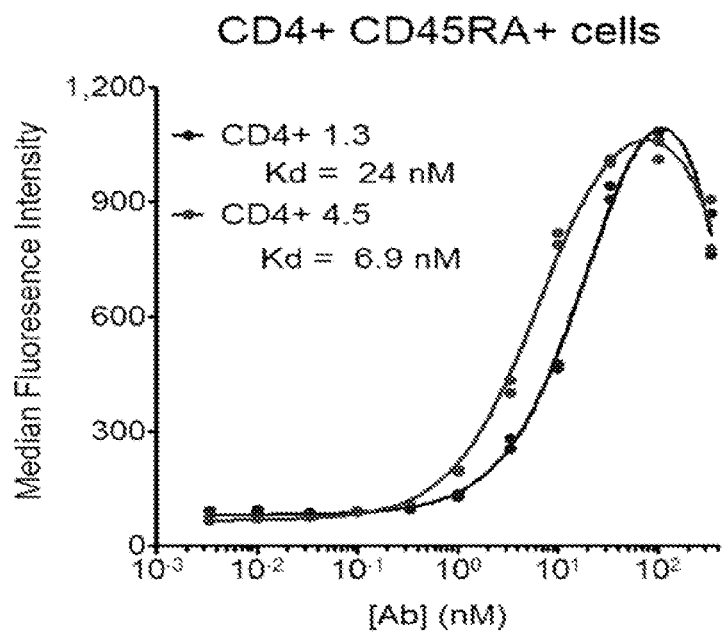
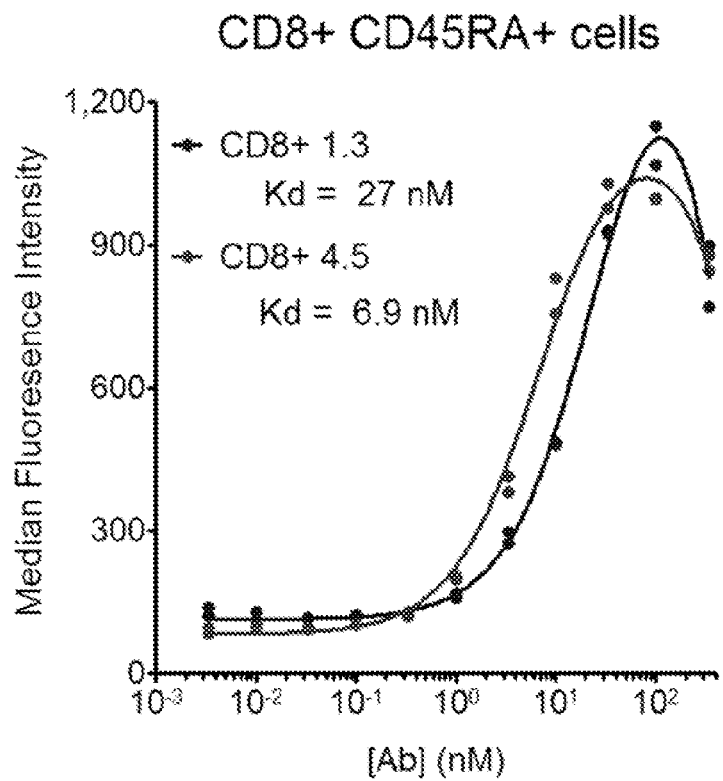
Figure 3

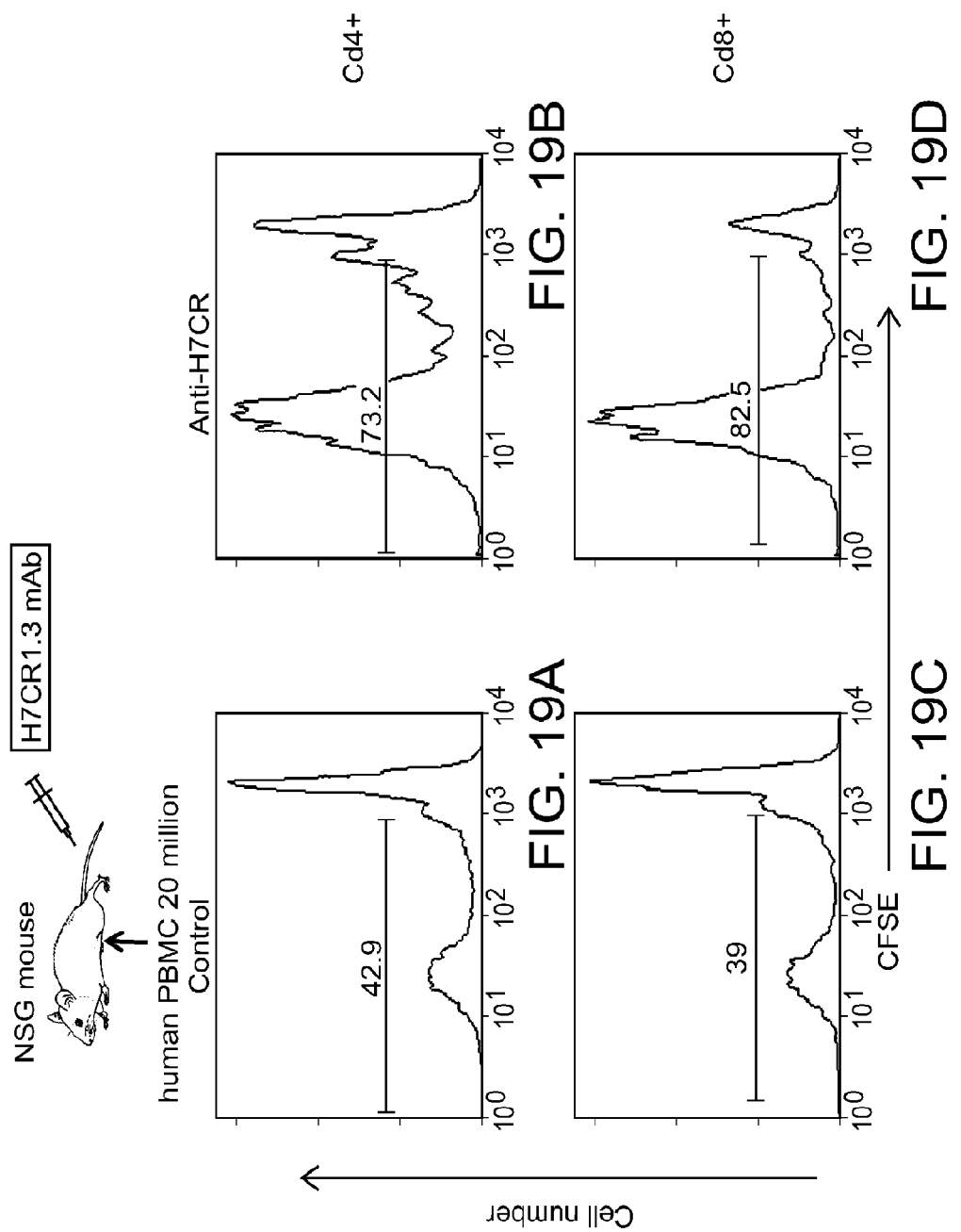

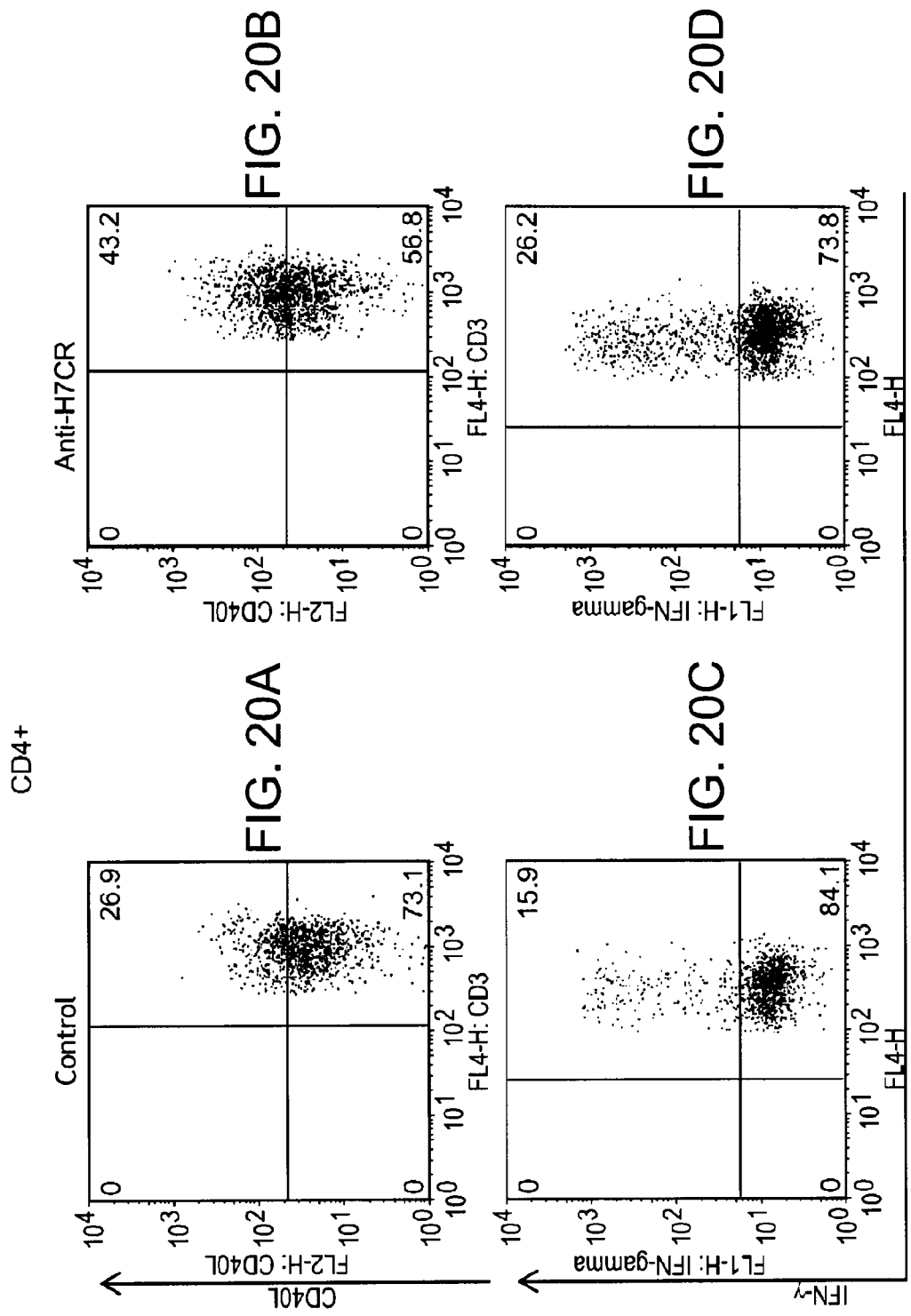

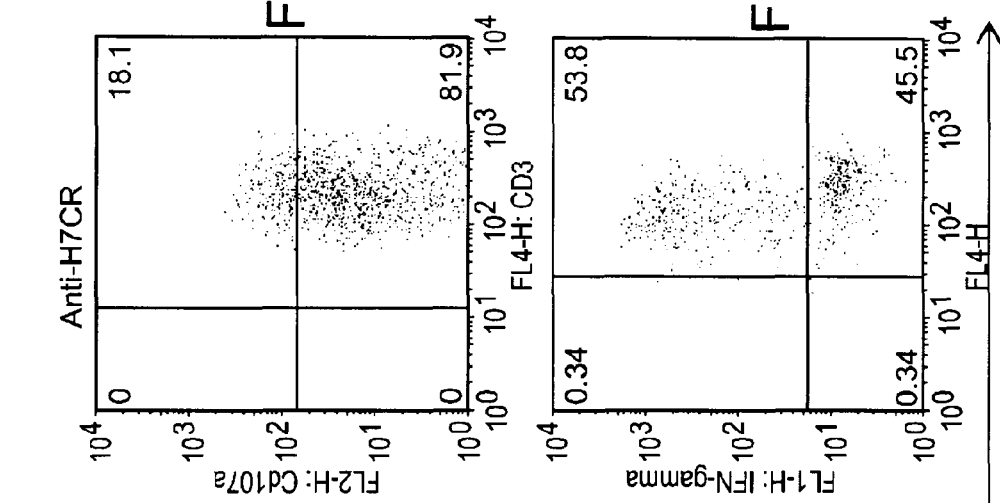
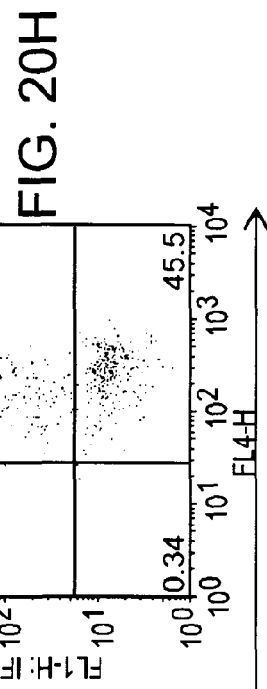
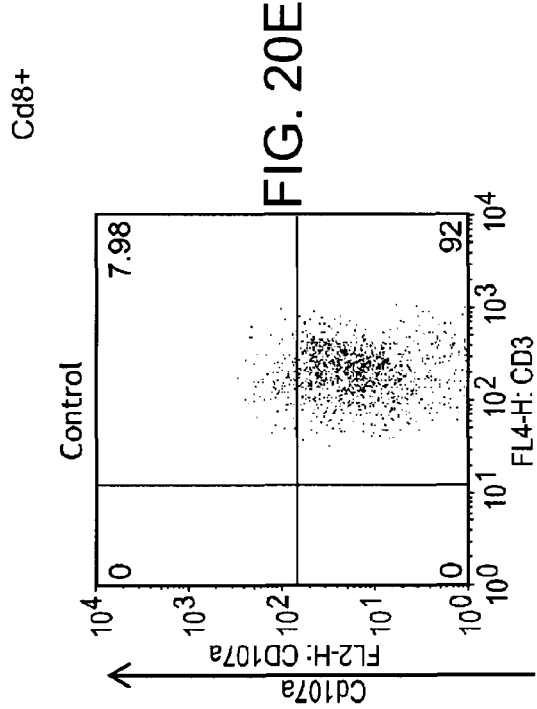
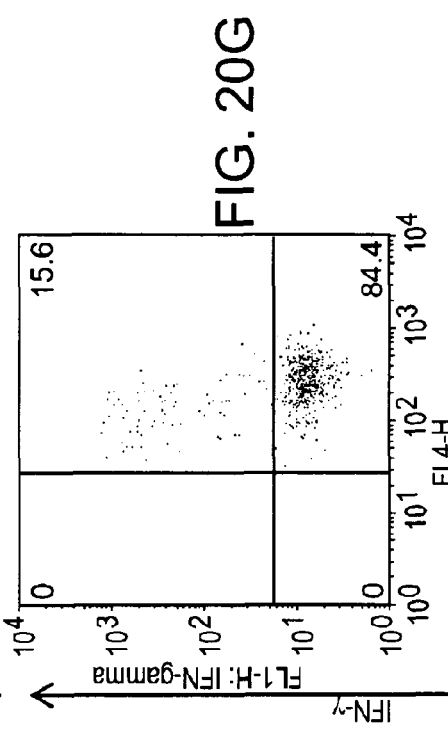

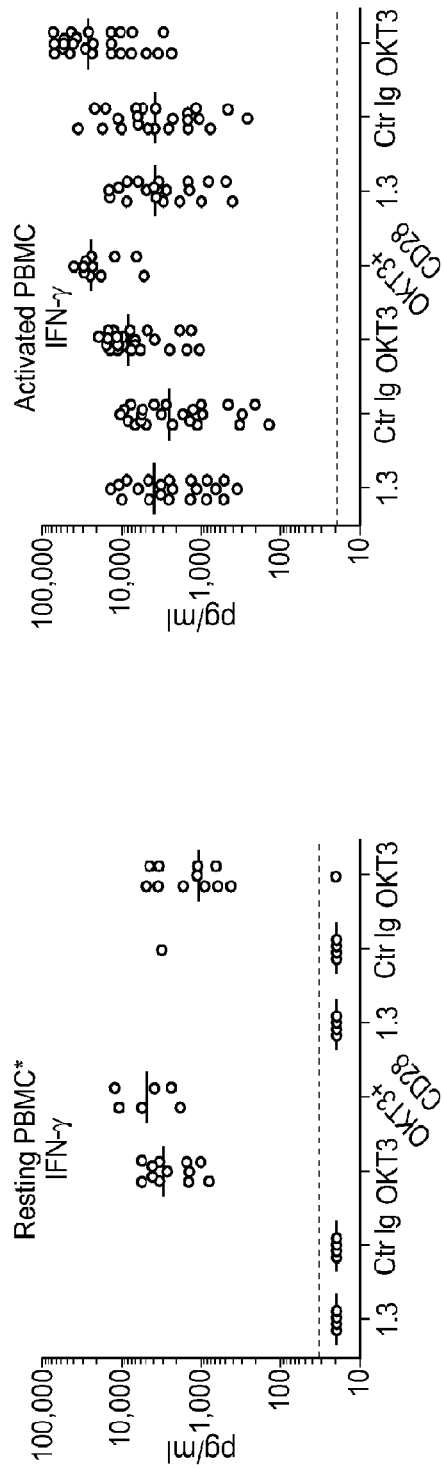
FIG. 21A
FIG. 21B
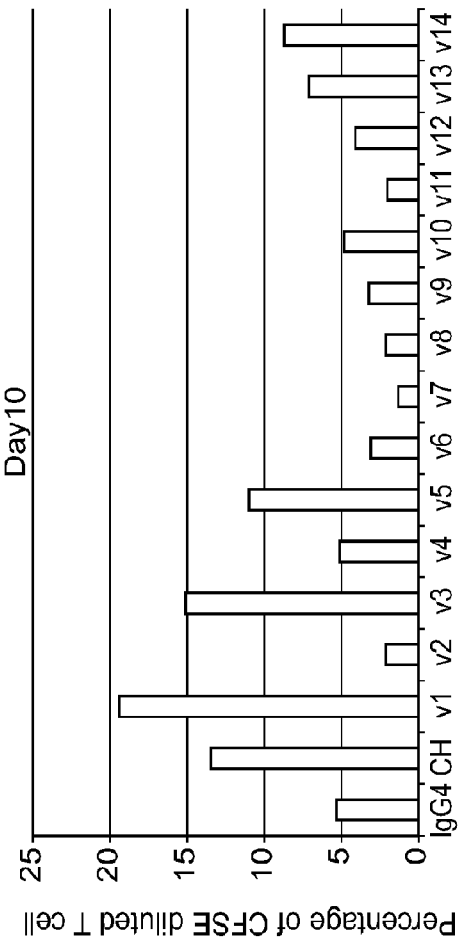
FIG. 22

ANTI-H7CR ANTIBODIES

CROSS-REFERENCE TO RELATED APPLICATIONS

This application is a 371 application of International Application No. PCT/US2013/077586, filed Dec. 19, 2013, which claims benefit of and priority to U.S. Provisional Patent Application No. 61/745,296 filed on Dec. 21, 2012, U.S. Provisional Patent Application No. 61/745,312 filed on Dec. 21, 2012, U.S. Provisional Patent Application No. 61/827,269 filed on May 24, 2013, and U.S. Provisional Patent Application No. 61/827,279 filed on May 24, 2013 all of which are incorporated by referenced in their entireties, where permissible.

STATEMENT REGARDING FEDERALLY SPONSORED RESEARCH OR DEVELOPMENT

This invention was made, in part, with United States Government support under award numbers R01 CA097085-10 and R01 A172592 from the National Institutes of Health (NIH), and U19 CA113341 from the National Cancer Institute (NCI). The United States Government may have certain rights in this invention.

REFERENCE TO SEQUENCE LISTING

This application incorporates the Sequence Listing contained in an ASCII text file named "315200.1103US1-00150.txt" submitted via EFS-Web. The text file was created on Oct. 5, 2015, and is 84.4 kb in size. This application includes one or more Sequence Listings pursuant to 37 C.F.R. 1.821 et seq., which are disclosed in both paper and computer-readable media, and which paper and computer-readable disclosures are herein incorporated by reference in their entirety.

BACKGROUND OF THE INVENTION

Field of the Invention

The present invention relates to antibodies and their antigen-binding fragments and to other molecules that are capable of immunospecifically binding to the B7-H7 counter-receptor, H7CR, and their uses in the treatment and diagnosis of cancer and other diseases.

Description of Related Art

The immune system of humans and other mammals is responsible for providing protection against infection and disease. Such protection is provided both by a humoral immune response and by a cell-mediated immune response. The humoral response results in the production of antibodies and other biomolecules that are capable of recognizing and neutralizing foreign targets (antigens). In contrast, the cell-mediated immune response involves the activation of macrophages, natural killer cells (NK), and antigen-specific cytotoxic T-lymphocytes by T cells, and the release of various cytokines in response to the recognition of an antigen (Dong, C. et al. (2003) "*Immune Regulation by Novel Costimulatory Molecules*," Immunolog. Res. 28(1): 39-48).

The ability of T cells to optimally mediate an immune response against an antigen requires two distinct signaling interactions (Viglietta, V. et al. (2007) "*Modulating Co-Stimulation*," Neurotherapeutics 4:666-675; Korman, A. J. et al. (2007) "*Checkpoint Blockade in Cancer Immunotherapy*," Adv. Immunol. 90:297-339). First, antigen that has been displayed on the surface of antigen-presenting cells (APC) must be presented to an antigen-specific naive CD4$^+$ T cell. Such presentation delivers a signal via the T cell receptor (TCR) that directs the T cell to initiate an immune response that will be specific to the presented antigen. Second, a series of co-stimulatory and inhibitory signals, mediated through interactions between the APC and distinct T cell surface molecules, triggers first the activation and proliferation of the T cells and ultimately their inhibition. Thus, the first signal confers specificity to the immune response; whereas, the second signal serves to determine the nature, magnitude and duration of the response.

The immune system is tightly controlled by co-stimulatory and co-inhibitory ligands and receptors. These molecules provide the second signal for T cell activation and provide a balanced network of positive and negative signals to maximize immune responses against infection while limiting immunity to self (Wang, L. et al. (Mar. 7, 2011) "*VISTA, A Novel Mouse Ig Superfamily Ligand That Negatively Regulates T Cell Responses*," J. Exp. Med. 10.1084/jem.20100619:1-16; Lepenies, B. et al. (2008) "*The Role Of Negative Costimulators During Parasitic Infections*," Endocrine, Metabolic & Immune Disorders—Drug Targets 8:279-288). Of particular importance is binding between the B7.1 (CD80) and B7.2 (CD86) ligands of the Antigen Presenting Cell and the CD28 and CLTA-4 receptors of the CD4$^+$ T-lymphocyte (Sharpe, A. H. et al. (2002) "*The B7-CD28 Superfamily*," Nature Rev. Immunol. 2:116-126; Dong, C. et al. (2003) "*Immune Regulation by Novel Costimulatory Molecules*," Immunolog. Res. 28(1):39-48; Lindley, P. S. et al. (2009) "*The Clinical Utility Of Inhibiting CD28-Mediated Costimulation*," Immunol. Rev. 229:307-321). Binding of B7.1 or of B7.2 to CD28 stimulates T cell activation; binding of B7.1 or B7.2 to CTLA4 inhibits such activation (Dong, C. et al. (2003) "*Immune Regulation by Novel Costimulatory Molecules*," Immunolog. Res. 28(1): 39-48; Lindley, P. S. et al. (2009) "*The Clinical Utility Of Inhibiting CD28-Mediated Costimulation*," Immunol. Rev. 229:307-321; Greenwald, R. J. et al. (2005) "*The B7 Family Revisited*," Ann. Rev. Immunol. 23:515-548). CD28 is constitutively expressed on the surface of T cells (Gross, J., et al. (1992) "*Identification And Distribution Of The Costimulatory Receptor CD28 In The Mouse*," J. Immunol. 149: 380-388), whereas CTLA4 expression is rapidly up-regulated following T-cell activation (Linsley, P. et al. (1996) "*Intracellular Trafficking Of CTLA4 And Focal Localization Towards Sites Of TCR Engagement*," Immunity 4:535-543). Since CTLA4 is the higher affinity receptor (Sharpe, A. H. et al. (2002) "*The B7-CD28 Superfamily*," Nature Rev. Immunol. 2:116-126), binding first initiates T cell proliferation (via CD28) and then inhibits it (via nascent expression of CTLA4), thereby dampening the effect when proliferation is no longer needed.

Further investigations into the ligands of the CD28 receptor have led to the identification and characterization of a set of related B7 molecules (the "B7 Superfamily") (Coyle, A. J. et al. (2001) "*The Expanding B7 Superfamily: Increasing Complexity In Costimulatory Signals Regulating T Cell Function*," Nature Immunol. 2(3):203-209; Sharpe, A. H. et al. (2002) "*The B7-CD28 Superfamily*," Nature Rev. Immunol. 2:116-126; Greenwald, R. J. et al. (2005) "*The B7 Family Revisited*," Ann. Rev. Immunol. 23:515-548; Collins, M. et al. (2005) "*The B7 Family Of Immune-Regulatory Ligands*," Genome Biol. 6:223.1-223.7; Loke, P. et al. (2004) "*Emerging Mechanisms Of Immune Regulation: The Extended B7 Family And Regulatory T Cells*." Arthritis Res. Ther. 6:208-214; Korman, A. J. et al. (2007) "*Checkpoint*

Blockade in Cancer Immunotherapy," Adv. Immunol. 90:297-339; Flies, D. B. et al. (2007) *"The New B7s: Playing a Pivotal Role in Tumor Immunity,"* J. Immunother. 30(3): 251-260; Agarwal, A. et al. (2008) *"The Role Of Positive Costimulatory Molecules In Transplantation And Tolerance,"* Curr. Opin. Organ Transplant. 13:366-372; Lenschow, D. J. et al. (1996) *"CD28/B7 System of T Cell Costimulation,"* Ann. Rev. Immunol. 14:233-258; Wang, S. et al. (2004) *"Co-Signaling Molecules Of The B7-CD28 Family In Positive And Negative Regulation Of T Lymphocyte Responses,"* Microbes Infect. 6:759-766). There are currently eight known members of the family: B7.1 (CD80), B7.2 (CD86), the inducible co-stimulator ligand (ICOS-L), the programmed death-1 ligand (PD-L1; B7-H1), the programmed death-2 ligand (PD-L2; B7-DC), B7-H3, B7-H4 (also referred to as B7x and B7S1; Sica, G. L. et al. (2003) *"B7-4, A Molecule Of The B7 Family, Negatively Regulates T Cell Immunity,"* Immunity 18:849-861; Zang, X. et al. (2003) B7x: *A Widely Expressed B7 Family Member That Inhibits T Cell Activation,"* Proc. Natl. Acad. Sci. (USA) 100:10388-10392; Prasad, D. V. et al. (2003) B7S1, *A Novel B7 Family Member That Negatively Regulates T Cell Activation,"* Immunity 18:863-873), B7-H6 (Collins, M. et al. (2005) *"The B7 Family Of Immune-Regulatory Ligands,"* Genome Biol. 6:223.1-223.7) and B7-H7 (Flajnik, M. F. et al. (2012) *"Evolution Of The B7 Family: Co-Evolution Of B7H6 And Nkp30, Identification Of A New B7 Family Member, B7H7, And Of B7's Historical Relationship With The MHC,"* Immunogenetics 64:571-590). The B7 family of genes is essential in the regulation of the adaptive immune system. Most B7 family members contain both variable (V)- and constant (C)-type domains of the immunoglobulin superfamily (IgSF).

B7 ligands are expressed on the cell surface of many different cell types including antigen presenting cells (APCs) and their interaction with receptor molecules on T cells provide activating and/or inhibitory signals that regulate T cell activation and tolerance (Collins, M. et al. (2005) *"The B7 Family Of Immune-Regulatory Ligands,"* Genome Biol. 6:223.1-223.7). Some inhibitory B7 ligands are also expressed on tumor cells, resulting in suppression of immune responses (Keir, M. E. et al. (2008) *"PD-1 And Its Ligands In Tolerance And Immunity,"* Annu. Rev. Immunol. 26:677-704; Zou, W. et al. (2008) *"Inhibitory B7-Family Molecules In The Tumour Microenvironment,"* Nat. Rev. Immunol. 8:467-477). Therefore, stimulating or attenuating the interactions of B7 ligands and their receptors holds therapeutic potential for autoimmune diseases and cancer (WO 2011/020024; Flajnik, M. F. et al. (2012) *"Evolution Of The B7 Family: Co-Evolution Of B7H6 And Nkp30, Identification Of A New B7 Family Member, B7H7, And Of B7's Historical Relationship With The MHC,"* Immunogenetics 64:571-590).

Despite all prior advances in the treatment of inflammation and cancer, a need remains for compositions capable of providing enhanced immunotherapy for the treatment of such conditions.

It is an object of the invention to provide compositions capable of providing enhanced immunotherapy for the treatment of cancer, infectious disease, inflammation and other diseases and conditions.

SUMMARY OF THE INVENTION

Antibodies and their antigen-binding fragments and other molecules that are capable of immunospecifically binding to the B7-H7 counter-receptor, H7CR, are provided. The B7-H7 counter-receptor is also known as B7-H7CR and CD28H (Yhu, et al., Nature Communications, 4:1-12 (2013)). Methods of their use in the treatment and diagnosis of cancer, infectious disease, inflammation and other diseases and conditions are also provided. The H7CR binding molecules can be a monoclonal antibody, a human antibody, a chimeric antibody or a humanized antibody.

One embodiment provides H7CR binding molecules wherein the antigen-binding fragment includes six CDRs, wherein the CDRs include at least one CDR of the CDRs of anti-H7CR antibodies: 1.3, 4.5 and 7.8, or a consensus CDR thereof, with all remaining CDRs selected from:
  (A) the three light chain and the three heavy chain CDRs of anti-H7CR antibody 1.3;
  (B) the three light chain and the three heavy chain CDRs of anti-H7CR antibody 4.5; or
  (C) the three light chain and the three heavy chain CDRs of anti-H7CR antibody 7.8.

Another embodiment provides H7CR binding molecules wherein the six CDRs are:
  (A) the three light chain and the three heavy chain CDRs of anti-H7CR antibody 1.3;
  (B) the three light chain and the three heavy chain CDRs of anti-H7CR antibody 4.5; or
  (C) the three light chain and the three heavy chain CDRs of anti-H7CR antibody 7.8.

Still another embodiment provides H7CR binding molecules having an antigen-binding fragment of a humanized variant of anti-human H7CR antibody 1.3 or 4.5, wherein the molecule immunospecifically binds to human H7CR, and wherein the antigen-binding fragment include:
  (A) (1) a light chain variable region of a humanized variant of anti-human H7CR antibody 1.3, wherein said light chain variable region has the amino acid sequence of any of SEQ ID NO:17-22; and
  (2) a heavy chain variable region of a humanized variant of anti-human H7CR antibody 1.3, wherein said heavy chain variable region has the amino acid sequence of any of SEQ ID NO:23-28;
or
  (B) (1) a light chain variable region of a humanized variant of anti-human H7CR antibody 4.5, wherein said light chain variable region has the amino acid sequence of any of SEQ ID NO:33-38; and
  (2) a heavy chain variable region of a humanized variant of anti-human H7CR antibody 4.5, wherein said heavy chain variable region has the amino acid sequence of any of SEQ ID NO:39-44.

A preferred embodiment concerns the embodiment wherein said H7CR binding molecule immunospecifically binds to H7CR that is:
  (A) arrayed on the surface of a live cell; or
  (B) expressed at an endogenous concentration.

In one embodiment the live cell is a T cell, an NK cell, or a plasmacytoid dendritic cell.

In still another embodiment the molecule is substantially incapable of blocking H7CR's interaction with B7-H7.

In another embodiment the molecule is capable of binding H7CR and agonizing H7CR activity.

Any of the antibodies can be a bispecific, trispecific or multispecific antibody. The molecule can be detectably labeled or includes a conjugated toxin, drug, receptor, enzyme, receptor ligand, or a combination thereof.

Another embodiment provides a pharmaceutical composition containing a therapeutically effective amount of any of the above-referenced molecules, and a physiologically acceptable carrier or excipient.

The disclosed compositions can be used to treat a disease in a subject exhibiting a symptom of the disease by administering to the subject, a therapeutically effective amount of any of the above-referenced pharmaceutical compositions to activate the B7-H7 pathway and stimulate an immune response. Specific indications to be treated include, but are not limited cancer, an infectious disease, a chronic viral disease, an inflammatory condition, or an autoimmune disease.

A method for treating a disease wherein the pharmaceutical composition agonizes an H7CR function is also provided.

Methods for prophylactically treating a disease include administering to a subject in advance of exhibiting a symptom of the disease a prophylactically effective amount of any of the above-referenced pharmaceutical compositions.

Methods for diagnosing a disease (especially cancer or a disease affecting T cell number and health) in a subject include assaying cells of the subject for their ability to bind to any of the above-referenced H7CR binding molecule, wherein the method provides a cytologic assay for diagnosing the immune responsiveness or the presence of the disease in the subject.

BRIEF DESCRIPTION OF THE DRAWINGS

FIGS. 3A and 3B are line graphs of Median Fluorescence Intensity versus log [Ab] (nM) showing H7CR mAb binding curves to human naïve (CD45RA+) CD4 and CD8 T cells from PBMC (FIG. 3B).

FIGS. 8A, 8C, 8E, and 8G are scatter plots of log fluorescence using antibody 1.3 versus log fluorescence using anti-CD3 antibody. FIGS. 8B, 8D, 8F, and 8H are scatter plots of log fluorescence using anti-B7H7 antibody 2D3 versus anti-CD14 antibody. All donors show expression of H7CR on CD3 T cell with minimal expression of B7-H7 in PBMC.

FIGS. 9A, 9C, 9E, and 9G are scatter plots of fluorescence using antibody 1.3 versus anti-CD3 antibody. FIGS. 9B, 9D, 9F, and 9H are scatter plots of fluorescence using anti-B7H7 antibody 2D3 versus anti-CD14 antibody. Donors 2, 3, 4 show expression of H7CR on CD3 T cell with minimal expression of B7-H7 in PBMC. Donor 1 shows high expression level of B7-H7 on CD14+ monocyte and low H7CR expression level on CD3 T cells.

FIGS. 10A-10AD are flow cytometry histograms showing the expression of H7CR and B7-H7 by human monocytes (10A, 10F, 10K, 10P. 10U, and 10Z), CD8+CD3+ lymphocytes (10B, 10G, 10L, 10Q, 10V, 10AA), CD8− CD3+ lymphocytes (10C, 10H, 10M, 10R, 10W, and 10AB), CD16+NK cells (10D, 10I, 10N, 10S, 10X, and 10AC), and CD3−CD8− cells (10E, 10J, 10O, 10T, 10Y, and 10AD). Antibody 18C3 (10A-10E) and antibody 2D3 (10F-10J) are anti-B7-H7 monoclonal antibodies. FIGS. 10K-10O use anti PD-1 antibody. FIGS. 10P-10T use antibody 1.3. FIGS. 10U-10Y use antibody 4.5. FIGS. 10Z-10AD use antibody 7.8.

FIGS. 11A-11AD are flow cytometry histograms showing the expression of H7CR and B7-H7 by cynomolgus monkey monocytes (11A, 11F, 11K, 11P, 11U, and 11Z), CD8+CD3+ lymphocytes (11B, 11G, 11L, 11Q, 11V, 11AA), CD8− CD3+ lymphocytes (11C, 11H, 11M, 11R, 11W, and 11AB), CD16+NK cells (11D, 11I, 11N, 11S, 11X, and 11AC), and CD3−CD8-cells (11E, 11J, 11O, 11T, 11Y, and 11AD). Antibody 18C3 (FIGS. 11A-11E) and antibody 2D3 (FIGS. 11F-11J) are anti-B7-H7 monoclonal antibodies. FIGS. 11K-11O use anti PD-1 antibody. FIGS. 11P-11T use antibody 1.3. FIGS. 11U-11Y use antibody 4.5. FIGS. 11Z-11AD use antibody 7.8.

FIG. 12A is a histogram of Counts versus log Comp-FITC-A using anti-HLA-ABC antibody. FIG. 12B is a histogram of Counts versus log Comp-PE-A using anti-B7-H1 antibody. FIG. 12C is a histogram of Counts versus log Comp-PerCP-Cy5-5-A using anti-HLA-DR antibody. FIG. 12D is a histogram of Counts versus log Comp-PE-Cy7-A using anti-CD40 antibody. FIG. 12E is a histogram of Counts versus log Comp-APC-A using anti-CD86 antibody. FIG. 12F is a histogram of Counts versus log Comp-PacificBlue-A using anti-CD83 antibody. FIG. 12G is a histogram of Counts versus log Comp-FITC-A using anti-CD80 antibody. FIG. 12H is a histogram of Counts versus log Comp-PE-A using anti-B7-DC antibody. FIG. 12I is a histogram of Counts versus log Comp-PacificBlue-A using anti-CD54 antibody. FIG. 12J is a histogram of Counts versus log Comp-PerCP-Cy5-5A using anti-B7-H7 antibody. FIG. 12K is a histogram of Counts versus log Comp-APC-A using anti-CCR7 antibody. Solid grey line represents isotype control. Dashed line represents immature dendritic cells. Dotted line represents cells treated with TNFα and PGE2 for one day. Solid black line represents cells treated with 1 ng/ml TNFa and 1 µg/ml PGE2 for two days.

FIG. 14A is a bar graph of IFN-γ-expressing (pg/nl) cells treated with CtlIg, H7CR1.3, H7CR4.5, H7CR7.8 or T cell only. FIG. 14B is a bar graph of IL-5-expressing (pg/nl) cells treated with CtlIg, H7CR1.3, H7CR4.5, H7CR7.8 or T cell only. FIG. 14C is a bar graph of TNF-α-expressing (pg/nl) cells treated with CtlIg, H7CR1.3, H7CR4.5, H7CR7.8 or T cell only. FIG. 14D is a bar graph of IL-13-expressing (pg/nl) cells treated with CtlIg, H7CR1.3, H7CR4.5, H7CR7.8 or T cell only. FIG. 14E is a bar graph of GM-CSF-expressing (pg/nl) cells treated with CtlIg, H7CR1.3, H7CR4.5, H7CR7.8 or T cell only. FIG. 14F is a bar graph of IL-10-expressing (pg/nl) cells treated with CtlIg, H7CR1.3, H7CR4.5, H7CR7.8 or T cell only. FIG. 14G is a bar graph of IL-6-expressing (pg/nl) cells treated with CtlIg, H7CR1.3, H7CR4.5, H7CR7.8 or T cell only. FIG. 14H is a bar graph of IL-12p70-expressing (pg/nl) cells treated with CtlIg, H7CR1.3, H7CR4.5, H7CR7.8 or T cell only. FIG. 14I is a bar graph of MCP-1-expressing (pg/nl) cells treated with CtlIg, H7CR1.3, H7CR4.5, H7CR7.8 or T cell only. FIG. 14J is a bar graph of IL-17-expressing (pg/nl) cells treated with CtlIg, H7CR1.3, H7CR4.5, H7CR7.8 or T cell only. FIG. 14AK is a bar graph of MIP-1β-expressing (pg/nl) cells treated with CtlIg, H7CR1.3, H7CR4.5, H7CR7.8 or T cell only. FIG. 14L is a bar graph of IL-8-expressing (pg/nl) cells treated with CtlIg, H7CR1.3, H7CR4.5, H7CR7.8 or T cell only.

FIG. 15A is a scatter plot of log Comp-PerCP-Cy5-5-A::IFNg versus Comp-FITC::CFSE using CtlIg. FIG. 15B is a scatter plot of log Comp-PerCP-Cy5-5-A::IFNg versus Comp-FITC::CFSE.

FIG. 16A is a bar graph of Divided CD4+ T Cells (%) that shows anti-CD28H antibodies (solid box) mediate a strongly augmented T cell proliferation in the absence of CTLA4-Ig. FIG. 16B shows that anti-CD28H antibodies (solid box) mediate an increase in cytokine expression. FIG. 16B includes panel A which is a bar graph of pg/ml of IFN-γ from T cells treated with control (open box) or anti-CD28H (solid box). Panel B is a bar graph of pg/ml the following cytokines (solid box) from left to right: IL-5, IL-10, TNF-α, IL-17. Control (open box).

FIGS. 19A-D are flow cytometry histograms of Cell Number versus CFSE showing that antibody 1.3 expands human CD4+ and CD8+ cells in vivo. FIGS. 19A and 19C are controls showing Cell number versus log fluorescence of a control antibody. FIG. 19B shows CD4+ Cell number versus log fluorescence using anti-H7CR antibody 1.3. FIG. 19D shows CD8+ Cell number versus log fluorescence using anti-H7CR antibody 1.3. Hamster IgG isotype control (Biolegend) was used as control antibody.

FIGS. 20A-H are flow cytometry scatter plots showing an increase in cells expressing of CD40L, IFNγ and CD107a in an NGS mouse injected with antibody 1.3. FIG. 20A shows log anti-CD40L antibody fluorescence versus log anti-CD3 antibody fluorescence of untreated CD4+ cells. FIG. 20B shows log fluorescence of anti-CD40L antibody fluorescence versus log anti-CD3 antibody fluorescence of CD4+ cells treated with anti-H7CR antibody 1.3. FIG. 20C shows log fluorescence of anti-IFNγ antibody versus log fluorescence of anti-CD3 antibody in untreated CD4+ cells. FIG. 20D show log fluorescence of IFNγ antibody versus log fluorescence of H in CD4+ cells treated with anti-H7CR antibody. FIG. 20E shows log anti-CD107a antibody fluorescence versus log anti-CD3 antibody fluorescence of untreated CD8+ cells. FIG. 20F shows log fluorescence of anti-CD107a antibody fluorescence versus log anti-CD3 antibody fluorescence of CD8+ cells treated with anti-H7CR antibody 1.3. FIG. 20G shows log fluorescence of anti-IFN' antibody versus log fluorescence of anti-CD3 antibody in untreated CD8+ cells. FIG. 20H show log fluorescence of IFN' antibody versus log fluorescence of H in CD8+ cells treated with anti-H7CR antibody.

FIG. 21A is a dot plot of IFN-γ (pg/mL) in resting human PMBCs stimulated with (from left to right) chimeric murine antiH7CR antibody (1.3), negative control (Ctl Ig), OKT3, OKT3+CD28, chimeric murine antiH7CR antibody (1.3)-immobilized, negative control immobilized, and OKT3—immobilized. FIG. 22B is a dot plot of IFN-γ in activated PMBCs stimulated with (from left to right) chimeric murine antiH7CR antibody (1.3), negative control (Ctl Ig), OKT3, OKT3+CD28, chimeric murine antiH7CR antibody (1.3)-immobilized, negative control immobilized, and OKT3—immobilized. FIG. 21B is a dot plot of IFN-γ in activated PMBCs stimulated with (from left to right) chimeric murine antiH7CR antibody (1.3), negative control (Ctl Ig), OKT3, OKT3+CD28, chimeric murine antiH7CR antibody (1.3)-immobilized, negative control (Ctl-Ig) immobilized, and OKT3—immobilized at 10 µg/ml concentration overnight.

FIG. 22 is a bar graph of Percentage of CFSE diluted T Cell for monocyte-derived dendritic cells matured by 1 ng/ml TNFα and 1 µg/ml PGE2 for two days. The dendritic cells were incubated with CFSE-labeled autologous T cells for two weeks with 100 ng/ml tetanus toxoid. Cells were treated with (from left to right) 10 µg/ml soluble Control IgG4, chimeric murine antiH7CR antibody (1.3), and variants V1-V14 (see Table 10).

DETAILED DESCRIPTION OF THE INVENTION

Antibodies, humanized variants of antibodies and their antigen-binding fragments thereof and to other molecules that are capable of immunospecifically binding to the B7-H7 counter-receptor, H7CR (also known as B7-H7CR and CD28H) and their uses in the treatment and diagnosis of cancer and other diseases are provided.

Figure 1:
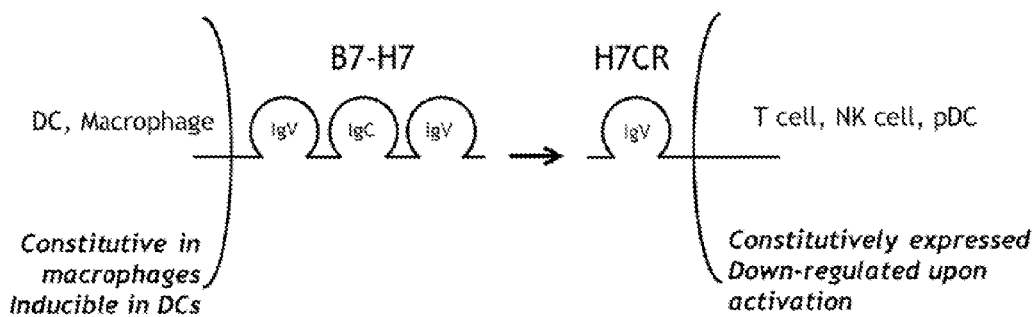
FIG. 1 is a diagram of the structure, the expression pattern and the interaction between H7CR and B7-H7 on separate cells.

B7-H7 is expressed on antigen presenting cells; it is constitutively expressed on macrophages and inducible on dendritic cells. B7-H7 interacts with a counter-receptor (H7CR) to stimulate the immune system and immune responses (FIG. 1). H7CR is particularly expressed on naïve T cells, NK cells, and plasmacytoid dendritic cells (especially in the spleen, lymph node and thymus), and its expression is down-regulated on matured or activated cells. Such down-regulation of H7CR impairs activated/memory T cell survival in vivo, and leads to a return to immune system quiescence in normal individuals. Thus, the interaction between B7-H7 and H7CR is important for native T cell priming and activated/memory T cell survival in vivo. However, H7CR is also seen to be down-regulated in chronically antigen-exposed/exhausted T cells. Molecules, such as B7-H7 Ig and anti-H7CR antibodies, that are capable of binding to H7CR are capable of serving as agonists of T cell proliferation and cytokine production. Such molecules have utility in the treatment of cancer, infectious disease and diseases characterized by an inadequate T cell response. Conversely, molecules, such as anti-B7-H7 antibodies and H7CR Ig, that are capable of blocking the interaction between B7-H7 and H7CR serve as antagonists of T cell proliferation and cytokine production. Such molecules have utility in the treatment of inflammation and in particular, autoimmune disease.

A. B7-H7

B7-H7 was discovered through a search of *Xenopus* databases as a gene that exhibited significant homology to *Xenopus* B7-H4. The B7-H4 protein possesses 282 amino acid residues, which have been categorized as having an amino terminal extracellular domain, a large hydrophobic transmembrane domain and a very short intracellular domain (consisting of only 2 amino acid residues). Like other B7 family members, B7-H4 possesses a pair of Ig-like regions in its extracellular domain. The B7-H4 protein has an overall structure of a type I transmembrane protein.

The B7-H7 amino acid sequence was found to be similar to a previously discovered human gene, HHLA2 (human endogenous retrovirus-H long terminal repeat-associating protein 2 (HHLA2); Mager, D. L. et al. (1999) "*Endogenous Retroviruses Provide The Primary Polyadenylation Signal For Two New Human Genes (HHLA2 And HHLA3*)," Genomics 59:255-263), that had no known function (Flajnik, M. F. et al. (2012) "*Evolution Of The B7 Family: Co-Evolution Of B7H6 And Nkp30, Identification Of A New B7 Family Member, B7H7, And Of B7's Historical Relationship With The MHC*," Immunogenetics 64:571-590).

The human B7-H7 sequence has been found to have homologs in chicken, opossum, hoofed mammals (e.g., horse, pig), salmon, and shark. However, only pseudogenes have been thus far identified in rodents (mouse and rat). The amino acid sequences of such genes reveal a similar domain structures in all species, with conservation of the canonical residues for Ig superfamily domains.

Human B7-H7 polypeptide is 414 amino acids in length and has been reported to contain the following: a signal sequence, an extracellular domain, 3 immunoglobulin-like (Ig-like) domains, a transmembrane domain, and a cytoplasmic domain. In particular, the human B7-H7 polypeptide has been reported to contain an Ig-like V-type 1 domain, an Ig-like C-1 type domain, and an Ig-like V-type 2 domain. Multiple naturally occurring variants of B7-H7 exist (e.g., Accession No. Q9UM44-1 (*homo sapiens*), NP_009003 (GI:5901964, *homo sapiens*), and AAD48396 (GI: 15726285, *homo sapiens*); see WO 2011/020024).

The term "native-B7-H7" refers to any naturally occurring B7-H7 amino acid sequence, including immature or precursor and mature forms. Mature forms of B7-H7 include B7-H7 proteins that have been post-translationally modified, for example B7-H7 polypeptides that have had a signal or leader amino acid sequence cleaved. The amino acid sequence of a representative human B7-H7, Accession No. Q9UM44-1, is (SEQ ID NO:1):

```
MKAQTALSFF LILITSLSGS QGIFPLAFFI YVPMNEQIVI

GRLDEDIILP SSFERGSEVV IHWKYQDSYK VHSYYKGSDH

LESQDPRYAN RTSLFYNEIQ NGNASLFFRR VSLLDEGIYT

CYVGTAIQVI TNKVVLKVGV FLTPVMKYEK RNTNSFLICS

VLSVYPRPII TWKMDNTPIS ENNMEETGSL DSFSINSPLN

ITGSNSSYEC TIENSLLKQT WTGRWTMKDG LHKMQSEHVS

LSCQPVNDYF SPNQDFKVTW SRMKSGTFSV LAYYLSSSQN

TIINESRFSW NKELINQSDF SMNLMDLNLS DSGEYLCNIS

SDEYTLLTIH TVHVEPSQET ASHNKGLWIL VPSAILAAFL

LIWSVKCCRA QLEARRSRHP ADGAQQERCC VPPGERCPSA

PDNGEENVPL SGKV
```

The human B7-H7 has been reported to contain the following predicted domains based on in silico analysis: a signal sequence at amino acid residues 1 to 22 of SEQ ID NO:1, an Ig-like V-type 1 domain at amino acid residues 61 to 131 of SEQ ID NO:1, an Ig-like C-1 type domain at amino acid residues 138 to 222 of SEQ ID NO:1, an Ig-like V-type 2 domain at amino acid residues 235 to 328 of SEQ ID NO:1, and a transmembrane domain at amino acid residues 345 to 365 of SEQ ID NO:1. The predicted dimer interface for human B7-H7 polypeptide is amino acid residues 141-144, 156, 158, 160, 162, 193-196, 198, 200, 201, 224, and 225 of SEQ ID NO:1. The predicted N-linked glycosylation sites for human B7-H7 polypeptide are at amino acid residues 90, 103, and 318 of SEQ ID NO:1. Natural variations of human B7-H7 polypeptide include BOT, N344K, and S346R (UniProt Q9UM44) (see, WO 2011/020024, which reference is herein incorporated by reference in its entirety for its teaching of the structure and sequence of human B7-H7).

A DNA sequence encoding human B7-H7 (SEQ ID NO:1) is (SEQ ID NO:2):

```
atgaaggcac agacagcact gtctttcttc ctcattctca
taacatctct gagtggatct caaggcatat tccctttggc
tttcttcatt tatgttccta tgaatgaaca aatcgtcatt
ggaagacttg atgaagtat aattctccct tcttcatttg
agagggatc cgaagtcgta atacactgga agtatcaaga
tagctataag gttcatagtt actacaaagg cagtgaccat
ttggaaagcc aagatcccag atatgcaaac aggacatccc
ttttctataa tgagattcaa aatgggaatg cgtcactatt
tttcagaaga gtaagccttc tggacgaagg aatttacacc
tgctatgtag aacagcaat tcaagtgatt acaaacaaag
tggtgctaaa ggtgggagtt tttctcacac ccgtgatgaa
gtatgaaaag aggaacacaa acagcttctt aatatgcagc
gtgttaagtg tttatcctcg tccaattatc acgtggaaaa
tggacaacac acctatctct gaaaacaaca tggaagaaac
agggtctttg gattctttt ctattaacag cccactgaat
attacaggat caaattcatc ttatgaatgt acaattgaaa
attcactgct gaagcaaaca tggacagggc gctggacgat
gaaagatggc cttcataaaa tgcaaagtga acacgtttca
ctctcatgtc aacctgtaaa tgattatttt tcaccaaacc
aagacttcaa agttacttgg tccagaatga aaagtgggac
tttctctgtc ctggcttact atctgagctc ctcacaaaat
acaattatca atgaatcccg attctcatgg aacaaagagc
tgataaacca gagtgacttc tctatgaatt tgatggatct
taatctttca gacagtgggg aatatttatg caatatttct
tcggatgaat atactttact taccatccac acagtgcatg
tagaaccgag ccaagaaaca gcttcccata caaaggctt
atggattttg gtgccctctg cgattttggc agcttttctg
ctgatttgga gcgtaaaatg ttgcagagcc cagctagaag
ccaggaggag cagacaccct gctgatggag cccaacaaga
aagatgttgt gtccctcctg gtgagcgctg tcccagtgca
cccgataatg gcgaagaaaa tgtgcctctt tcaggaaaag
ta
```

In contrast to human B7-H4, which is widely expressed, human B7-H7 is found to exhibit more limited expression (e.g., expressed in the gut, kidney, lung, epithelial cells and lymphocytes). Human HHLA2 is found on chromosome 3q13.33 near B7.1 and B7.2. B7-H7 is constitutively expressed on macrophages and inducible on dendritic cells (DC).

B. H7CR

As used herein, the term "native H7CR" refers to any naturally occurring counter-receptor of B7-H7. H7CR is also referred to as B7-H7CR and CD28H. H7CR is expressed by T cells, NK cells, and plasmacytoid dendritic cells. The human H7CR polypeptide is otherwise referred to as transmembrane and immunoglobulin domain containing 2 (TMIGD2) in the literature/databases (Rahimi, N. et al. (Epub 2012 Mar. 14) "*Identification Of IGPR-1 As A Novel Adhesion Molecule Involved In Angiogenesis*," Molec. Biol. Cell. 23(9):1646-1656) but the function of B7-H7CR was not previously elucidated. Non-limiting examples of Accession Nos. for the amino acid sequence of such native H7CR molecules include: Q96BF3-1 (*homo sapiens*), Q96BF3-2 (*homo sapiens*), NP_653216.1 (GI:21389429; *homo sapiens*) and NP_653216.2 (GI:281306838; *homo sapiens*). A representative amino acid sequence (Q96BF3-2) of a native H7CR molecule is provided below as SEQ ID NO:3:

```
MGSPGMVLGL LVQIWALQEA SSLSVQQGPN LLQVRQGSQA
TLVCQVDQAT AWERLRVKWT KDGAILCQPY ITNGSLSLGV
CGPQGRLSWQ APSHLTLQLD PVSLNHSGAY VCWAAVEIPE
LEEAEGNITR LFVDPDDPTQ NRNRIASFPG FLFVLLGVGS
MGVAAIVWGA WFWGRRSCQQ RDSGNSPGNA FYSNVLYRPR
GAPKKSEDCS GEGKDQRGQS IYSTSFPQPA PRQPHLASRP
CPSPRPCPSP RPGHPVSMVR VSPRPSPTQQ PRPKGFPKVG
EE
```

A DNA sequence encoding human H7CR (SEQ ID NO:3) is (SEQ ID NO:4):

```
atggggtccc cgggcatggt gctgggcctc ctggtgcaga
tctgggccct gcaagaagcc tcaagcctga gcgtgcagca
ggggcccaac ttgctgcagg tgaggcaggg cagtcaggcg
accctggtct gccaggtgga ccaggccaca gcctgggaac
ggctccgtgt taagtggaca aaggatgggg ccatcctgtg
tcaaccgtac atcaccaacg gcagcctcag cctgggggtc
tgcgggcccc agggacggct ctcctggcag gcacccagcc
atctcaccct gcagctggac cctgtgagcc tcaaccacag
cgggggcgtac gtgtgctggg cggccgtaga gattcctgag
ttggaggagg ctgagggcaa cataacaagg ctctttgtgg
acccagatga ccccacacag aacagaaacc ggatcgcaag
cttcccagga ttcctcttcg tgctgctggg ggtgggaagc
atgggtgtgg ctgcgatcgt gtggggtgcc tggttctggg
gccgccgcag ctgccagcaa agggactcag gtaacagccc
aggaaatgca ttctacagca acgtcctata ccggccccgg
ggggccccaa agaagagtga ggactgctct ggagagggga
aggaccagag gggccagagc atttattcaa cctccttccc
gcaaccggcc cccgccagc cgcacctggc gtcaagaccc
tgcccagcc cgagaccctg cccagcccc aggcccggcc
accccgtctc tatggtcagg gtctctccta gaccaagccc
```

```
cacccagcag ccgaggccaa aagggttccc caaagtggga gaggag
```

C. Definitions

As used herein, a molecule is said to be able to "immunospecifically bind" a second molecule if such binding exhibits the specificity and affinity of an antibody to its cognate antigen. Antibodies are said to be capable of "immunospecifically binding" to a target region or conformation ("epitope") of an antigen (and in particular, the antigen H7CR) if such binding involves the antigen recognition site of the immunoglobulin molecule. An antibody that immunospecifically binds to a particular antigen may bind to other antigens with lower affinity if the other antigen has some sequence or conformational similarity that is recognized by the antigen recognition site as determined by, e.g., immunoassays, BIACORE® assays, or other assays known in the art, but would not bind to a totally unrelated antigen. Preferably, however, antibodies (and their antigen binding fragments) will not cross-react with other antigens. Antibodies may also bind to other molecules in a way that is not immunospecific, such as to Fc receptors (FcR), by virtue of binding domains in other regions/domains of the molecule that do not involve the antigen recognition site, such as the Fc region.

The term "substantially," as used in the context of binding or exhibited effect, is intended to denote that the observed effect is physiologically or therapeutically relevant. Thus, for example, a molecule is able to substantially block an activity of H7CR if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete). Similarly, a molecule is said to have substantially the same immunospecificity and/or characteristic as another molecule, if such immunospecificities and characteristics are greater than 60% identical, greater than 70% identical, greater than 75% identical, greater than 80% identical, greater than 85% identical, greater than 90% identical, greater than 95% identical, or greater than 97% identical).

As used herein, the term "subject" is intended to denote a mammal such as a non-primate (e.g., cows, pigs, horses, cats, dogs, rats etc.) and a primate (e.g., monkey and human), most preferably a human. The term "patient" is intended to denote a subject receiving a disclosed composition for a diagnostic, therapeutic or prophylactic purpose.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079), single-chain Fvs (scFv) (see, e.g., see Pluckthun in *The Pharmacology of Monoclonal Antibodies*, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to antibodies disclosed herein). In particular, such antibodies include immunoglobulin molecules of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the term "antigen binding fragment" of an antibody refers to one or more portions of an antibody that contain the antibody's Complementarity Determining Regions ("CDRs") and optionally the framework residues that include the antibody's "variable region" antigen recognition site, and exhibit an ability to immunospecifically bind antigen. Such fragments include Fab', $F(ab')_2$, Fv, single chain (ScFv), and mutants thereof, naturally occurring variants, and fusion proteins including the antibody's "variable region" antigen recognition site and a heterologous protein (e.g., a toxin, an antigen recognition site for a different antigen, an enzyme, a receptor or receptor ligand, etc.). As used herein, the term "fragment" refers to a peptide or polypeptide including an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

Human, chimeric or humanized antibodies are particularly preferred for in vivo use in humans, however, murine antibodies or antibodies of other species may be advantageously employed for many uses (for example, in vitro or in situ detection assays, acute in vivo use, etc.). Completely human antibodies are particularly desirable for therapeutic treatment of human subjects.

Human antibodies can be made by a variety of methods known in the art including phage display methods described above using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide. Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

A "chimeric antibody" is a molecule in which different portions of the antibody are derived from different immunoglobulin molecules such as antibodies having a variable region derived from a non-human antibody and a human immunoglobulin constant region. Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 6,311,415, 5,807,715, 4,816,567, and 4,816,397. Chimeric antibodies containing one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan, 1991, Molecular Immunology 28(4/5):489-498; Studnicka et al., 1994, Protein Engineering 7:805; and Roguska et al., 1994, Proc. Natl. Acad. Sci. USA 91:969), and chain shuffling (U.S. Pat. No. 5,565,332).

"Humanized antibodies" are known in the art (see, e.g., European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, Molecular Immunology 28(4/5):489-498; Studnicka et al., 1994, Protein Engineering 7(6):805-814; Roguska et al., 1994, PNAS 91:969-973; Tan et al., 2002, J. Immunol. 169:1119-1125; Caldas et al., 2000, Protein Eng. 13:353-360; Morea et al., 2000, Methods 20:267-79; Baca et al., 1997, J. Biol. Chem. 272:10678-10684; Roguska et al., 1996, Protein Eng. 9:895-904; Couto et al., 1995, Cancer Res. 55 (23 Supp):5973s-5977s; Couto et al., 1995, Cancer Res. 55:1717-22; Sandhu, 1994, Gene 150:409-10; Pedersen et al., 1994, J. Mol. Biol. 235:959-973; Jones et al., 1986, Nature 321:522-525; Reichmann et al., 1988, Nature 332:323-329; and Presta, 1992, Curr. Op. Struct. Biol. 2:593-596). As used herein, the term "humanized antibody" refers to an immunoglobulin including a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A humanized antibody is an antibody containing a humanized light chain and a humanized heavy chain immunoglobulin. For example, a humanized antibody would not encompass a typical chimeric antibody, because, e.g., the entire variable region of a chimeric antibody is non-human. A donor antibody has been "humanized," by the process of "humanization," because the resultant humanized antibody is expected to bind to the same antigen as the donor antibody that provides the CDR's. For the most part, humanized antibodies are human immunoglobulins (recipient antibody) in which hypervariable region residues of the recipient are replaced by hypervariable region residues from a non-human species (donor antibody) such as mouse, rat, rabbit or a non-human primate having the desired specificity, affinity, and capacity. In some instances, Framework Region (FR) residues of the human immunoglobulin are replaced by corresponding non-human residues. Furthermore, humanized antibodies may include residues which are not found in the recipient antibody or in the donor antibody. These modifications are made to further refine antibody performance. In general, the humanized antibody will include substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will include at least a portion of an immunoglobulin constant region (Fc), typically that of a human immunoglobulin that immunospecifically binds to an FcγRIIB polypeptide, that has been altered by the introduction of amino acid residue substitutions, deletions or additions (i.e., mutations).

Human, chimeric or humanized derivatives of anti-human H7CR antibodies are particularly preferred for in vivo use in humans, however, murine antibodies or antibodies of other species may be advantageously employed for many uses (for example, in vitro or in situ detection assays, acute in vivo use, etc.). Such a human or humanized antibody include amino acid residue substitutions, deletions or additions in one or more non-human CDRs. The humanized antibody derivative may have substantially the same binding, stronger binding or weaker binding when compared to a non-derivative humanized antibody. In specific embodiments, one, two, three, four, or five amino acid residues of the CDR have been substituted, deleted or added (i.e., mutated). Completely human antibodies are particularly desirable for therapeutic treatment of human subjects.

Such human antibodies can be made by a variety of methods known in the art including phage display methods using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Such human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide. Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

The antibodies used in the disclosed methods may be monospecific. Also of interest are bispecific antibodies, trispecific antibodies or antibodies of greater multispecificity that exhibit specificity to different targets in addition to H7CR, such as other molecules of the immune system. For example, such antibodies may bind to both H7CR and to an antigen that is important for targeting the antibody to a particular cell type or tissue (for example, to an antigen associated with a cancer antigen of a tumor being treated). In another embodiment, such multispecific antibody binds to both B7-H7 and to H7CR, and thus serves to promote association of cells possessing such molecules to thereby agonize T cell responses. Such molecules have particular utility in the treatment of cancer and infectious disease. In another embodiment, such multispecific antibody binds to molecules (receptors or ligands) involved in alternative or supplemental immunomodulatory pathways, such as CTLA4, TIM3, TIM4, OX40, CD40, GITR, 4-1-BB, B7-H4, LIGHT or LAG3, in order to enhance the immunomodulatory effects. Furthermore, the multispecific antibody may bind to effector molecules such as cytokines (e.g., IL-7, IL-15, IL-12, IL-4 TGF-beta, IL-10, IL-17, IFNg, Flt3, BLys) and chemokines (e.g., CCL21), which may be particularly relevant for modulating both acute and chronic immune responses.

DNA sequences coding for preferred human acceptor framework sequences include but are not limited to FR segments from the human germline VH segment VH1-18 and JH6 and the human germline VL segment VK-A26 and JK4. In a specific embodiment, one or more of the CDRs are inserted within framework regions using routine recombinant DNA techniques. The framework regions may be naturally occurring or consensus framework regions, and preferably human framework regions (see, e.g., Chothia et al., 1998, "*Structural Determinants In The Sequences Of Immunoglobulin Variable Domain*," J. Mol. Biol. 278: 457-479 for a listing of human framework regions).

The disclosed humanized or chimeric antibody may contain substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, the antibody also includes at least a portion of an immunoglobulin constant region (Fc), typically that of a human immunoglobulin. The constant domains of the antibodies may be selected with respect to the proposed function of the antibody, in particular the effector function which may be required. In some embodiments, the constant domains of the antibodies are (or include) human IgA, IgD, IgE, IgG or IgM domains. In a specific embodiment, human IgG constant domains, especially of the IgG1 and IgG3 isotypes are used, when the humanized antibodies are intended for therapeutic uses and antibody effector functions such as antibody-dependent cell-mediated cytotoxicity (ADCC) and complement-dependent cytotoxicity (CDC) activity are needed. In alternative embodiments, IgG2 and IgG4 isotypes are used when the antibody is intended for therapeutic purposes and antibody effector function is not required. The Fc constant domains of the antibodies can include one or more amino acid modifications which alter antibody effector functions such as those disclosed in U.S. Patent Application Publication Nos. 2005/0037000 and 2005/0064514.

In some embodiments, the antibody contains both the light chain as well as at least the variable domain of a heavy chain. In other embodiments, the antibody may further include one or more of the CHL hinge, CH2, CH3, and CH4 regions of the heavy chain. The antibody can be selected from any class of immunoglobulins, including IgM, IgG, IgD, IgA and IgE, and any isotype, including $IgG_1$, $IgG_2$, $IgG_3$ and $IgG_4$. In some embodiments, the constant domain is a complement fixing constant domain where it is desired that the antibody exhibit cytotoxic activity, and the class is typically $IgG_1$. In other embodiments, where such cytotoxic activity is not desirable, the constant domain may be of the $IgG_2$ class. The antibody may include sequences from more than one class or isotype, and selecting particular constant domains to optimize desired effector functions is within the ordinary skill in the art.

In a specific aspect, the present disclosure provides an Fc variant, wherein the Fc region includes at least one modification (e.g., amino acid substitutions, amino acid insertions, amino acid deletions) at one or more positions selected from the group consisting of 228, 234, 235 and 331 as numbered by the EU index as set forth in Kabat et al. (1991, NIH Publication 91-3242, National Technical Information Service, Springfield, Va.). In one aspect, the modification is at least one substitution selected from the group consisting of 228P, 234F, 235E, 235F, 235Y, and 331S as numbered by the EU index as set forth in Kabat.

In another specific aspect, the present disclosure provides an Fc variant, wherein the Fc region is an IgG4 Fc region and includes at least one modification at one or more positions selected from the group consisting of 228 and 235 as numbered by the EU index as set forth in Kabat. In still another specific aspect, the Fc region is an IgG4 Fc region and the non-naturally occurring amino acids are selected from the group consisting of 228P, 235E and 235Y as numbered by the EU index as set forth in Kabat.

In another specific aspect, the present disclosure provides an Fc variant, wherein the Fc region includes at least one non-naturally occurring amino acid at one or more positions selected from the group consisting of 239, 330 and 332 as numbered by the EU index as set forth in Kabat. In one aspect, the modification is at least one substitution selected from the group consisting of 239D, 330L, 330Y, and 332E as numbered by the EU index as set forth in Kabat. See, U.S. Pat. No. 7,317,091, incorporated herein by referenced in its entirety.

In a specific aspect, the present disclosure provides an Fc variant 1, wherein the Fc region includes at least one non-naturally occurring amino acid at one or more positions selected from the group consisting of 252, 254, and 256 as numbered by the EU index as set forth in Kabat. In one aspect, the modification is at least one substitution selected from the group consisting of 252Y, 254T and 256E as numbered by the EU index as set forth in Kabat. See, U.S. Pat. No. 7,083,784, incorporated herein by reference in its entirety.

In certain aspects, the present disclosure provides an Fc variant, wherein the Fc region includes a non-naturally occurring amino acid at position 428 as numbered by the EU index as set forth in Kabat. In one aspect, the modification at position 428 is selected from the group consisting of 428T, 428L, 428F, and 428S as numbered by the EU index as set forth in Kabat. See, U.S. Pat. No. 7,670,600, incorporated herein by reference in its entirety. In another aspect, an Fc variant may further includes a non-naturally occurring amino acid at position 434 as numbered by the EU index as set forth in Kabat. In one aspect, the modification at position 434 is selected from the group consisting of 434A, 434S, and 434F as numbered by the EU index as set forth in Kabat. In other aspects, the present disclosure provides an Fc variant, wherein the Fc region includes a non-naturally occurring amino acid at positions 428 and 434 as numbered by the EU index as set forth in Kabat. In a specific aspect, the Fc region includes 428L, 434S. See, U.S. Pat. No. 8,088,376.

The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the donor antibody. Such mutations, however, are preferably not extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including, but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, *Molecular Immunology* 28(4/5):489-498; Studnicka et al., 1994, *Protein Engineering* 7(6):805-814; and Roguska et al., 1994, *Proc. Natl. Acad. Sci.* 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, *J. Immunol.* 169:1119-25, Caldas et al., 2000, *Protein Eng.* 13:353-60, Morea et al., 2000, *Methods* 20:267-79, Baca et al., 1997, *J. Biol. Chem.* 272:10678-84, Roguska et al., 1996, *Protein Eng.* 9:895-904, Couto et al., 1995, *Cancer Res.* 55 (23 Supp):5973s-5977s, Couto et al., 1995, *Cancer Res.* 55:1717-22, Sandhu, 1994, *Gene* 150:409-10, Pedersen et al., 1994, *J. Mol. Biol.* 235:959-73, Jones et al., 1986, *Nature* 321:522-525, Riechmann et al., 1988, *Nature* 332:323, and Presta, 1992, *Curr. Op. Struct. Biol.* 2:593-596. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; U.S. Publication Nos. 2004/0049014 and 2003/0229208; U.S. Pat. Nos. 6,350,861; 6,180,370; 5,693,762; 5,693,761; 5,585,089; and 5,530,101 and Riechmann et al., 1988, *Nature* 332:323).

The antibodies may be produced by any method known in the art useful for the production of polypeptides, e.g., in vitro synthesis, recombinant DNA production, and the like. Preferably, the humanized antibodies are produced by recombinant DNA technology. The antibodies may be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757. Techniques for the recombinant expression of immunoglobulins, including humanized immunoglobulins, can also be found, in Goeddel et al., Gene Expression Technology Methods in Enzymology Vol. 185 Academic Press (1991), and Borreback, Antibody Engineering, W. H. Freeman (1992). Additional information concerning the generation, design and expression of recombinant antibodies can be found in Mayforth, Designing Antibodies, Academic Press, San Diego (1993).

An exemplary process for the production of the recombinant chimeric antibodies may include the following: a) constructing, by conventional molecular biology methods, an expression vector that encodes and expresses an antibody heavy chain in which the CDRs and variable region of a murine anti-human H7CR monoclonal antibody are fused to an Fc region derived from a human immunoglobulin, thereby producing a vector for the expression of a chimeric antibody heavy chain; b) constructing, by conventional molecular biology methods, an expression vector that encodes and expresses an antibody light chain of the murine anti-human H7CR monoclonal antibody, thereby producing a vector for the expression of chimeric antibody light chain; c) transferring the expression vectors to a host cell by conventional molecular biology methods to produce a transfected host cell for the expression of chimeric antibodies; and d) culturing the transfected cell by conventional cell culture techniques so as to produce chimeric antibodies.

An exemplary process for the production of the recombinant humanized antibodies may include the following: a) constructing, by conventional molecular biology methods, an expression vector that encodes and expresses an anti-human H7CR heavy chain in which the CDRs and a minimal portion of the variable region framework that are required to retain donor antibody binding specificity are derived from a non-human immunoglobulin, such as a murine anti-human H7CR monoclonal antibody, and the remainder of the antibody is derived from a human immunoglobulin, thereby producing a vector for the expression of a humanized antibody heavy chain; b) constructing, by conventional molecular biology methods, an expression vector that encodes and expresses an antibody light chain in which the CDRs and a minimal portion of the variable region framework that are required to retain donor antibody binding specificity are derived from a non-human immunoglobulin, such as a murine anti-human H7CR monoclonal antibody, and the remainder of the antibody is derived from a human immunoglobulin, thereby producing a vector for the expression of humanized antibody light chain; c) transferring the expression vectors to a host cell by conventional molecular biology methods to produce a transfected host cell for the expression of humanized antibodies; and d) culturing the transfected cell by conventional cell culture techniques so as to produce humanized antibodies.

With respect to either exemplary method, host cells may be co-transfected with such expression vectors, which may contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains may include cDNA or genomic DNA or both. The host cell used to express the recombinant antibody may be either a bacterial cell such as *Escherichia coli*, or more preferably a eukaryotic cell (e.g., a Chinese hamster ovary (CHO) cell or a HEK-293 cell). The choice of expression vector is dependent upon the choice of host cell, and may be selected so as to have the desired expression and regulatory characteristics in the selected host cell. Other cell lines that may be used include, but are not limited to, CHO-K1, NSO, and PER.C6 (Crucell, Leiden, Netherlands).

Any of the disclosed antibodies can be used to generate anti-idiotype antibodies using techniques well known to those skilled in the art (see, e.g., Greenspan, N. S. et al. (1989) *"Idiotypes: Structure And Immunogenicity,"* FASEB J. 7:437-444; and Nisinoff, A. (1991) *"Idiotypes: Concepts And Applications,"* J. Immunol. 147(8):2429-2438).

The binding properties of the disclosed antibodies can, if desired, be further improved by screening for variants that exhibit such desired characteristics. For example, such antibodies can be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, include those disclosed in Brinkman, U. et al. (1995) *"Phage Display Of Disulfide-Stabilized Fv Fragments,"* J. Immunol. Methods, 182:41-50, 1995; Ames, R. S. et al. (1995) *"Conversion Of Murine Fabs Isolated From A Combinatorial Phage Display Library To Full Length Immunoglobulins,"* J. Immunol. Methods, 184:177-186; Kettleborough, C. A. et al. (1994) *"Isolation Of Tumor Cell-Specific Single-Chain Fv From Immunized Mice Using Phage-Antibody Libraries And The Re-Construction Of Whole Antibodies From These Antibody Fragments,"* Eur. J. Immunol., 24:952-958, 1994; Persic, L. et al. (1997) *"An Integrated Vector System For The Eukaryotic Expression Of Antibodies Or Their Fragments After Selection From Phage Display Libraries,"* Gene, 187: 9-18; Burton, D. R. et al. (1994) *"Human Antibodies From Combinatorial Libraries,"* Adv. Immunol. 57:191-280; PCT Publications WO 92/001047; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

As described in the above references, after phage selection, the antibody coding regions from the phage can be isolated and used to generate whole antibodies, including humanized antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art (such as those disclosed in PCT Publication WO 92/22324; Mullinax, R. L. et al. (1992) *"Expression Of A Heterodimeric Fab Antibody Protein In One Cloning Step,"* BioTechniques, 12(6):864-869; and Sawai et al. (1995) *"Direct Production Of The Fab Fragment Derived From The Sperm Immobilizing Antibody Using Polymerase Chain Reaction And cDNA Expression Vectors,"* Am. J. Reprod. Immunol. 34:26-34; and Better, M. et al. (1988) *"Escherichia coli Secretion Of An Active Chimeric Antibody Fragment,"* Science 240:1041-1043). Examples of techniques which can be used to produce single-chain Fvs and antibodies include those described in U.S. Pat. Nos. 4,946,778 and 5,258,498; Huston, J. S. et al. (1991) *"Protein Engineering Of Single-Chain Fv Analogs And Fusion Proteins,"* Methods in Enzymology 203:46-88; Shu, L. et al., *"Secretion Of A Single-Gene-Encoded Immunoglobulin From Myeloma Cells,"* Proc. Natl. Acad. Sci. (USA) 90:7995-7999; and Skerra. A. et al. (1988) *"Assembly Of A Functional Immunoglobulin Fv Fragment In Escherichia coli,"* Science 240:1038-1040.

Phage display technology can be used to increase the affinity of the disclosed antibodies for H7CR. This technique would be useful in obtaining high affinity antibodies that could be used in the combinatorial methods. This technology, referred to as affinity maturation, employs mutagenesis or CDR walking and re-selection using such receptors or ligands (or their extracellular domains) or an antigenic fragment thereof to identify antibodies that bind with higher affinity to the antigen when compared with the initial or parental antibody (See, e.g., Glaser, S. M. et al. (1992) "*Antibody Engineering By Codon-Based Mutagenesis In A Filamentous Phage Vector System*," J. Immunol. 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (see, e.g., Wu, H. et al. (1998) "*Stepwise In Vitro Affinity Maturation Of Vitaxin, An Alphav Beta3-Specific Humanized Mab*," Proc. Natl. Acad. Sci. (USA) 95(11): 6037-6042; Yelton, D. E. et al. (1995) "*Affinity Maturation Of The BR96 Anti-Carcinoma Antibody By Codon-Based Mutagenesis*," J. Immunol. 155:1994-2004). CDR walking which randomizes the light chain may be used possible (see, Schier et al. (1996) "*Isolation Of Picomolar Affinity Anti-C-Erbb-2 Single-Chain Fv By Molecular Evolution Of The Complementarity Determining Regions In The Center Of The Antibody Binding Site*," J. Mol. Biol. 263:551-567).

Random mutagenesis can also be used to identify improved CDRs. Phage display technology can alternatively be used to increase (or decrease) CDR affinity. This technology, referred to as affinity maturation, employs mutagenesis or "CDR walking" and re-selection uses the target antigen or an antigenic fragment thereof to identify antibodies having CDRs that bind with higher (or lower) affinity to the antigen when compared with the initial or parental antibody (see, e.g., Glaser, S. M. et al. (1992) "*Antibody Engineering By Codon-Based Mutagenesis In A Filamentous Phage Vector System*," J. Immunol. 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify mutant antibodies with increased (or decreased) avidity to the antigen (e.g., ELISA) (see, Wu, H. et al. (1998) "*Stepwise In Vitro Affinity Maturation Of Vitaxin, An Alphav Beta3-Specific Humanized Mab*," Proc. Natl. Acad. Sci. (USA) 95(11):6037-6042; Yelton, D. E. et al. (1995) "*Affinity Maturation Of The BR96 Anti-Carcinoma Antibody By Codon-Based Mutagenesis*," J. Immunol. 155:1994-2004). CDR walking which randomizes the light chain may be used possible (see, Schier et al. (1996) "*Isolation Of Picomolar Affinity Anti-C-Erbb-2 Single-Chain Fv By Molecular Evolution Of The Complementarity Determining Regions In The Center Of The Antibody Binding Site*," J. Mol. Biol. 263: 551-567).

Methods for accomplishing such affinity maturation are described for example in: Krause, J. C. et al. (2011) "*An Insertion Mutation That Distorts Antibody Binding Site Architecture Enhances Function Of A Human Antibody*," M Bio. 2(1) pii: e00345-10. doi: 10.1128/mBio.00345-10; Kuan, C. T. et al. (2010) "*Affinity-Matured Anti-Glycoprotein NMB Recombinant Immunotoxins Targeting Malignant Gliomas And Melanomas*," Int. J. Cancer 10.1002/ijc.25645; Hackel, B. J. et al. (2010) "*Stability And CDR Composition Biases Enrich Binder Functionality Landscapes*," J. Mol. Biol. 401(1):84-96; Montgomery, D. L. et al. (2009) "*Affinity Maturation And Characterization Of A Human Monoclonal Antibody Against HIV-1 gp41*," MAbs 1(5):462-474; Gustchina, E. et al. (2009) "*Affinity Maturation By Targeted Diversification Of The CDR-H2 Loop Of A Monoclonal Fab Derived From A Synthetic Naïve Human Antibody Library And Directed Against The Internal Trimeric Coiled-Coil Of Gp41 Yields A Set Of Fabs With Improved HIV-1 Neutralization Potency And Breadth*," Virology 393(1):112-119; Finlay, W. J. et al. (2009) "*Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions*," J. Mol. Biol. 388(3):541-558; Bostrom, J. et al. (2009) "*Improving Antibody Binding Affinity And Specificity For Therapeutic Development*," Methods Mol. Biol. 525: 353-376; Steidl, S. et al. (2008) "*In Vitro Affinity Maturation Of Human GM-CSF Antibodies By Targeted CDR-Diversification*," Mol. Immunol. 46(1):135-144; and Barderas, R. et al. (2008) "Affinity maturation of antibodies assisted by in silico modeling," Proc. Natl. Acad. Sci. (USA) 105(26): 9029-9034.

The production and use of "derivatives" of any of the above-described antibodies and their antigen-binding fragments are also provided.

The term "derivative" refers to an antibody or antigen-binding fragment thereof that immunospecifically binds to an antigen but which includes, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, chimeric or humanized variants of any of antibodies 1.3, 4.5 or 7.8, as well as variants having altered CH1, hinge, CH2, CH3 or CH4 regions, so as to form, for example antibodies, etc., having variant Fc regions that exhibit enhanced or impaired effector or binding characteristics. The term "derivative" additionally encompasses non amino acid modifications, for example, amino acids that may be glycosylated (e.g., have altered mannose, 2-N-acetylglucosamine, galactose, fuctose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "*Lack Of Fucose On Human IgG N-Linked Oligosaccharide Improves Binding To Human Fcgamma RIII And Antibody-Dependent Cellular Toxicity.*," J. Biol. Chem. 277(30): 26733-26740; Davies J. et al. (2001) "*Expression Of GnTIII*

In A Recombinant Anti-CD20 CHO Production Cell Line: Expression Of Antibodies With Altered Glycoforms Leads To An Increase In ADCC Through Higher Affinity For FC Gamma RIII," Biotechnology & Bioengineering 74(4): 288-294). Methods of altering carbohydrate contents are known to those skilled in the art, see, e.g., Wallick, S. C. et al. (1988) "Glycosylation Of A VH Residue Of A Monoclonal Antibody Against Alpha (1-6) Dextran Increases Its Affinity For Antigen," J. Exp. Med. 168(3): 1099-1109; Tao, M. H. et al. (1989) "Studies Of Aglycosylated Chimeric Mouse-Human IgG. Role Of Carbohydrate In The Structure And Effector Functions Mediated By The Human IgG Constant Region," J. Immunol. 143(8): 2595-2601; Routledge, E. G. et al. (1995) "The Effect Of Aglycosylation On The Immunogenicity Of A Humanized Therapeutic CD3 Monoclonal Antibody," Transplantation 60(8):847-53; Elliott, S. et al. (2003) "Enhancement Of Therapeutic Protein In Vivo Activities Through Glycoengineering," Nature Biotechnol. 21:414-21; Shields, R. L. et al. (2002) "Lack Of Fucose On Human IgG N-Linked Oligosaccharide Improves Binding To Human Fcgamma RIII And Antibody-Dependent Cellular Toxicity.," J. Biol. Chem. 277(30): 26733-26740).

In some embodiments, a humanized antibody is a derivative. Such a humanized antibody includes amino acid residue substitutions, deletions or additions in one or more non-human CDRs. The humanized antibody derivative may have substantially the same binding, better binding, or worse binding when compared to a non-derivative humanized antibody. In specific embodiments, one, two, three, four, or five amino acid residues of the CDR have been substituted, deleted or added (i.e., mutated).

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

Substitutions, additions or deletions in the derivatized antibodies may be in the Fc region of the antibody and may thereby serve to modify the binding affinity of the antibody to one or more FcγR. Methods for modifying antibodies with modified binding to one or more FcγR are known in the art, see, e.g., PCT Publication Nos. WO 04/029207, WO 04/029092, WO 04/028564, WO 99/58572, WO 99/51642, WO 98/23289, WO 89/07142, WO 88/07089, and U.S. Pat. Nos. 5,843,597 and 5,642,821. Some embodiments encompass antibodies whose Fc region will have been deleted (for example, an Fab or F(ab)2, etc.) or modified so that the molecule will exhibit diminished or no Fc receptor (FcR) binding activity, or will exhibit enhanced antibody-dependent cell-mediated cytotoxicity (ADCC) or complement dependent cytotoxicity (CDC) activities. Some embodiments, encompasses antibodies that have altered affinity for an activating FcγR, e.g., FcγRIIIA Preferably such modifications also have an altered Fc-mediated effector function. Modifications that affect Fc-mediated effector function are well known in the art (see U.S. Pat. No. 6,194,551, and WO 00/42072). In one particular embodiment, the modification of the Fc region results in an antibody with an altered antibody-mediated effector function, an altered binding to other Fc receptors (e.g., Fc activation receptors), an altered antibody-dependent cell-mediated cytotoxicity (ADCC) activity, an altered C1q binding activity, an altered complement-dependent cytotoxicity activity (CDC), a phagocytic activity, or any combination thereof.

Derivatized antibodies may be used to alter the half-lives (e.g., serum half-lives) of parental antibodies in a mammal, preferably a human. Preferably such alteration will result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the humanized antibodies or fragments thereof in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor. The humanized antibodies may be engineered to increase biological half-lives (see, e.g. U.S. Pat. No. 6,277,375). For example, humanized antibodies may be engineered in the Fc-hinge domain to have increased in vivo or serum half-lives.

Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The antibodies may also be modified by the methods and coupling agents described by Davis et al. (See U.S. Pat. No. 4,179,337) in order to provide compositions that can be injected into the mammalian circulatory system with substantially no immunogenic response.

The framework residues of the humanized antibodies can be modified. Framework residues in the framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann, L. et al. (1988) "Reshaping Human Antibodies For Therapy," Nature 332:323-327).

Anti-human H7CR antibodies (and more preferably, humanized antibodies) and antigen-binding fragments thereof that are recombinantly fused or chemically conjugated (including both covalently and non-covalently conjugations) to a heterologous molecule (i.e., an unrelated molecule) are also provided. The fusion does not necessarily need to be direct, but may occur through linker sequences.

In one embodiment such heterologous molecules are polypeptides having at least 10, at least 20, at least 30, at least 40, at least 50, at least 60, at least 70, at least 80, at least 90 or at least 100 amino acids. Such heterologous molecules may alternatively be enzymes, hormones, cell surface receptors, drug moieties, such as: toxins (such as abrin, ricin A, pseudomonas exotoxin (i.e., PE-40), diphtheria toxin, ricin, gelonin, or pokeweed antiviral protein), proteins (such as tumor necrosis factor, interferon (e.g., α-interferon, β-interferon), nerve growth factor, platelet derived growth factor, tissue plasminogen activator, or an apoptotic agent (e.g., tumor necrosis factor-α, tumor necrosis factor-β)), biological response modifiers (such as, for example, a lymphokine (e.g., interleukin-1 ("IL-1"), interleukin-2 ("IL-2"), interleukin-6 ("IL-6")), granulocyte macrophage colony stimulating factor ("GM-CSF"), granulocyte colony stimulating factor ("G-CSF"), or macrophage colony stimulating factor, ("M-CSF")), or growth factors (e.g., growth hormone ("GH"))), cytotoxins (e.g., a cytostatic or cytocidal agent, such as paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof), antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, BiCNU® (carmustine; BSNU) and lomustine (CCNU), cyclothosphamide, busulfan, dibromomannitol, streptozotocin, mitomycin C, and cisdichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), or anti-mitotic agents (e.g., vincristine and vinblastine).

Techniques for conjugating such therapeutic moieties to antibodies are well known; see, e.g., Arnon et al., "*Monoclonal Antibodies For Immunotargeting Of Drugs In Cancer Therapy*", in MONOCLONAL ANTIBODIES AND CANCER THERAPY, Reisfeld et al. (eds.), 1985, pp. 243-56, Alan R. Liss, Inc.); Hellstrom et al., "*Antibodies For Drug Delivery*", in CONTROLLED DRUG DELIVERY (2nd Ed.), Robinson et al. (eds.), 1987, pp. 623-53, Marcel Dekker, Inc.); Thorpe, "*Antibody Carriers Of Cytotoxic Agents In Cancer Therapy: A Review*", in MONOCLONAL ANTIBODIES '84: BIOLOGICAL AND CLINICAL APPLICATIONS, Pinchera et al. (eds.), 1985, pp. 475-506); "*Analysis, Results, And Future Prospective Of The Therapeutic Use Of Radiolabeled Antibody In Cancer Therapy*", in MONOCLONAL ANTIBODIES FOR CANCER DETECTION AND THERAPY, Baldwin et al. (eds.), 1985, pp. 303-16, Academic Press; and Thorpe et al. (1982) "*The Preparation And Cytotoxic Properties Of Antibody-Toxin Conjugates*," Immunol. Rev. 62:119-158.

In one embodiment, the antibodies or fusion molecules include an Fc portion. The Fc portion of such molecules may be varied by isotype or subclass, may be a chimeric or hybrid, and/or may be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, J. P. et al. (1997) "*Humanized Porcine VCAM-Specific Monoclonal Antibodies With Chimeric IgG2/G4 Constant Regions Block Human Leukocyte Binding To Porcine Endothelial Cells*," Mol. Immun. 34(6): 441-452, Swann, P. G. (2008) "*Considerations For The Development Of Therapeutic Monoclonal Antibodies*," Curr. Opin. Immun. 20:493-499 (2008), and Presta, L. G. (2008) "*Molecular Engineering And Design Of Therapeutic Antibodies*," Curr. Opin. Immun 20:460-470. In some embodiments the Fc region is the native IgG1, IgG2, or IgG4 Fc region. In some embodiments the Fc region is a hybrid, for example a chimeric consisting of IgG2/IgG4 Fc constant regions. Modifications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn, and IgG4 with serine at amino acid resident #228 in the hinge region changed to proline (S228P) to enhance stability. The Fc region may include the entire hinge region, or less than the entire hinge region.

The therapeutic outcome in patients treated with rituximab (a chimeric mouse/human IgG1 monoclonal antibody against CD20) for non-Hodgkin's lymphoma or Waldenstrom's macroglobulinemia correlated with the individual's expression of allelic variants of Fcγ receptors with distinct intrinsic affinities for the Fc domain of human IgG1. In particular, patients with high affinity alleles of the low affinity activating Fc receptor CD16A (FcγRIIIA) showed higher response rates and, in the cases of non-Hodgkin's lymphoma, improved progression-free survival. In another embodiment, the Fc domain may contain one or more amino acid insertions, deletions or substitutions that reduce binding to the low affinity inhibitory Fc receptor CD32B (FcγRIIB) and retain wild-type levels of binding to or enhance binding to the low affinity activating Fc receptor CD16A (FcγRIIIA).

Another embodiment includes IgG2-4 hybrids and IgG4 mutants that have reduce binding to FcR which increase their half-life. Representative IG2-4 hybrids and IgG4 mutants are described in Angal, S. et al. (1993) "*A Single Amino Acid Substitution Abolishes The Heterogeneity Of Chimeric Mouse/Human (Igg4) Antibody*," Molec. Immunol. 30(1):105-108; Mueller, J. P. et al. (1997) "*Humanized Porcine VCAM-Specific Monoclonal Antibodies With Chimeric Igg2/G4 Constant Regions Block Human Leukocyte Binding To Porcine Endothelial Cells*," Mol. Immun. 34(6): 441-452; and U.S. Pat. No. 6,982,323. In some embodiments the IgG1 and/or IgG2 domain is deleted for example, Angal, s. et al. describe IgG1 and IgG2 having serine 241 replaced with a proline.

In a preferred embodiment, the Fc domain contains amino acid insertions, deletions or substitutions that enhance binding to CD16A. A large number of substitutions in the Fc domain of human IgG1 that increase binding to CD16A and reduce binding to CD32B are known in the art and are described in Stavenhagen, J. B. et al. (2007) "*Fc Optimization Of Therapeutic Antibodies Enhances Their Ability To Kill Tumor Cells In Vitro And Controls Tumor Expansion In Vivo Via Low-Affinity Activating Fcgamma Receptors*," Cancer Res. 57(18):8882-8890. Exemplary variants of human IgG1 Fc domains with reduced binding to CD32B and/or increased binding to CD16A contain F243L, R929P, Y300L, V3051 or P296L substitutions. These amino acid substitutions may be present in a human IgG1 Fc domain in any combination. In one embodiment, the human IgG1 Fc domain variant contains a F243L, R929P and Y300L substitution. In another embodiment, the human IgG1 Fc domain variant contains a F243L, R929P, Y300L, V3051 and P296L substitution. In another embodiment, the human IgG1 Fc domain variant contains an N297Q substitution, as this mutation abolishes FcR binding.

Any of the described molecules can be fused to marker sequences, such as a peptide, to facilitate purification. In preferred embodiments, the marker amino acid sequence is a hexa-histidine peptide, the hemagglutinin "HA" tag, which corresponds to an epitope derived from the influenza hemagglutinin protein (Wilson, I. A. et al. (1984) "*The Structure Of An Antigenic Determinant In A Protein*," Cell, 37:767-778) and the "flag" tag (Knappik, A. et al. (1994) "*An Improved Affinity Tag Based On The FLAG Peptide For The Detection And Purification Of Recombinant Antibody Fragments*," Biotechniques 17(4):754-761).

The antibodies or their antigen-binding fragments can be conjugated to a diagnostic or therapeutic agent or any other molecule for which serum half-life is desired to be increased. The antibodies can be used diagnostically (in vivo, in situ or in vitro) to, for example, monitor the development or progression of a disease, disorder or infection as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics. Such diagnosis and detection can be accomplished by coupling the antibody to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidin/biotin and avidin/biotin; fluorescent materials such as, but not limited to, umbelliferone, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanum ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn); positron emitting metals using various positron emission tomographies, and nonradioactive paramagnetic metal ions.

The molecules can be conjugated to a second antibody to form an antibody heteroconjugate as described by Segal in U.S. Pat. No. 4,676,980. Such heteroconjugate antibodies may additionally bind to haptens (such as fluorescein, etc.), or to cellular markers (e.g., 4-1-BB, B7-H4, B7-H7, CD4, CD8, CD14, CD25, CD27, CD40, CD68, CD163, CTLA4, GITR, LAG-3, OX40, TIM3, TIM4, TLR2, LIGHT, etc.) or to cytokines (e.g., IL-7, IL-15, IL-12, IL-4 TGF-beta, IL-10, IL-17, IFNg, Flt3, BLys) or chemokines (e.g., CCL21), etc.

The molecules may be attached to solid supports, which are particularly useful for immunoassays or purification of the target antigen or of other molecules that are capable of binding to target antigen that has been immobilized to the support via binding to an antibody or antigen-binding fragment. Such solid supports include, but are not limited to, glass, cellulose, polyacrylamide, nylon, polystyrene, polyvinyl chloride or polypropylene.

Nucleic acid molecules (DNA or RNA) that encode any such antibodies, fusion proteins or fragments, as well as vector molecules (such as plasmids) that are capable of transmitting or of replication such nucleic acid molecules and expressing such antibodies, fusion proteins or fragments in a cell line are also provided. The nucleic acids can be single-stranded, double-stranded, may contain both single-stranded and double-stranded portions.

D. Preferred Modulator Compositions

As used herein the term "modulate" relates to a capacity to alter an effect or result. In particular, a humanized variant of an anti-human H7CR antibody or any of its antigen-binding fragments that immunospecifically binds human H7CR or molecules that physiospecifically bind H7CR are capable of modulating the binding between H7CR and its cognate ligands and/or of modulating the signal transduction that occurs as a consequence of H7CR—cognate ligand binding.

The antibody can be an agonist antibody that agonizes H7CR. Agonizing antibodies can bind H7CR and stimulate signal transduction through H7CR.

In one embodiment, the antibodies, or fragments thereof, or fusion molecules immunospecifically bind to H7CR but are substantially incapable of blocking H7CR's interaction with B7-H7 in vitro, or in a recipient subject or patient. As used herein, a molecule that is "substantially incapable of blocking H7CR's interaction with B7-H7" denotes that the presence of such molecule attenuates H7CR-B7-H7 interactions by less than 50%, more preferably less than 40%, still more preferably less than 30%, still more preferably less than 20%, still more preferably less than 10%, still more preferably less than 5%, still more preferably less than 1%, and most preferably completely fails to attenuate such interaction, as measured by any of the assays disclosed herein. Such antibodies, fragments and fusion molecules have particular utility as therapeutic agents or in diagnostic, cytological and histological assays for H7CR (or B7-H7) expression. Additionally, multi-specific anti-H7CR antibodies, anti-H7CR antigen-binding fragments and their respective fusion products that have the added ability to bind B7-H7 or other cellular ligands or receptors have particular utility in facilitating the co-localization of cells expressing such ligands or receptors to cells that express H7CR.

In a second embodiment, the antibodies, or fragments thereof, or fusion molecules immunospecifically bind to H7CR and are capable of substantially blocking H7CR's interaction with B7-H7 in vitro, or in a recipient subject or patient. As used herein, a molecule that is "capable of substantially blocking H7CR's interaction with B7-H7" denotes that the provision of such molecule attenuates H7CR-B7-H7 interactions by more than 50%, more preferably by more than 60%, more than 70%, more than 80%, more than 90%, more than 95%, more than 99% or most preferably completely attenuates such interaction, as measured by any of the assays disclosed herein. Such antibodies, fragments and fusion molecules have particular utility in attenuating the biological effects of B7-H7-H7CR interactions.

A preferred embodiment provides humanized antibodies and fragments or human antibodies and fragments.

Most preferably, such molecules will possess sufficient affinity and avidity to be able to bind to H7CR when expressed at an endogenous concentration and arrayed on the surface of a subject's cells. The term "endogenous concentration" refers to the level at which a molecule is natively expressed (i.e., in the absence of expression vectors or recombinant promoters) in a normal, cancer or pathogen-infected cell.

(1) Preferred Rodent Anti-Human H7CR Antibodies and their CDRs

Such molecules can be produced by screening hybridoma lines for those that produce antibody that are immunospecific for human H7CR, and then optionally screening amongst such lines for those exhibiting modulating activity (e.g., neutralizing activity, agonizing activity, altered signal transducing activity, etc.). In one embodiment the antibodies are hamster anti-human H7CR clones: 1.3, 4.5 and 7.8. These antibodies are capable of binding to human H7CR and are substantially incapable of blocking H7CR's interaction with B7-H7. The antibodies expressed by the anti-human H7CR clones were sequenced to reveal their variable domains. CDR sequences of the variable domains are shown in bold and underlined:

```
Anti-Human H7CR Clone 1.3
Light Chain Variable Region:
                                     (SEQ ID NO: 5)
DIVMTQSPSS LAVSAGEKVT ISCLSSQSLF SSNTNRNYLN

WYLQKPGQSP KLLIYHASTR LTGVPDRFIG SGSGTDFTLT

ISSVQAEDLG DYYCQHHYET PLTFGDGTKL EIK

Heavy Chain Variable Region:
                                     (SEQ ID NO: 6)
QIQLQESGPG LVKPSQSLSL TCSVTGFSIS TSGYYWTWIR

QFPGKRLEWM GYINYGGGTS YNPSLKSRIS ITRDTSKNQF

LLHLNSVTTE DTATYCCATM ADRFAFFDVW GQGIQVTVSS

Anti-Human H7CR Clone 4.5
Light Chain Variable Region:
                                     (SEQ ID NO: 7)
DIVMTQSPSS LAVSAGEKVT ISCLSSQSLF SSNTKRNYLN

WYLQKPGQSP KLLIYHASTR LTGVPGRFIG SGSGTDFTLT

VSTVQAEDLG DYFCQQHYET PLTFGDGTRL EIK

Heavy Chain Variable Region:
                                     (SEQ ID NO: 8)
QIQLQESGPG LVKPSQSLSL TCSVTGFSIT TGGYYWNWIR

QFPGKKLEWM GYIYTSGRTS YNPSLKSRIS ITRDTSKNQF

FLQLNSMTTE DTATYYCADM ADKGGWFAYW GQGTLVTVSS

Anti-Human H7CR Clone 7.8
Light Chain Variable Region:
                                     (SEQ ID NO: 9)
DIVMTQSPSS LTVSAGEKVT ISCLSSQSLF SSNTNRNYLS

WYLQRPGQSP KLLIYHASTR LTGVPGRFIG SGSGTDFTLT

VSTVQAGDLG DYFCQQHYVT PLTFGDGTRL EIK

Heavy Chain Variable Region:
                                     (SEQ ID NO: 10)
QIQLQESGPG LVKPSQSLSL TCSVTGFSIT TGGYYWNWIR

QFPGKKLEWM GYIYSSGRTS YNPSLKSRIS ITRDTSKNQF

FLQLNSVTTE DTATYYCADM ADKGGWFDYW GQGTLVTVSS
```

(2) Consensus CDRs of the Anti-Human H7CR Antibodies

Analyses of the CDRs of the identified antibodies were conducted in order to identify consensus CDR sequences and likely variant CDR sequences that would provide similar binding attributes. Such variant CDRs were computed using Blosum62.iij analysis according to Table 1. Table 1 presents the Blosum62.iij substitution scores. The higher the score, the more conservative the substitution and thus the more likely the substitution will not affect function.

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | +4 | −1 | −2 | −2 | 0 | −1 | −1 | 0 | −2 | −1 | −1 | −1 | −1 | −2 | −1 | +1 | 0 | −3 | −2 | 0 |
| R | −1 | +5 | 0 | −2 | −3 | +1 | 0 | −2 | 0 | −3 | −2 | +2 | −1 | −3 | −2 | −1 | −1 | −3 | −2 | −3 |
| N | −2 | 0 | +6 | +1 | −3 | 0 | 0 | 0 | +1 | −3 | −3 | 0 | −2 | −3 | −2 | +1 | 0 | −4 | −2 | −3 |
| D | −2 | −2 | +1 | +6 | −3 | 0 | +2 | −1 | −1 | −3 | −4 | −1 | −3 | −3 | −1 | 0 | −1 | −4 | −3 | −3 |
| C | 0 | −3 | −3 | −3 | +9 | −3 | −4 | −3 | −3 | −1 | −1 | −3 | −1 | −2 | −3 | −1 | −1 | −2 | −2 | −1 |
| Q | −1 | +1 | 0 | 0 | −3 | +5 | +2 | −2 | 0 | −3 | −2 | +1 | 0 | −3 | −1 | 0 | −1 | −2 | −1 | −2 |
| E | −1 | 0 | 0 | +2 | −4 | +2 | +5 | −2 | 0 | −3 | −3 | +1 | −2 | −3 | −1 | 0 | −1 | −3 | −2 | −2 |
| G | 0 | −2 | 0 | −1 | −3 | −2 | −2 | +6 | −2 | −4 | −4 | −2 | −3 | −3 | −2 | 0 | −2 | −2 | −3 | −3 |
| H | −2 | 0 | +1 | −1 | −3 | 0 | 0 | −2 | +8 | −3 | −3 | −1 | −2 | −1 | −2 | −1 | −2 | −2 | +2 | −3 |
| I | −1 | −3 | −3 | −3 | −1 | −3 | −3 | −4 | −3 | +4 | +2 | −3 | +1 | 0 | −3 | −2 | −1 | −3 | −1 | +3 |
| L | −1 | −2 | −3 | −4 | −1 | −2 | −3 | −4 | −3 | +2 | +4 | −2 | +2 | 0 | −3 | −2 | −1 | −2 | −1 | +1 |
| K | −1 | +2 | 0 | −1 | −3 | +1 | +1 | −2 | −1 | −3 | −2 | +5 | −1 | −3 | −1 | 0 | −1 | −3 | −2 | −2 |
| M | −1 | −1 | −2 | −3 | −1 | 0 | −2 | −3 | −2 | +1 | +2 | −1 | +5 | 0 | −2 | −1 | −1 | −1 | −1 | +1 |
| F | −2 | −3 | −3 | −3 | −2 | −3 | −3 | −3 | −1 | 0 | 0 | −3 | 0 | +6 | −4 | −2 | −2 | +1 | +3 | −1 |
| P | −1 | −2 | −2 | −1 | −3 | −1 | −1 | −2 | −2 | −3 | −3 | −1 | −2 | −4 | +7 | −1 | −1 | −4 | −3 | −2 |
| S | +1 | −1 | +1 | 0 | −1 | 0 | 0 | 0 | −1 | −2 | −2 | 0 | −1 | −2 | −1 | +4 | +1 | −3 | −2 | −2 |
| T | 0 | −1 | 0 | −1 | −1 | −1 | −1 | −2 | −2 | −1 | −1 | −1 | −1 | −2 | −1 | +1 | +5 | −2 | −2 | 0 |
| W | −3 | −3 | −4 | −4 | −2 | −2 | −3 | −2 | −2 | −3 | −2 | −3 | −1 | +1 | −4 | −3 | −2 | +11 | +2 | −3 |
| Y | −2 | −2 | −2 | −3 | −2 | −1 | −2 | −3 | +2 | −1 | −1 | −2 | −1 | +3 | −3 | −2 | −2 | +2 | +7 | −1 |
| V | 0 | −3 | −3 | −3 | −1 | −2 | −2 | −3 | −3 | +3 | +1 | −2 | +1 | −1 | −2 | −2 | 0 | −3 | −1 | +4 |

Antibodies and antigen-binding fragments having 1, 2, 3, 4, 5 or 6 variant CDRs are disclosed. A substantial number of distinct CDRs were identified permitting the recognition of CDR residues that are likely to be required in any variant of a particular identified CDR. Such residues are shown in boldface in Table 2 and Table 3. For those residues that are found to vary among the compared CDRs, the substitution scores of Table 1 provide a method for determining the identities of permitted substitutions. For example, if a particular residue of a particular CDR is found to vary as R or S, then since R and S have a substitution score of −1, any substitution of R or S having a substitution score of −1 or greater are as likely as the observed variants (R or S) (or are more likely than R or S) to create a variant CDR having binding attributes that are sufficiently similar to those of the particular CDR to permit the variant CDR to be employed in lieu thereof so as to form a functional anti-H7CR antibody or antigen-binding fragment. For each position, the selection of a residue having a higher substitution score is preferred over the selection of a residue having a lower substitution score.

Table 2 presents an analysis of the light chain CDRs of the anti-H7CR antibodies and provides the consensus sequence of the observed and preferred variant light chain ("LC") anti-H7CR CDRs.

TABLE 2

Anti-H7CR Light Chain CDRs

Light Chain CDR1

| Antibody | Sequence | | | | | | | | | | | | SEQ ID NO |
|---|---|---|---|---|---|---|---|---|---|---|---|---|---|
| 1.3 | Q | S | L | F | S | S | N | T | N | R | N | Y | 29 |
| 4.5 | Q | S | L | F | S | S | N | T | K | R | N | Y | 30 |
| 7.8 | Q | S | L | F | S | S | N | T | N | R | N | Y | 29 |
| LC CDR1 Consensus Sequence: | Q | S | L | F | S | S | N | T | $\mathbf{X_1}$ | R | N | Y | 31 |

$\mathbf{X_1}$ is N or K or a substitution having an equal or greater substitution score (i.e., ≥0): R, N, Q, E, K, or S Light Chain CDR2

| Antibody | Sequence | | | SEQ ID NO |
|---|---|---|---|---|
| 1.3 | H | A | S | 32 |
| 4.5 | H | A | S | 32 |
| 7.8 | H | A | S | 32 |
| LC CDR2 Consensus Sequence: | H | A | S | 32 |

Light Chain CDR3

| Antibody | Sequence | | | | | | | | | SEQ ID NO |
|---|---|---|---|---|---|---|---|---|---|---|
| 1.3 | Q | H | H | Y | E | T | P | L | T | 45 |
| 4.5 | Q | Q | H | Y | E | T | P | L | T | 46 |
| 7.8 | Q | Q | H | Y | V | T | P | L | T | 47 |
| LC CDR3 Consensus Sequence: | Q | $\mathbf{X_1}$ | H | Y | $\mathbf{X_2}$ | T | P | L | T | 48 |

$\mathbf{X_1}$ is H or Q or a substitution having an equal or greater substitution score (i.e., ≥0): R, N, Q, E, or H $\mathbf{X_2}$ is E or V or a substitution having an equal or greater substitution score (i.e., ≥−2): A, Q, E, K, M, P, S, T, Y, or V Table 3 presents an analysis of the heavy chain CDRs of the anti-H7CR antibodies and provides the consensus sequence of the observed and preferred variant anti-H7CR heavy chain ("HC") CDRs.

immunospecific binding to H7CR. Additionally, the antibodies or fragments thereof can include a CDR that is at least 45%, at least 50%, at least 55%, at least 60%, at least 65%, at least 70%, at least 75%, at least 80%, at least 85%,

TABLE 3

Anti-H7CR Heavy Chain CDRs

Heavy Chain CDR1

| Antibody | | | | Sequence | | | | SEQ ID NO |
|---|---|---|---|---|---|---|---|---|
| 1.3 | G | F | S | I | S | T | S | G | 49 |
| 4.5 | G | F | S | I | T | T | G | G | 50 |
| 7.8 | G | F | S | I | T | T | G | G | 50 |
| HC CDR1 Consensus Sequence: | G | F | D | I | $X_1$ | T | $X_2$ | G | 51 |

$X_1$ is S or T or a substitution having an equal or greater substitution score (i.e., ≥+1): S or T
$X_2$ is S or G or a substitution having an equal or greater substitution score (i.e., ≥0): A, N, G, or S Heavy Chain CDR2

| Antibody | | | | Sequence | | | | SEQ ID NO |
|---|---|---|---|---|---|---|---|---|
| 1.3 | I | N | Y | G | G | G | T | 52 |
| 4.5 | I | Y | T | S | G | R | T | 53 |
| 7.8 | I | Y | S | S | G | R | T | 54 |
| HC CDR2 Consensus Sequence: | I | $X_1$ | $X_2$ | $X_3$ | G | $X_4$ | T | 55 |

$X_1$ is N or Y or a substitution having an equal or greater substitution score (i.e., ≥−2): A, R, N, Q, E, H, K, M, S, T, Y
$X_2$ is Y, T or S or a substitution having an equal or greater substitution score (i.e., ≥−2): A, R, N, C, Q, E, H, I, L, K, M, F, S, T, Y, or V
$X_3$ is S or G or a substitution having an equal or greater substitution score (i.e., ≥0): A, N, G, or S
$X_4$ is G or R or a substitution having an equal or greater substitution score (i.e., ≥−2): A, R, N, D, Q, E, G, H, K, P, S, or T Heavy Chain CDR3

| Antibody | | | | | Sequence | | | | | | | SEQ ID NO |
|---|---|---|---|---|---|---|---|---|---|---|---|---|
| 1.3 | A | T | M | A | D | R | F | A | F | F | D | V | 56 |
| 4.5 | A | D | M | A | D | K | G | G | W | F | A | Y | 57 |
| 7.8 | A | D | M | A | D | K | G | G | W | F | D | Y | 58 |
| HC CDR3 Consensus Sequence: | A | $X_1$ | M | A | D | $X_2$ | $X_3$ | $X_4$ | $X_5$ | F | $X_6$ | $X_7$ | 59 |

$X_1$ is T or D or a substitution having an equal or greater substitution score (i.e., ≥−1): N, D, Q, E, K, P, S, or T
$X_2$ is R or K or a substitution having an equal or greater substitution score (i.e., ≥+2): R, or K
$X_3$ is F or G or a substitution having an equal or greater substitution score (i.e., ≥−3): A, R, N, D, C, Q, E, G, H, K, M, F, S, T, W, Y, or V
$X_4$ is A or G or a substitution having an equal or greater substitution score (i.e., ≥0): A, G, or S
$X_5$ is F or W or a substitution having an equal or greater substitution score (i.e., ≥+1): F, W, or Y
$X_6$ is A or D or a substitution having an equal or greater substitution score (i.e., ≥−4): A, R, N, D, C, Q, E, G, H, I, L, K, M, F, P, S, T, W, Y, or V
$X_7$ is V or Y or a substitution having an equal or greater substitution score (i.e., ≥−2): A, R, N, D, Q, E, G, H, K, P, S, or T Thus, in addition to antibodies and antigen-binding fragments thereof that possess the CDRs of the anti-H7CR antibodies: 1.3, 4.5 and 7.8, antibodies and antigen-binding fragments thereof that possess CDRs having the above-described light and/or heavy chain consensus sequences are also provided.

The antibodies or fragments thereof include an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of the hamster monoclonal antibody produced by any of the above clones, and which exhibit at least 90%, at least 95%, or at least 99% identical to the amino acid sequence of a CDR of the above-listed clones and which exhibit immunospecific binding to H7CR. The determination of percent identity of two amino acid sequences can be determined by BLAST protein comparison.

In a specific embodiment, an antibody or an antigen-binding fragment thereof contains one, two, three, four, five, or more preferably, all 6 CDRs of the above-described preferred antibodies and will exhibit the ability to bind to human H7CR.

(3) Preferred Humanized Anti-Human H7CR Antibodies and their CDRs

Multiple preferred light and heavy chain humanized derivatives of anti-human H7CR antibodies 1.3 and 4.5 were prepared.

(a) Humanized Variants of Anti-Human H7CR Antibody 1.3

The amino acid sequences of the Light Chain Variable Region of preferred humanized variants of anti-human H7CR antibody 1.3, derived from the IGKV4-1*01 acceptor framework, are shown below (CDRs are shown underlined):

```
1. VL1A IGKV4-1*01 (Humanized 1):
                                        (SEQ ID NO: 17)
DIVMTQSPDS LAVSLGERAT INCKSSQSLF SSNTNRNYLA

WYQQKPGQPP KLLIYHASTR ESGVPDRFSG SGSGTDFTLT

ISSLQAEDVA VYYCQHHYET PLTFGQGTKL EIK

2. VL1B IGKV4-1*01 (Humanized 2):
                                        (SEQ ID NO: 18)
DIVMTQSPDS LAVSLGERAT INCKSSQSLF SSNTNRNYLN

WYQQKPGQSP KLLIYHASTR LSGVPDRFSG SGSGTDFTLT

ISSLQAEDVA DYYCQHHYET PLTFGDGTKL EIK

3. VL1C IGKV4-1*01 (Humanized 3):
                                        (SEQ ID NO: 19)
DIVMTQSPDS LAVSLGERAT INCLSSQSLF SSNTNRNYLN

WYLQKPGQSP KLLIYHASTR LSGVPDRFIG SGSGTDFTLT

ISSLQAEDVG DYYCQHHYET PLTFGDGTKL EIK
```

The amino acid sequences of the Light Chain Variable Region of preferred humanized variants of anti-human H7CR antibody 1.3 derived from the IGKV2D-28*01 acceptor framework, are shown below (CDRs are shown underlined):

```
1. VL2A IGKV2D-28*01 (Humanized 1):
                                        (SEQ ID NO: 20)
DIVMTQSPLS LPVTPGEPAS ISCRSSQSLF SSNTNRNYLD

WYLQKPGQSP QLLIYHASNR ASGVPDRFSG SGSGTDFTLK

ISRVEAEDVG VYYCQHHYET PLTFGDGTKL EIK

2. VL2B IGKV2D-28*01 (Humanized 2):
                                        (SEQ ID NO: 21)
DIVMTQSPLS LPVTPGEPAS ISCRSSQSLF SSNTNRNYLN

WYLQKPGQSP KLLIYHASTR ASGVPDRFSG SGSGTDFTLK

ISRVEAEDVG VYYCQHHYET PLTFGDGTKL EIK

3. VL2C IGKV2D-28*01 (Humanized 3):
                                        (SEQ ID NO: 22)
DIVMTQSPLS LPVTPGEPAS ISCLSSQSLF SSNTNRNYLN

WYLQKPGQSP KLLIYHASTR LSGVPDRFSG SGSGTDFTLK

ISRVEAEDVG DYYCQHHYET PLTFGDGTKL EIK
```

The amino acid sequences of the Heavy Chain Variable Region of preferred humanized variants of anti-human H7CR antibody 1.3 derived from the IGHV4-31*02 acceptor framework, are shown below (CDRs are shown underlined):

```
1. VH1A IGHV4-31*02 (Humanized 1):
                                        (SEQ ID NO: 23)
QVQLQESGPG LVKPSQTLSL TCTVSGFSIS TSGYYWSWIR

QHPGKGLEWI GYINYGGGTY YNPSLKSRVT ISVDTSKNQF

SLKLSSVTAA DTAVYYCATM ADRFAFFDVW GQGTMVTVSS

2. VH1B IGHV4-31*02 (Humanized 2):
                                        (SEQ ID NO: 24)
QVQLQESGPG LVKPSQTLSL TCTVSGFSIS TSGYYWSWIR

QHPGKRLEWI GYINYGGGTS YNPSLKSRVT ISRDTSKNQF

SLKLSSVTAA DTAVYYCATM ADRFAFFDVW GQGTMVTVSS

3. VH1C IGHV4-31*02 (Humanized 3):
                                        (SEQ ID NO: 25)
QVQLQESGPG LVKPSQTLSL TCTVSGFSIS TSGYYWSWIR

QFPGKRLEWM GYINYGGGTS YNPSLKSRVT ISRDTSKNQF

SLKLSSVTAA DTATYCCATM ADRFAFFDVW GQGTMVTVSS
```

The amino acid sequences of the Heavy Chain Variable Region of preferred humanized variants of anti-human H7CR antibody 1.3, derived from the AAY33199.1 acceptor framework, are shown below (CDRs are shown underlined):

```
1. VH2A AAY33199.1 (Humanized 1):
                                        (SEQ ID NO: 26)
QVQLQESGPG LVKPAQTLSL TCTVSGFSIS TSGYYWSWIR

QYPGKGLEWI GYINYGGGTY YNPSLKSRVT ISVDTSKNQF

SLKLTSVTAA DTAVYHCATM ADRFAFFDVW GQGTMVTVSS

2. VH2B AAY33199.1 (Humanized 2):
                                        (SEQ ID NO: 27)
QVQLQESGPG LVKPAQTLSL TCTVSGFSIS TSGYYWSWIR

QYPGKRLEWI GYINYGGGTS YNPSLKSRVT ISRDTSKNQF

SLKLTSVTAA DTATYCCATM ADRFAFFDVW GQGTMVTVSS

3. VH2C AAY33199.1 (Humanized 3):
                                        (SEQ ID NO: 28)
QVQLQESGPG LVKPAQTLSL TCTVSGFSIS TSGYYWSWIR

QFPGKRLEWM GYINYGGGTS YNPSLKSRVT ISRDTSKNQF

SLKLTSVTAA DTATYCCATM ADRFAFFDVW GQGTMVTVSS
```

The antibodies, and their antigen-binding fragments can include any of the 36 combinations of the above-described humanized variants of anti-human H7CR antibody 1.3. Specifically, such antibodies include the combinations shown in Table 4:

TABLE 4

Humanized Variants of anti-human H7CR Antibody 1.3

| Humanized Variant No. | Light Chain | SEQ ID NO. | Heavy Chain | SEQ ID NO. |
|---|---|---|---|---|
| 1 | VL1A IGKV4-1*01 (Humanized 1) | 17 | VH1A IGHV4-31*02 (Humanized 1) | 23 |
| 2 | VL1A IGKV4-1*01 (Humanized 1) | 17 | VH1B IGHV4-31*02 (Humanized 2): | 24 |
| 3 | VL1A IGKV4-1*01 (Humanized 1) | 17 | VH1C IGHV4-31*02 (Humanized 3) | 25 |
| 4 | VL1A IGKV4-1*01 (Humanized 1) | 17 | VH2A AAY33199.1 (Humanized 1) | 26 |
| 5 | VL1A IGKV4-1*01 (Humanized 1) | 17 | VH2B AAY33199.1 (Humanized 2) | 27 |
| 6 | VL1A IGKV4-1*01 (Humanized 1) | 17 | VH2C AAY33199.1 (Humanized 3) | 28 |

TABLE 4-continued

Humanized Variants of anti-human H7CR Antibody 1.3

| Humanized Variant No. | Light Chain | SEQ ID NO. | Heavy Chain | SEQ ID NO. |
|---|---|---|---|---|
| 7 | VL1B IGKV4-1*01 (Humanized 2) | 18 | VH1A IGHV4-31*02 (Humanized 1) | 23 |
| 8 | VL1B IGKV4-1*01 (Humanized 2) | 18 | VH1B IGHV4-31*02 (Humanized 2): | 24 |
| 9 | VL1B IGKV4-1*01 (Humanized 2) | 18 | VH1C IGHV4-31*02 (Humanized 3) | 25 |
| 10 | VL1B IGKV4-1*01 (Humanized 2) | 18 | VH2A AAY33199.1 (Humanized 1) | 26 |
| 11 | VL1B IGKV4-1*01 (Humanized 2) | 18 | VH2B AAY33199.1 (Humanized 2) | 27 |
| 12 | VL1B IGKV4-1*01 (Humanized 2) | 18 | VH2C AAY33199.1 (Humanized 3) | 28 |
| 13 | VL1C IGKV4-1*01 (Humanized 3) | 19 | VH1A IGHV4-31*02 (Humanized 1) | 23 |
| 14 | VL1C IGKV4-1*01 (Humanized 3) | 19 | VH1B IGHV4-31*02 (Humanized 2): | 24 |
| 15 | VL1C IGKV4-1*01 (Humanized 3) | 19 | VH1C IGHV4-31*02 (Humanized 3) | 25 |
| 16 | VL1C IGKV4-1*01 (Humanized 3) | 19 | VH2A AAY33199.1 (Humanized 1) | 26 |
| 17 | VL1C IGKV4-1*01 (Humanized 3) | 19 | VH2B AAY33199.1 (Humanized 2) | 27 |
| 18 | VL1C IGKV4-1*01 (Humanized 3) | 19 | VH2C AAY33199.1 (Humanized 3) | 28 |
| 19 | VL2A IGKV2D-28*01 (Humanized 1) | 20 | VH1A IGHV4-31*02 (Humanized 1) | 23 |
| 20 | VL2A IGKV2D-28*01 (Humanized 1) | 20 | VH1B IGHV4-31*02 (Humanized 2): | 24 |
| 21 | VL2A IGKV2D-28*01 (Humanized 1) | 20 | VH1C IGHV4-31*02 (Humanized 3) | 25 |
| 22 | VL2A IGKV2D-28*01 (Humanized 1) | 20 | VH2A AAY33199.1 (Humanized 1) | 26 |
| 23 | VL2A IGKV2D-28*01 (Humanized 1) | 20 | VH2B AAY33199.1 (Humanized 2) | 27 |
| 24 | VL2A IGKV2D-28*01 (Humanized 1) | 20 | VH2C AAY33199.1 (Humanized 3) | 28 |
| 25 | VL2B IGKV2D-28*01 (Humanized 2) | 21 | VH1A IGHV4-31*02 (Humanized 1) | 23 |
| 26 | VL2B IGKV2D-28*01 (Humanized 2) | 21 | VH1B IGHV4-31*02 (Humanized 2): | 24 |
| 27 | VL2B IGKV2D-28*01 (Humanized 2) | 21 | VH1C IGHV4-31*02 (Humanized 3) | 25 |
| 28 | VL2B IGKV2D-28*01 (Humanized 2) | 21 | VH2A AAY33199.1 (Humanized 1) | 26 |
| 29 | VL2B IGKV2D-28*01 (Humanized 2) | 21 | VH2B AAY33199.1 (Humanized 2) | 27 |
| 30 | VL2B IGKV2D-28*01 (Humanized 2) | 21 | VH2C AAY33199.1 (Humanized 3) | 28 |
| 31 | VL2C IGKV2D-28*01 (Humanized 3) | 22 | VH1A IGHV4-31*02 (Humanized 1) | 23 |
| 32 | VL2C IGKV2D-28*01 (Humanized 3) | 22 | VH1B IGHV4-31*02 (Humanized 2): | 24 |
| 33 | VL2C IGKV2D-28*01 (Humanized 3) | 22 | VH1C IGHV4-31*02 (Humanized 3) | 25 |
| 34 | VL2C IGKV2D-28*01 (Humanized 3) | 22 | VH2A AAY33199.1 (Humanized 1) | 26 |
| 35 | VL2C IGKV2D-28*01 (Humanized 3) | 22 | VH2B AAY33199.1 (Humanized 2) | 27 |
| 36 | VL2C IGKV2D-28*01 (Humanized 3) | 22 | VH2C AAY33199.1 (Humanized 3) | 28 |

(b) Humanized Variants of Anti-Human H7CR Antibody 4.5

The amino acid sequences of the Light Chain Variable Region of preferred humanized variants of anti-human H7CR antibody 4.5, derived from the IGKV4-1*01 acceptor framework, are shown below (CDRs are shown underlined):

1. VL1A IGKV4-1*01 (Humanized 1):
(SEQ ID NO: 33)
DIVMTQSPDS LAVSLGERAT INCKSS<u>QSLF SSNTKRNY</u>LA WYQQKPGQPP KLLIY<u>HAS</u>TR ESGVPDRFSG SGSGTDFTLT ISSLQAEDVA VYYC<u>QQHYET PLT</u>FGQGTRL EIK 2. VL1B IGKV4-1*01 (Humanized 2):
(SEQ ID NO: 34)
DIVMTQSPDS LAVSLGERAT INCKSS<u>QSLF SSNTKRNY</u>LN WYQQKPGQPP KLLIY<u>HAS</u>TR LSGVPDRFSG SGSGTDFTLT ISSLQAEDVA DYFC<u>QQHYET PLT</u>FGDGTRL EIK 3. VL1C IGKV4-1*01 (Humanized 3):
(SEQ ID NO: 35)
DIVMTQSPDS LAVSLGERAT INCLSS<u>QSLF SSNTKRNY</u>LN WYQQKPGQSP KLLIY<u>HAS</u>TR LSGVPDRFSG SGSGTDFTLT ISSLQAEDVA DYFC<u>QQHYET PLT</u>FGDGTRL EIK The amino acid sequences of the Light Chain Variable Region of preferred humanized variants of anti-human H7CR antibody 4.5, derived from the IGKV2D-40*01 acceptor framework, are shown below (CDRs are shown underlined):

1. VL2A IGKV2D-40*01 (Humanized 1):
(SEQ ID NO: 36)
DIVMTQTPLS LPVTPGEPAS ISCRSS<u>QSLF SSNTKRNY</u>LD WYLQKPGQSP QLLIY<u>HAS</u>YR ASGVPDRFSG SGSGTDFTLK ISRVEAEDVG VYYC<u>QQHYET PLT</u>FGQGTRL EIK 2. VL2B IGKV2D-40*01 (Humanized 2):
(SEQ ID NO: 37)
DIVMTQTPLS LPVTPGEPAS ISCRSS<u>QSLF SSNTKRNY</u>LN WYLQKPGQSP KLLIY<u>HAS</u>TR LSGVPDRFSG SGSGTDFTLK ISRVEAEDVG DYFC<u>QQHYET PLT</u>FGDGTRL EIK 3. VL2C IGKV2D-40*01 (Humanized 3):
(SEQ ID NO: 38)
DIVMTQTPSS LPVTPGEPAS ISCLSS<u>QSLF SSNTKRNY</u>LN WYLQKPGQSP KLLIY<u>HAS</u>TR LSGVPDRFSG SGSGTDFTLK ISRVEAEDVG DYFC<u>QQHYET PLT</u>FGDGTRL EIK The amino acid sequences of the Heavy Chain Variable Region of preferred humanized variants of anti-human H7CR antibody 1.3, derived from the IGHV4-31*02 acceptor framework, are shown below (CDRs are shown underlined):

1. VH1A IGHV4-31*02 (Humanized 1):
(SEQ ID NO: 39)
QVQLQESGPG LVKPSQTLSL TCTVS<u>GFSIT TGGYY</u>WSWIR QHPGKGLEWI GY<u>IYTSGRT</u>Y YNPSLKSRVT ISVDTSKNQF SLKLSSVTAA DTAVYYC<u>ADM ADKGGWFAY</u>W GQGTLVTVSS 2. VH1B IGHV4-31*02 (Humanized 2):
(SEQ ID NO: 40)
QVQLQESGPG LVKPSQTLSL TCTVS<u>GFSIT TGGYY</u>WNWIR QHPGKKLEWI GY<u>IYTSGRT</u>S YNPSLKSRVT ISRDTSKNQF -continued

```
SLKLSSVTAA DTAVYYCADM ADKGGWFAYW GQGTLVTVSS

3. VH1C IGHV4-31*02 (Humanized 3):
                                      (SEQ ID NO: 41)
QVQLQESGPG LVKPSQTLSL TCTVSGFSIT TGGYYWNWIR

QFPGKKLEWM GYIYTSGRTS YNPSLKSRVT ISRDTSKNQF

SLKLSSVTAA DTAVYYCADM ADKGGWFAYW GQGTLVTVSS
```

The amino acid sequences of the Heavy Chain Variable Region of preferred humanized variants of anti-human H7CR antibody 1.3, derived from the IGHV2-5*01 acceptor framework, are shown below (CDRs are shown underlined):

```
1. VH2A IGHV2-5*01 (Humanized 1):
                                      (SEQ ID NO: 42)
QITLKESGPT LVKPTQTLTL TCTFSGFSIT TGGYYVGWIR

QPPGKALEWL ALIYTSGRTR YSPSLKSRLT ITKDTSKNQV

VLTMTNMDPV DTATYYCADM ADKGGWFAYW GQGTLVTVSS

2. VH2B IGHV2-5*01 (Humanized 2):
                                      (SEQ ID NO: 43)
QITLKESGPT LVKPTQTLTL TCTVSGFSIT TGGYYWNWIR

QPPGKKLEWL ALIYTSGRTS YNPSLKSRLT ITKDTSKNQV

VLTMTNMDPV DTATYYCADM ADKGGWFAYW GQGTLVTVSS

3. VH2C IGHV2-5*01 (Humanized 3):
                                      (SEQ ID NO: 44)
QIQLKESGPT LVKPTQTLTL TCTVSGFSIT TGGYYWNWIR

QPPGKKLEWM ALIYTSGRTS YNPSLKSRLT ITKDTSKNQV

VLTMTNMDPV DTATYYCADM ADKGGWFAYW GQGTLVTVSS
```

The antibodies, and their antigen-binding fragments can include any of the 36 combinations of the above-described humanized variants of anti-human H7CR antibody 4.5. Specifically, such antibodies include the combinations shown in Table 5:

TABLE 5

Humanized Variants of anti-human H7CR Antibody 4.5

| Humanized Variant No. | Light Chain | SEQ ID NO. | Heavy Chain | SEQ ID NO. |
|---|---|---|---|---|
| 1 | VL1A IGKV4-1*01 (Humanized 1) | 33 | VH1A IGHV4-31*02 (Humanized 1) | 39 |
| 2 | VL1A IGKV4-1*01 (Humanized 1) | 33 | VH1B IGHV4-31*02 (Humanized 2): | 40 |
| 3 | VL1A IGKV4-1*01 (Humanized 1) | 33 | VH1C IGHV4-31*02 (Humanized 3) | 41 |
| 4 | VL1A IGKV4-1*01 (Humanized 1) | 33 | VH2A IGHV2-5*01 (Humanized 1) | 42 |
| 5 | VL1A IGKV4-1*01 (Humanized 1) | 33 | VH2B IGHV2-5*01 (Humanized 2) | 43 |
| 6 | VL1A IGKV4-1*01 (Humanized 1) | 33 | VH2C IGHV2-5*01 (Humanized 3) | 44 |
| 7 | VL1B IGKV4-1*01 (Humanized 2) | 34 | VH1A IGHV4-31*02 (Humanized 1) | 39 |
| 8 | VL1B IGKV4-1*01 (Humanized 2) | 34 | VH1B IGHV4-31*02 (Humanized 2): | 40 |
| 9 | VL1B IGKV4-1*01 (Humanized 2) | 34 | VH1C IGHV4-31*02 (Humanized 3) | 41 |
| 10 | VL1B IGKV4-1*01 (Humanized 2) | 34 | VH2A IGHV2-5*01 (Humanized 1) | 42 |
| 11 | VL1B IGKV4-1*01 (Humanized 2) | 34 | VH2B IGHV2-5*01 (Humanized 2) | 43 |
| 12 | VL1B IGKV4-1*01 (Humanized 2) | 34 | VH2C IGHV2-5*01 (Humanized 3) | 44 |
| 13 | VL1C IGKV4-1*01 (Humanized 3) | 35 | VH1A IGHV4-31*02 (Humanized 1) | 39 |
| 14 | VL1C IGKV4-1*01 (Humanized 3) | 35 | VH1B IGHV4-31*02 (Humanized 2): | 40 |
| 15 | VL1C IGKV4-1*01 (Humanized 3) | 35 | VH1C IGHV4-31*02 (Humanized 3) | 41 |
| 16 | VL1C IGKV4-1*01 (Humanized 3) | 35 | VH2A IGHV2-5*01 (Humanized 1) | 42 |
| 17 | VL1C IGKV4-1*01 (Humanized 3) | 35 | VH2B IGHV2-5*01 (Humanized 2) | 43 |
| 18 | VL1C IGKV4-1*01 (Humanized 3) | 35 | VH2C IGHV2-5*01 (Humanized 3) | 44 |
| 19 | VL2A IGKV2D-40*01 (Humanized 1) | 36 | VH1A IGHV4-31*02 (Humanized 1) | 39 |
| 20 | VL2A IGKV2D-40*01 (Humanized 1) | 36 | VH1B IGHV4-31*02 (Humanized 2): | 40 |
| 21 | VL2A IGKV2D-40*01 (Humanized 1) | 36 | VH1C IGHV4-31*02 (Humanized 3) | 41 |
| 22 | VL2A IGKV2D-40*01 (Humanized 1) | 36 | VH2A IGHV2-5*01 (Humanized 1) | 42 |
| 23 | VL2A IGKV2D-40*01 (Humanized 1) | 36 | VH2B IGHV2-5*01 (Humanized 2) | 43 |
| 24 | VL2A IGKV2D-40*01 (Humanized 1) | 36 | VH2C IGHV2-5*01 (Humanized 3) | 44 |
| 25 | VL2B IGKV2D-40*01 (Humanized 2) | 37 | VH1A IGHV4-31*02 (Humanized 1) | 39 |
| 26 | VL2B IGKV2D-40*01 (Humanized 2) | 37 | VH1B IGHV4-31*02 (Humanized 2): | 40 |
| 27 | VL2B IGKV2D-40*01 (Humanized 2) | 37 | VH1C IGHV4-31*02 (Humanized 3) | 41 |
| 28 | VL2B IGKV2D-40*01 (Humanized 2) | 37 | VH2A IGHV2-5*01 (Humanized 1) | 42 |
| 29 | VL2B IGKV2D-40*01 (Humanized 2) | 37 | VH2B IGHV2-5*01 (Humanized 2) | 43 |
| 30 | VL2B IGKV2D-40*01 (Humanized 2) | 37 | VH2C IGHV2-5*01 (Humanized 3) | 44 |
| 31 | VL2C IGKV2D-40*01 (Humanized 3) | 38 | VH1A IGHV4-31*02 (Humanized 1) | 39 |
| 32 | VL2C IGKV2D-40*01 (Humanized 3) | 38 | VH1B IGHV4-31*02 (Humanized 2): | 40 |
| 33 | VL2C IGKV2D-40*01 (Humanized 3) | 38 | VH1C IGHV4-31*02 (Humanized 3) | 41 |
| 34 | VL2C IGKV2D-40*01 (Humanized 3) | 38 | VH2A IGHV2-5*01 (Humanized 1) | 42 |
| 35 | VL2C IGKV2D-40*01 (Humanized 3) | 38 | VH2B IGHV2-5*01 (Humanized 2) | 43 |
| 36 | VL2C IGKV2D-40*01 (Humanized 3) | 38 | VH2C IGHV2-5*01 (Humanized 3) | 44 |

The disclosed antibodies or fragments thereof include an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of the mouse monoclonal antibody produced by any of the above clones, and which exhibit immunospecific binding to human H7CR. Other antibodies or fragments thereof include a CDR that is at least 45%, at least 50%, at least 55%, at least 60%, at least 65%, at least 70%, at least 75%, at least 80%, at least 85%, at least 90%, at least 95%, or at least 99% identical to the amino acid sequence of a CDR of the above-listed clones and which exhibit immunospecific binding to H7CR. The determination of percent identity of two amino acid sequences can be determined by BLAST protein comparison.

In a preferred embodiment, the antibody is a humanized immunoglobulin molecule (e.g., an antibody, diabody, fusion protein, etc.) that includes one, two or three light chain CDRs and one, two or three heavy chain CDRs (most preferably three light chain CDRs and three heavy chain CDRs), wherein the light chain CDRs include:
(1) the light chain CDR1 of a humanized variant of anti-human H7CR antibody 1.3;
(2) the light chain CDR2 of a humanized variant of anti-human H7CR antibody 4.5;
(3) the light chain CDR3 of a humanized variant of anti-human H7CR antibody 7.8;
(4) the light chain CDR1 and the light chain CDR2 of a humanized variant of anti-human H7CR antibody 1.3, 4.5 or 7.8;
(5) the light chain CDR1 and the light chain CDR3 of a humanized variant of anti-human H7CR antibody 1.3, 4.5 or 7.8;
(6) the light chain CDR2 and the light chain CDR3 of a humanized variant of anti-human H7CR antibody 1.3, 4.5 or 7.8;
or
(7) the light chain CDR1, the light chain CDR2 and the light chain CDR3 of a humanized variant of anti-human H7CR antibody 1.3, 4.5 or 7.8.

In an alternative preferred embodiment, the humanized immunoglobulin molecule includes one, two or three light chain CDRs and one, two or three heavy chain CDRs (most preferably three light chain CDRs and three heavy chain CDRs), wherein the heavy chain CDRs include:
(1) the heavy chain CDR1 of a humanized variant of anti-human H7CR antibody 1.3;
(2) the heavy chain CDR2 of a humanized variant of anti-human H7CR antibody 4.5;
(3) the heavy chain CDR3 of a humanized variant of anti-human H7CR antibody 7.8;
(4) the heavy chain CDR1 and the heavy chain CDR2 of a humanized variant of anti-human H7CR antibody 1.3, 4.5 or 7.8;
(5) the heavy chain CDR1 and the heavy chain CDR3 of a humanized variant of anti-human H7CR antibody 1.3, 4.5 or 7.8;
(6) the heavy chain CDR2 and the heavy chain CDR3 of a humanized variant of anti-human H7CR antibody 1.3, 4.5 or 7.8;
or
(7) the heavy chain CDR1, the heavy chain CDR2 and the heavy chain CDR3 of a humanized variant of anti-human H7CR antibody 1.3, 4.5 or 7.8.

In a particularly preferred embodiment, the antibody is a humanized immunoglobulin molecule that includes one, two or three light chain CDRs and one, two or three heavy chain CDRs (most preferably three light chain CDRs and three heavy chain CDRs), wherein the light chain CDRs include:
(1) the light chain CDR1 of a humanized variant of anti-human H7CR antibody 1.3;
(2) the light chain CDR2 of a humanized variant of anti-human H7CR antibody 4.5;
(3) the light chain CDR3 of a humanized variant of anti-human H7CR antibody 7.8;
(4) the light chain CDR1 and the light chain CDR2 of a humanized variant of anti-human H7CR antibody 1.3, 4.5 or 7.8;
(5) the light chain CDR1 and the light chain CDR3 of a humanized variant of anti-human H7CR antibody 1.3, 4.5 or 7.8;
(6) the light chain CDR2 and the light chain CDR3 of a humanized variant of anti-human H7CR antibody 1.3, 4.5 or 7.8;
or
(7) the light chain CDR1, the light chain CDR2 and the light chain CDR3 of a humanized variant of anti-human H7CR antibody 1.3, 4.5 or 7.8,
and wherein the heavy chain CDRs include:
(1) the heavy chain CDR1 of a humanized variant of anti-human H7CR antibody 1.3;
(2) the heavy chain CDR2 of a humanized variant of anti-human H7CR antibody 4.5;
(3) the heavy chain CDR3 of a humanized variant of anti-human H7CR antibody 7.8;
(4) the heavy chain CDR1 and the heavy chain CDR2 of a humanized variant of anti-human H7CR antibody 1.3, 4.5 or 7.8;
(5) the heavy chain CDR1 and the heavy chain CDR3 of a humanized variant of anti-human H7CR antibody 1.3, 4.5 or 7.8;
(6) the heavy chain CDR2 and the heavy chain CDR3 of a humanized variant of anti-human H7CR antibody 1.3, 4.5 or 7.8;
or
(7) the heavy chain CDR1, the heavy chain CDR2 and the heavy chain CDR3 of a humanized variant of anti-human H7CR antibody 1.3, 4.5 or 7.8.

Most preferably, such CDRs shall be of the same humanized variant of anti-human H7CR antibody 1.3, 4.5 or 7.8, respectively.

In a specific embodiment, an antibody or an antigen-binding fragment will include one, two, three, four, five, or more preferably, all 6 CDRs of the humanized variants of anti-human H7CR antibody 1.3, 4.5 or 7.8 and will exhibit the same ability to bind to human H7CR as the parental antibody.

E. Therapeutic and Prophylactic Uses of the Preferred Compositions

As used herein, the terms "treat," "treating," "treatment" and "therapeutic use" refer to the elimination, reduction or amelioration of one or more symptoms of a disease or disorder that would benefit from an increased or decreased immune response. As used herein, a "therapeutically effective amount" refers to that amount of a therapeutic agent sufficient to mediate an altered immune response, and more preferably, a clinically relevant altered immune response, sufficient to mediate a reduction or amelioration of a symptom of a disease or condition. An effect is clinically relevant if its magnitude is sufficient to impact the health or prognosis of a recipient subject. A therapeutically effective amount may refer to the amount of therapeutic agent sufficient to reduce or minimize disease progression, e.g., delay or minimize the spread of cancer. A therapeutically effective amount may also refer to the amount of the therapeutic agent that provides a therapeutic benefit in the treatment or management of a disease. Further, a therapeutically effective amount with respect to a therapeutic agent means that amount of therapeutic agent alone, or in combination with other therapies, that provides a therapeutic benefit in the treatment or management of a disease, e.g., sufficient to enhance the therapeutic efficacy of a therapeutic antibody sufficient to treat or manage a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease. Further, a prophylactically effective amount with respect to a prophylactic agent means that amount of prophylactic agent alone, or in combination with other agents, that provides a prophylactic benefit in the prevention of disease.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight, response, and the past medical history of the patient. Suitable regimens can be selected by one skilled in the art by considering such factors and by following, for example, dosages reported in the literature and recommended in the *Physician's Desk Reference* (56th Ed., 2002).

1. Uses of Up-Modulators of the Immune System

One embodiment concerns H7CR-binding molecules, such as anti-H7CR antibodies (and fragments of such antibodies that bind to H7CR) or B7-H7 Ig, that, by binding to H7CR agonize (i.e., enhance) T cell proliferation and/or cytokine production. The administration of such molecules to a subject up-modulates the immune system of the subject. As H7CR expression is associated with a naïve T cell phenotype, administration of such molecules would be effective for increasing T cell priming and activation and thus would be good to combine with vaccines. Furthermore, agonistic anti-H7CR (and B7-H7 Ig) would be very good to combine with molecules that target immune-checkpoints and inhibit receptors that would normally dampen the immune response: anti-PD-1, anti-B7-H1, anti-CTLA4 etc. Such antibodies may be better administered in sequence, i.e., anti-H7CR first to enhance T cell priming, followed by e.g., anti-PD-1 to prevent T cell exhaustion. Bi-specific molecules targeting H7CR and immune-checkpoint blockade are also contemplated.

Up-modulation of the immune system is particularly desirable in the treatment of cancers and chronic infections (e.g., HIV infection, AIDS, etc.) and thus the disclosed molecules have utility in the treatment of such disorders. Macrophages have been shown to contribute significantly to the initial steps of HIV infection (Carter, C. A. et al. (2008) "*Cell Biology Of HIV-1 Infection Of Macrophages,*" Ann. Rev. Microbiol. 62:425-443; Noursadeghi, M. et al. (2006) "*HIV-1 Infection Of Mononuclear Phagocytic Cells: The Case For Bacterial Innate Immune Deficiency In AIDS,*" Lancet Infect. Dis. 6:794-804). Accordingly antibodies (particularly if conjugated to a toxin) that bind B7-H7 have utility in preventing or treating HIV infection.

As used herein, the term "cancer" refers to a neoplasm or tumor resulting from abnormal uncontrolled growth of cells. As used herein, cancer explicitly includes leukemias and lymphomas. The term refers to a disease involving cells that have the potential to metastasize to distal sites and exhibit phenotypic traits that differ from those of non-cancer cells, for example, formation of colonies in a three-dimensional substrate such as soft agar or the formation of tubular networks or weblike matrices in a three-dimensional basement membrane or extracellular matrix preparation. Non-cancer cells do not form colonies in soft agar and form distinct sphere-like structures in three-dimensional basement membrane or extracellular matrix preparations.

Cancers and related disorders that can be treated or prevented include, but are not limited to, the following: leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease, non-Hodgkin's disease; multiple myelomas such as, but not limited to, smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including, but not limited to, ocular melanoma such as iris melanoma, choroidal melanoma, and cilliary body melanoma, and retinoblastoma; vaginal cancers, including, but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

Accordingly, the disclosed methods and compositions are also useful in the treatment, inhibition or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosafcoma, rhabdomyoscarama, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the disclosed methods and compositions. Such cancers may include, but are not limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the disclosed methods and compositions in the ovary, bladder, breast, colon, lung, skin, pancreas, or uterus.

In other specific embodiments, sarcoma, melanoma, or leukemia is treated or prevented by the disclosed methods and compositions.

Cancer cells acquire a characteristic set of functional capabilities during their development, albeit through various mechanisms. Such capabilities include evading apoptosis, self-sufficiency in growth signals, insensitivity to antigrowth signals, tissue invasion/metastasis, limitless explicative potential, and sustained angiogenesis. The term "cancer cell" is meant to encompass both pre-malignant and malignant cancer cells. In some embodiments, cancer refers to a benign tumor, which has remained localized. In other embodiments, cancer refers to a malignant tumor, which has invaded and destroyed neighboring body structures and spread to distant sites. In yet other embodiments, the cancer is associated with a specific cancer antigen (e.g., pan-carcinoma antigen (KS 1/4), ovarian carcinoma antigen (CA125), prostate specific antigen (PSA), carcinoembryonic antigen (CEA), CD19, CD20, HER2/neu, etc.).

Similar to its application to tumors as discussed above, the disclosed antibodies and antigen-binding fragments can be used alone, or as an adjuvant, in combination with vaccines or with antimicrobial agents, to stimulate the immune response against toxins or self-antigens or against pathogens (e.g., viruses, such as HIV, HTLV, hepatitis virus, influenza virus, respiratory syncytial virus, vaccinia virus, rabies virus; bacteria, such as those of *Mycobacteria, Staphylococci, Streptococci, Pneumonococci, Meningococci, Conococci, Klebsiella, Proteus, Serratia, Pseudomonas, Legionella, Corynebacteria, Salmonella, Vibrio, Clostridia, Bacilli, Pasteurella, Leptospirosis, Bordatella*, and particularly such pathogens associated with cholera, tetanus, botulism, anthrax, plague, and Lyme disease; or fungal or parasitic pathogens, such as *Candida* (*albicans, krusei, glabrata, tropicalis*, etc.), *Cryptococcus, Aspergillus* (*fumigatus, niger*, etc.), Genus *Mucorales* (*mucor, absidia, rhizophus*), *Sporothrix* (*schenkii*), *Blastomyces* (*dermatitidis*), *Paracoccidioides* (*brasiliensis*), *Coccidioides* (*immitis*) and *Histoplasma* (*capsulatum*), *Entamoeba, histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Toxoplasma gondi*, etc.)., *Sporothrix, Blastomyces, Paracoccidioides, Coccidioides, Histoplasma, Entamoeba, Histolytica, Balantidium, Naegleria, Acanthamoeba, Giardia, Cryptosporidium, Pneumocystis, Plasmodium, Babesia*, or *Trypanosoma*, etc. Thus, the antibodies and antigen-binding fragments have utility in the treatment of infectious disease.

Another use of the antibodies and antigen-binding fragments is to block or deplete T cells in patients having T cell cancers. In one embodiment such blockage or depletion is accomplished using anti-H7CR antibodies that bind to a site proximal to the binding site of H7CR to its ligand, such that normal H7CR function is impaired or disrupted. As a consequence of such disruption the effective (functional) concentration of T cells is depleted. In a preferred embodiment, such depletion is accomplished using anti-H7CR antibodies that are conjugated to a toxin, such that their binding to a T cell leads to the death of the cell. Preferably, in either embodiment, the sequence of the Fc region of the antibody will have been deleted (for example, an Fab or F(ab)$_2$, etc.) or modified so that the molecule will exhibit diminished or no Fc receptor (FcR) binding activity, or will exhibit enhanced antibody-dependent cell-mediated cytotoxicity (ADCC) or complement dependent cytotoxicity (CDC) activities.

2. Uses of Down-Modulators of the Immune System

An alternative embodiment relates to molecules, such as anti-B7-H7 antibodies (and fragments of such antibodies that bind to B7-H7 or H7CR Ig, that, by binding to B7-H7 antagonize (i.e., attenuate or impair) H7CR function and T cell proliferation and/or cytokine production. The administration of such molecules to a subject down-modulates the immune system of the subject, and is particularly useful for the treatment of inflammation or autoimmunity.

Another embodiment provides antibodies that bind to H7CR and block ligand interaction with H7CR and do not agonize H7CR.

Down-modulation of the immune system is desirable in the treatment of inflammatory and auto-immune diseases. Examples of autoimmune disorders that may be treated by administering the antibodies include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, Neuromyelitis optica (NMO), type 1 or immune-mediated diabetes mellitus, myasthenia gravis, *pemphigus vulgaris*, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis.

Examples of inflammatory disorders which can be prevented, treated or managed include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacterial infections.

The described anti-H7CR antibodies may be employed to produce anti-idiotypic peptides or antibodies (Wallmann, J. et al. (2010) "*Anti-Ids in Allergy: Timeliness of a Classic Concept*," World Allergy Organiz. J. 3(6):195-201; Nardi, M. et al. (2000) "*Antiidiotype Antibody Against Platelet Anti-GpIIIa Contributes To The Regulation Of Thrombocytopenia In HIV-1-ITP Patients*," J. Exp. Med. 191(12):2093-2100) or mimetics (Zang, Y. C. et al. (2003) "*Human Anti-Idiotypic T Cells Induced By TCR Peptides Corresponding To A Common CDR3 Sequence Motif In Myelin Basic Protein-Reactive T Cells*," Int. Immunol. 15(9):1073-1080; Loiarro, M. et al. (Epub 2010 Apr. 8) "*Targeting TLR/IL-1R Signalling In Human Diseases*," Mediators Inflamm. 2010:674363) of H7CR. Such molecules serve as surrogates for H7CR, and thus their administration to a subject down-modulates the immune system of such subject by engaging the B7-H7 ligand and preventing it from binding the endogenous H7CR receptor. Such molecules have utility in the treatment of graft vs. host disease. Similarly, agonist antibodies that enhance binding between such antibodies and such receptor/ligand have utility as agonists of H7CR signaling and thus have utility in the treatment of inflammation and autoimmune disease.

Thus, the antibodies and antigen-binding fragments have utility in the treatment of inflammatory and auto-immune diseases.

F. Methods of Administration

Various delivery systems are known and can be used to administer the therapeutic or prophylactic compositions described herein, e.g., encapsulation in liposomes, microparticles, microcapsules, recombinant cells capable of expressing the antibody or fusion protein, receptor-mediated endocytosis (see, e.g., Wu and Wu, 1987, *J. Biol. Chem.* 262: 4429-4432), construction of a nucleic acid as part of a retroviral or other vector, etc.

Methods of administering a humanized antibody include, but are not limited to, parenteral administration (e.g., intradermal, intramuscular, intraperitoneal, intravenous and subcutaneous), epidural, and mucosal (e.g., intranasal and oral routes). In a specific embodiment, the disclosed antibodies are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903. In a specific embodiment, it may be desirable to administer the pharmaceutical compositions locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering one or more of the disclosed antibodies, care must be taken to use materials to which the antibody or the fusion protein does not absorb.

In some embodiments, the humanized or chimeric antibodies are formulated in liposomes for targeted delivery of the disclosed antibodies. Liposomes are vesicles composed of concentrically ordered phopsholipid bilayers which encapsulate an aqueous phase. Liposomes typically include various types of lipids, phospholipids, and/or surfactants. The components of liposomes are arranged in a bilayer configuration, similar to the lipid arrangement of biological membranes. Liposomes are particularly preferred delivery vehicles due, in part, to their biocompatibility, low immunogenicity, and low toxicity. Methods for preparation of liposomes are known in the art, see, e.g., Epstein et al., 1985, Proc. Natl. Acad. Sci. USA, 82: 3688; Hwang et al., 1980 Proc. Natl. Acad. Sci. USA, 77: 4030-4; U.S. Pat. Nos. 4,485,045 and 4,544,545.

Methods of preparing liposomes with a prolonged serum half-life, i.e., enhanced circulation time, such as those disclosed in U.S. Pat. No. 5,013,556 can be used to produce antibody formulations. Preferred liposomes used in the disclosed methods are not rapidly cleared from circulation, i.e., are not taken up into the mononuclear phagocyte system (MPS). The liposomes include sterically stabilized liposomes which are prepared using common methods known to one skilled in the art. Although not intending to be bound by a particular mechanism of action, sterically stabilized liposomes contain lipid components with bulky and highly flexible hydrophilic moieties, which reduces the unwanted reaction of liposomes with serum proteins, reduces oposonization with serum components and reduces recognition by MPS. Sterically stabilized liposomes are preferably prepared using polyethylene glycol. For preparation of liposomes and sterically stabilized liposome, see, e.g., Bendas et al., 2001 *BioDrugs,* 15(4): 215-224; Allen et al., 1987 *FEBS Lett.* 223: 42-6; Klibanov et al., 1990 *FEBS Lett.,* 268: 235-7; Blum et al., 1990, *Biochim. Biophys. Acta.,* 1029: 91-7; Torchilin et al., 1996, *J. Liposome Res.* 6: 99-116; Litzinger et al., 1994, *Biochim. Biophys. Acta,* 1190: 99-107; Maruyama et al., 1991, *Chem. Pharm. Bull.,* 39: 1620-2; Klibanov et al., 1991, *Biochim Biophys Acta,* 1062; 142-8; Allen et al., 1994, *Adv. Drug Deliv. Rev,* 13: 285-309. Liposomes that are adapted for specific organ targeting, see, e.g., U.S. Pat. No. 4,544,545, or specific cell targeting, see, e.g., U.S. Patent Application Publication No. 2005/0074403 can also be used. Particularly useful liposomes for use in the compositions and methods can be generated by reverse phase evaporation method with a lipid composition including phosphatidylcholine, cholesterol, and PEG derivatized phosphatidylethanolamine (PEG-PE). Liposomes are extruded through filters of defined pore size to yield liposomes with the desired diameter. In some embodiments, a fragment of an antibody, e.g., F(ab'), may be conjugated to the liposomes using previously described methods, see, e.g., Martin et al., 1982, *J. Biol. Chem.* 257: 286-288.

The humanized or chimeric antibodies may also be formulated as immunoliposomes. Immunoliposomes refer to a liposomal composition, wherein an antibody or a fragment thereof is linked, covalently or non-covalently to the liposomal surface. The chemistry of linking an antibody to the liposomal surface is known in the art, see, e.g., U.S. Pat. No. 6,787,153; Allen et al., 1995, Stealth Liposomes, Boca Rotan: CRC Press, 233-44; Hansen et al., 1995, *Biochim. Biophys. Acta,* 1239: 133-144.

The humanized or chimeric antibodies can be packaged in a hermetically sealed container, such as an ampoule or sachette, indicating the quantity of antibody. In one embodiment, the antibodies are supplied as a dry sterilized lyophilized powder or water free concentrate in a hermetically sealed container and can be reconstituted, e.g., with water or saline to the appropriate concentration for administration to a subject. Preferably, the antibodies are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized antibodies should be stored at between 2 and 8° C. in their original container and the antibodies should be administered within 12 hours, preferably within 6 hours, within 5 hours, within 3 hours, or within 1 hour after being reconstituted. In an alternative embodiment, antibodies are supplied in liquid form in a hermetically sealed container indicating the quantity and concentration of the antibody, fusion protein, or conjugated molecule. Preferably, the liquid form of the antibodies are supplied in a hermetically sealed container at least 1 mg/ml, more preferably at least 2.5 mg/ml, at least 5 mg/ml, at least 8 mg/ml, at least 10 mg/ml, at least 15 mg/kg, at least 25 mg/ml, at least 50 mg/ml, at least 100 mg/ml, at least 150 mg/ml, at least 200 mg/ml of the antibodies.

The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems. For the disclosed antibodies, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies or fragments thereof may be reduced by enhancing uptake and tissue penetration of the antibodies by modifications such as, for example, lipidation.

In yet another embodiment, the compositions can be delivered in a controlled release or sustained release system. Any technique known to one of skill in the art can be used to produce sustained release formulations including one or more antibodies. See, e.g., U.S. Pat. No. 4,526,938; PCT publication WO 91/05548; PCT publication WO 96/20698; Ning et al., 1996, "Intratumoral Radioimmunotheraphy of a Human Colon Cancer Xenograft Using a Sustained-Release Gel," *Radiotherapy & Oncology* 39:179-189, Song et al., 1995, "Antibody Mediated Lung Targeting of Long-Circulating Emulsions," *PDA Journal of Pharmaceutical Science & Technology* 50:372-397; Cleek et al., 1997, "Biodegradable Polymeric Carriers for a bFGF Antibody for Cardiovascular Application," *Pro. Int'l. Symp. Control. Rel. Bioact. Mater.* 24:853-854; and Lam et al., 1997, "Microencapsulation of Recombinant Humanized Monoclonal Antibody for Local Delivery," *Proc. Int'l. Symp. Control Rel. Bioact. Mater.* 24:759-760. In one embodiment, a pump may be used in a controlled release system (See Langer, supra; Sefton, 1987, *CRC Crit. Ref Biomed. Eng.* 14:20; Buchwald et al., 1980, Surgery 88:507; and Saudek et al., 1989, *N Engl. J. Med.* 321:574). In another embodiment, polymeric materials can be used to achieve controlled release of antibodies (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J., Macromol. Sci. Rev. Macromol. Chem.* 23:61; See also Levy et al., 1985, *Science* 228:190; During et al., 1989, Ann. Neurol. 25:351; Howard et al., 1989, *J. Neurosurg.* 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-coglycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)). In another embodiment, polymeric compositions useful as controlled release implants are used according to Dunn et al. (See U.S. Pat. No. 5,945,155). This particular method is based upon the therapeutic effect of the in situ controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533). Controlled release systems are discussed in the review by Langer (1990, *Science* 249:1527-1533). Any technique known to one of skill in the art can be used to produce sustained release formulations including one or more therapeutic agents. See, e.g., U.S. Pat. No. 4,526,938; International Publication Nos. WO 91/05548 and WO 96/20698; Ning et al., 1996, *Radiotherapy & Oncology* 39:179-189; Song et al., 1995, *PDA Journal of Pharmaceutical Science* & Technology 50:372-397; Cleek et al., 1997, *Pro. Int'l. Symp. Control. Rel. Bioact. Mater.* 24:853-854; and Lam et al., 1997, *Proc. Int'l. Symp. Control Rel. Bioact. Mater.* 24:759-760.

In a specific embodiment wherein the therapeutic or prophylactic composition is a nucleic acid encoding a disclosed antibody or an antigen-binding fragment thereof, the nucleic acid can be administered in vivo to promote expression of its encoded antibody, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, Proc. Natl. Acad. Sci. USA 88:1864-1868), etc. Alternatively, a nucleic acid can be introduced intracellularly and incorporated within host cell DNA for expression by homologous recombination.

Treatment of a subject with a therapeutically or prophylactically effective amount of the disclosed antibodies can include a single treatment or, preferably, can include a series of treatments.

G. Pharmaceutical Compositions

The disclosed compositions can include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions can include a prophylactically or therapeutically effective amount of a prophylactic and/or therapeutic agent disclosed herein or a combination of those agents and a pharmaceutically acceptable carrier. Preferably, the compositions include a prophylactically or therapeutically effective amount of humanized antibodies and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions can be supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions can be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

H. Kits

Another embodiment provides a pharmaceutical pack or kit including one or more containers filled with of the disclosed humanized antibodies. Additionally, one or more other prophylactic or therapeutic agents useful for the treatment of a disease can also be included in the pharmaceutical pack or kit. The pharmaceutical pack or kit can include one or more containers filled with one or more of the ingredients of the disclosed pharmaceutical compositions Optionally associated with such container(s) can be a notice in the form prescribed by a governmental agency regulating the manufacture, use or sale of pharmaceuticals or biological products, which notice reflects approval by the agency of manufacture, use or sale for human administration.

The kits that can be used in the above methods. In one embodiment, a kit can include one or more of the disclosed humanized antibodies. In another embodiment, a kit further includes one or more other prophylactic or therapeutic agents useful for the treatment of cancer, in one or more containers. In another embodiment, a kit further includes one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

I. Diagnostic Methods

The disclosed antibodies and their antigen-binding fragments can be used for diagnostic purposes, such as to detect, diagnose, or monitor diseases, disorders or infections associated with H7CR expression. The detection or diagnosis of a disease, disorder or infection, particularly an autoimmune disease can be performed by: (a) assaying the expression of H7CR in cells or in a tissue sample of a subject using one or more antibodies (or fragments thereof) that immunospecifically bind to such antigens; and (b) comparing the level of the antigen with a control level, e.g., levels in normal tissue samples or levels in tissue at a different point in time, whereby an increase or decrease in the assayed level of antigen compared to the control level of the antigen is indicative of the disease, disorder or infection. Such antibodies and fragments are preferably employed in immunoassays, such as the enzyme linked immunosorbent assay (ELISA), the radioimmunoassay (RIA) and fluorescence-activated cell sorting (FACS).

One aspect relates to the use of such antibodies and fragments, and particularly such antibodies and fragments that bind to human H7CR, as reagents for IHC analysis in cells of an in vitro or in situ tissue sample or in vivo. Thus, the antibodies and fragments of the have utility in the detection and diagnosis of a disease, disorder, or infection in a human. In one embodiment, such diagnosis includes: a) administering to a subject (for example, parenterally, subcutaneously, or intraperitoneally) an effective amount of a labeled antibody or antigen-binding fragment that immunospecifically binds to H7CR; b) waiting for a time interval following the administration for permitting the labeled molecule to preferentially concentrate at sites in the subject where H7CR is expressed (and for unbound labeled molecule to be cleared to background level); c) determining background level; and d) detecting the labeled antibody in the subject, such that detection of labeled antibody above the background level indicates that the subject has the disease, disorder, or infection. In accordance with this embodiment, the antibody is labeled with an imaging moiety which is detectable using an imaging system known to one of skill in the art. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In vivo tumor imaging is described in S. W. Burchiel et al., "*Immunopharmacokinetics of Radiolabeled Antibodies and Their Fragments*," (Chapter 13 in TUMOR IMAGING: THE RADIO-CHEMICAL DETECTION OF CANCER, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of a disease, disorder or infection is carried out by repeating the method for diagnosing the disease, disorder or infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

Having now generally described the invention, the same will be more readily understood through reference to the following examples, which are provided by way of illustration and are not intended to be limiting of the present invention unless specified.

Example 1

Characterization of Anti-Human H7CR Antibodies and Expression Pattern of H7CR Materials and Methods For binding affinity estimation, 0.2 million CHO.hH7CR transfectants (FIG. 2), naïve CD4+CD45RA+ T cells (FIG. 3A) or naïve CD8+CD45RA+ T cells (FIG. 3B) were resuspended in 100 µl flow cytometry buffer (PBS+2% FBS). A serial dilution of chimeric 1.3 and 4.5 of 0, 0.1 ng, 0.3 ng, 1 ng, 3 ng, 10 ng, 30 ng, 100 ng, 300 ng, 1 µg, 3 µg and 10 µg were added to the cells and incubated at 4° C. for 30 min. Cells were then washed twice with 2 ml flow cytometry buffer, and resuspended in 100 µl flow cytometry buffer. 1 µl anti-hIg PE secondary antibody (Biolegend) was added and incubated with the cells for 15 mins Samples were then washed and resuspended in 100 µl flow cytometry buffer. Flow Cytometry data was acquired using BD Canto (BD Biosciences) in plate format and analyzed by FlowJo software. Staining data (MFI) was then input into Prism 5 software to generate binding curve. Curve-fit using one-site specific binding algorithm calculates individual $K_D$ for each antibody.

5 µg/ml H7CR 1.3, 4.5 and 7.8 mAbs was used to stain H7CR stable transfectants to show binding specificity (FIG. 4). 10 µg/ml B7-H7mIg fusion protein was also used to stain H7CR CHO transfectants. H7CR mAbs were added to the system to evaluate the blocking capability of H7CR mAbs on B7-H7-H7CR interactions (FIG. 5).

Figure 6:
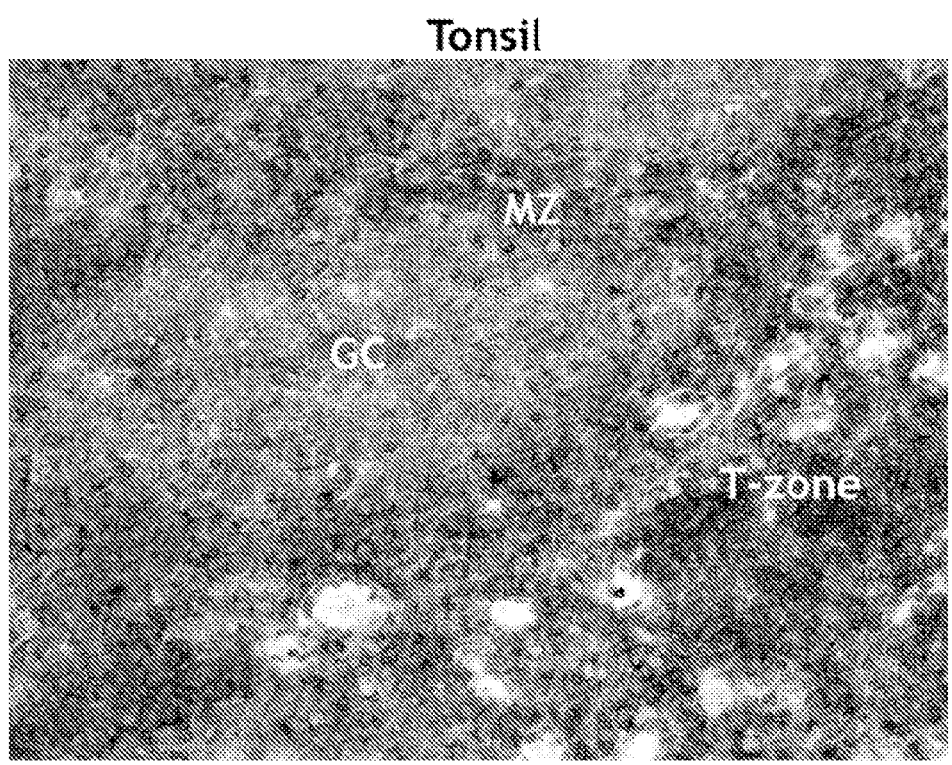
FIG. 6 is photomicrograph showing the ability of anti-human H7CR antibody (H7CR 4.5) to bind to H7CR as endogenously expressed on the surface of human tonsil tissue.
Figure 10:
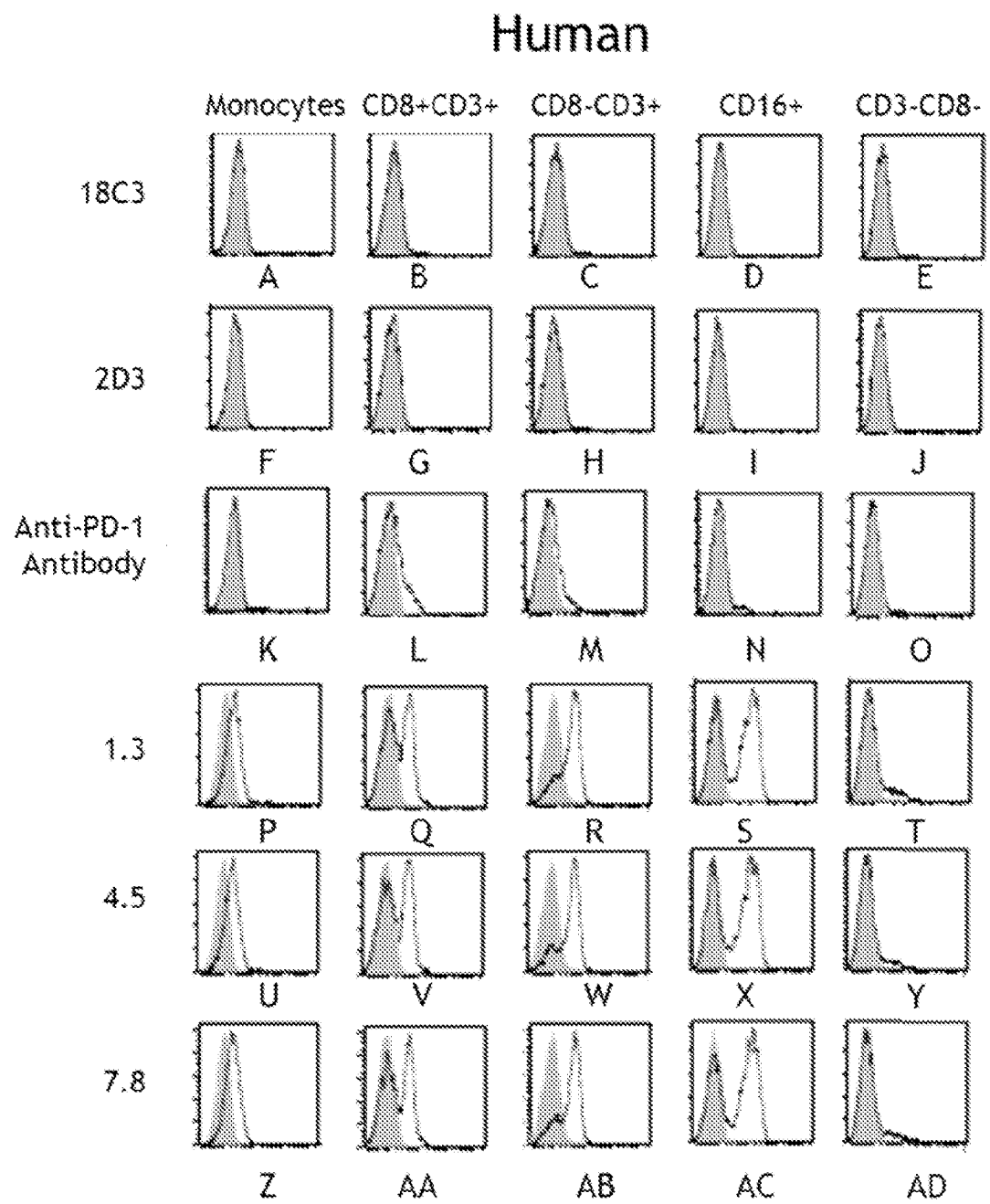
Figure 11:
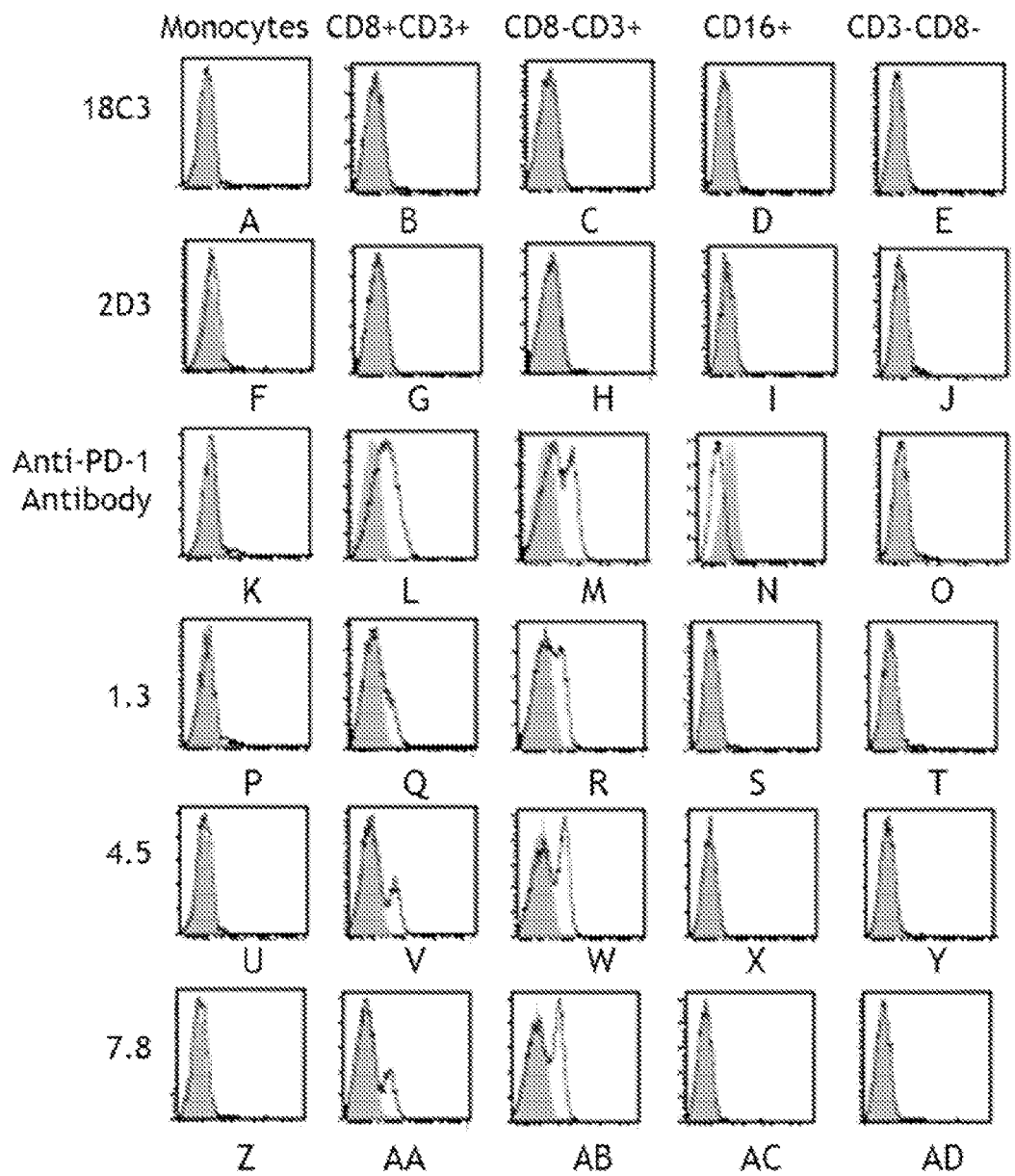
Figure 12:
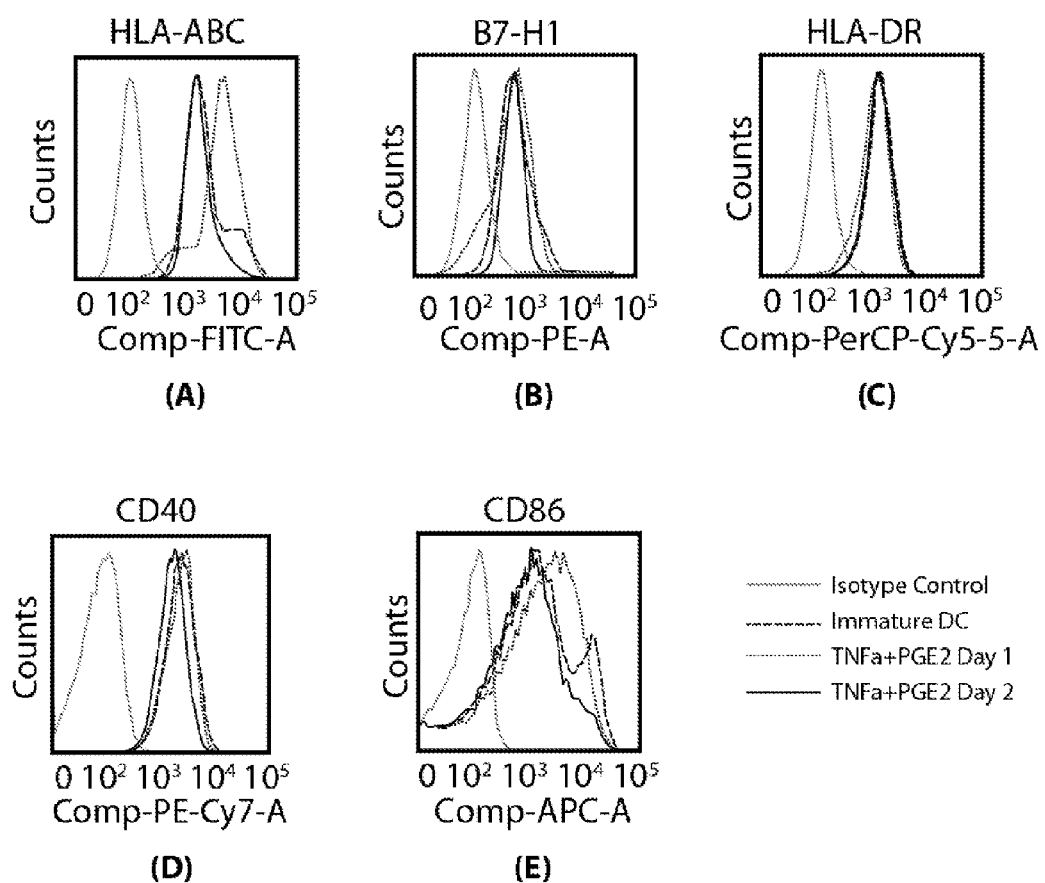
FIGS. 12A-12K are flow cytometry histograms of in vitro analysis of the expression of B7-H7 and other activation markers by matured monocyte-derived dendritic cells.
Figure 12:
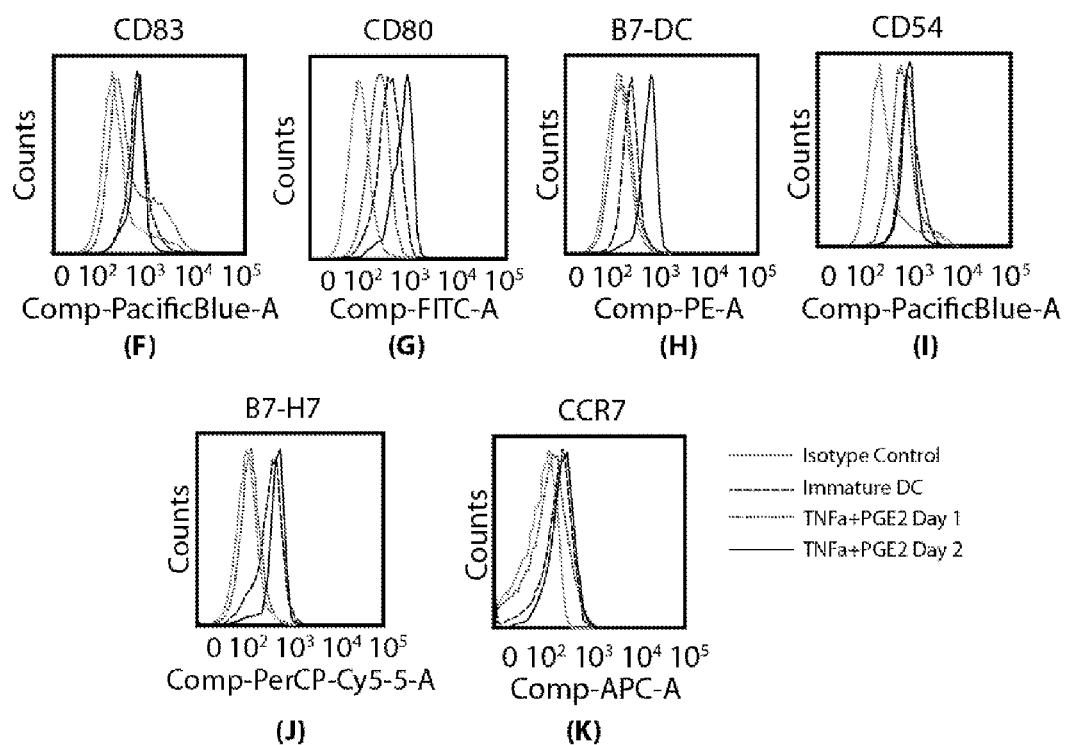

Immunohistochemistry staining for H7CR on human tonsil paraffin-embedded section was performed with 4.5 antibody at a concentration of 5 μg/ml using a standard protocol (FIG. 6). For cell surface staining and analysis by flow cytometry, cells were incubated with the indicated mAb for 30 min at 4° C., washed with buffer and analyzed. Expression of H7CR on human and mouse PBMC was evaluated by lineage marker and 1.3 antibody staining (FIG. 7-11). Expression of B7-H7 on activated monocyte-derived DC was evaluated by anti-B7-H7 antibody staining (FIG. 12).

Results

Figure 2:
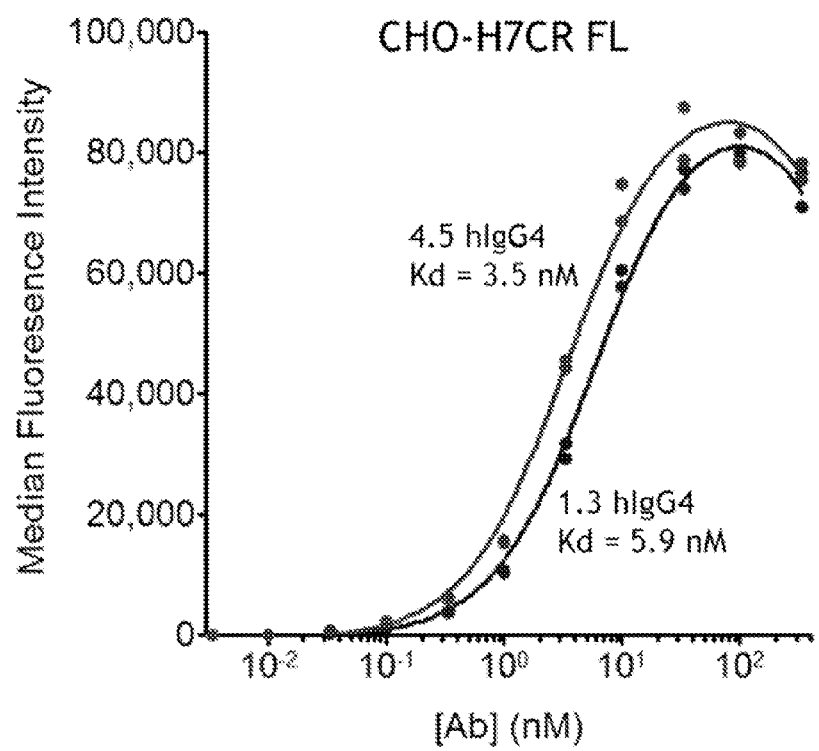
FIG. 2 is a line graph of Median Fluorescence Intensity versus log [Ab] (nM) showing the respective binding affinities of anti-H7CR antibodies 1.3 (Kd=5.9 nM) and 4.5 (Kd=3.5 nM) to H7CR CHO transfectants.

Hamster antibodies 1.3, 4.5 and 7.8 were found to be capable of immunospecifically binding to human H7CR. FIG. 2 shows the respective binding affinities of anti-H7CR antibodies 1.3 and 4.5. Antibody 4.5 was found to have a Kd of 3.5 nM. Antibody 1.3 was found to have a Kd of 5.9 nM. H7CR mAb binding curves to naïve CD4 and CD8 T cells indicated that the receptor saturation dose for both antibodies was 1 μg/ml (FIG. 3, Panels A and B).

Figure 4:
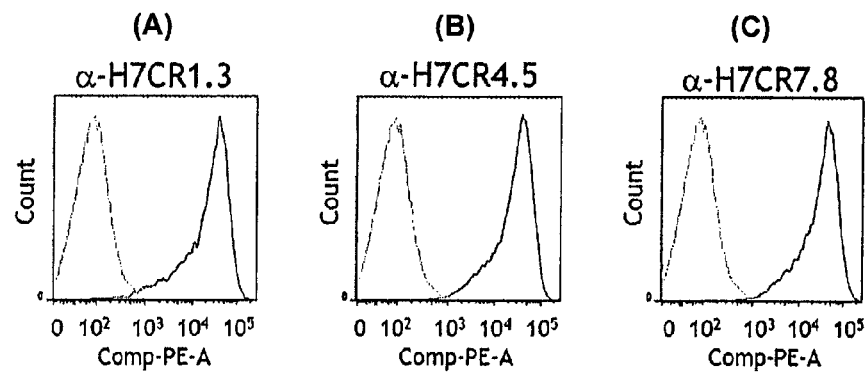
FIGS. 4(A)-4(C) are histograms of flow cytometry data showing the ability of the antibodies 1.3, 4.5 and 7.8 to bind to human H7CR expressed on the surface of CHO transfectants. The data are presented as cell Count versus log fluorescence of Comp PE-A. The left peak in each panel presents isotype control antibody; the right peak represents H7CR antibody.
Figure 5:
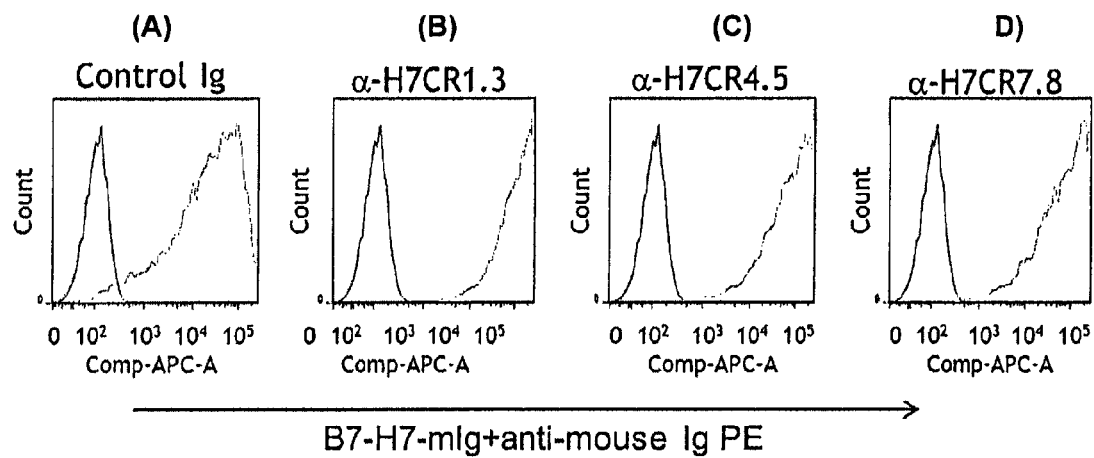
FIGS. 5A-5D are histograms of flow cytometry data showing that B7-H7Ig fusion protein binds to H7CR CHO transfectant. The data are presented as cell Count versus log fluorescence of Comp APC-A. Pre-incubation of antibodies 1.3 (FIG. 5B), 4.5 (FIG. 5C) and 7.8 (FIG. 5D) with H7CR transfectants were each found to be substantially incapable of blocking H7CR's interaction with B7-H7.

FIG. 4 (Panels A-C) show the ability of the antibodies 1.3, 4.5 and 7.8 to bind to human H7CR expressed on the surface of CHO cells. The antibodies were tested for their ability to block H7CR's interaction with B7-H7 by incubating the antibodies with H7CR CHO transfectants in the presence of a B7-H7-murine IgG2a fusion protein. As shown in FIG. 5 (Panels A-D), the presence of H7CR antibodies did not disrupt the ability of the B7-H7 Ig to bind to H7CR. Thus, these three antibodies were substantially incapable of blocking H7CR's interaction with B7-H7. As shown in FIG. 6, the anti-human H7CR antibody (Clone 4.5) was found to be capable of binding to H7CR as endogenously expressed on the surface of human tonsil tissue.

Figure 7:
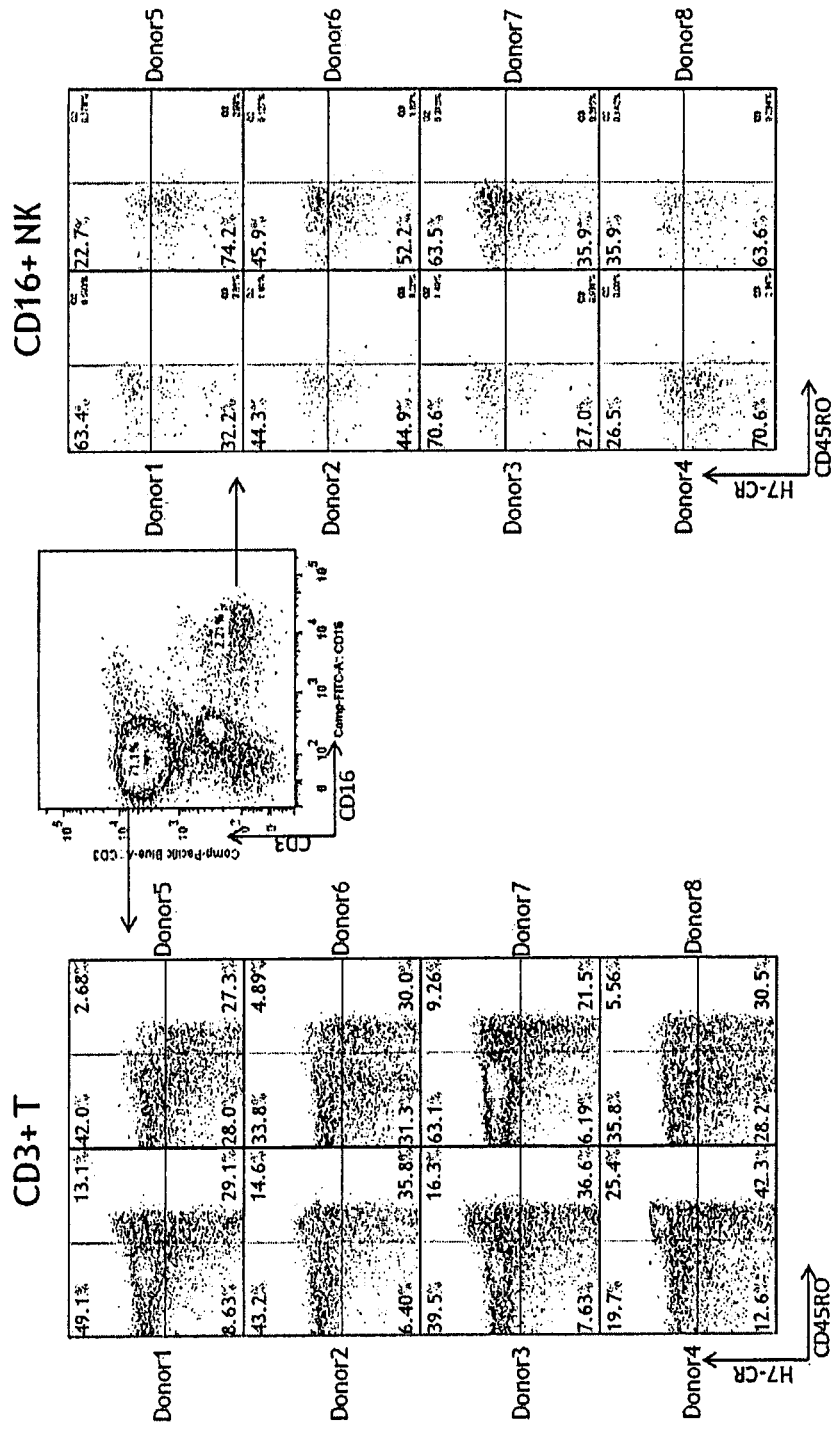
FIG. 7 presents scatter plots of flow cytometry data showing that H7CR expression was associated with a naive T cell phenotype in T and NK cells. The scatter plots on the left side of FIG. 7 present data from eight donors showing expression of H7CR on CD3+ T cells relative to their expression of CD45RO. The scatter plots are fluorescence of anti-H7-CR antibody versus fluorescence from anti-CD45RO antibody. The scatter plot in the middle of FIG. 7 shows gating of T cells and NK cells based on the expression of CD3 and CD 16 markers. The scatter plot is fluorescence of anti-CD3 antibody versus fluorescence from anti-CD 16 antibody. The scatter plots on the right side of FIG. 7 present data from eight donors showing expression of H7CR on CD16+ NK cells relative to their expression of CD45RO. The scatter plots are fluorescence of anti-H7-CR versus fluorescence from anti-CD45RO antibody.
Figure 8:
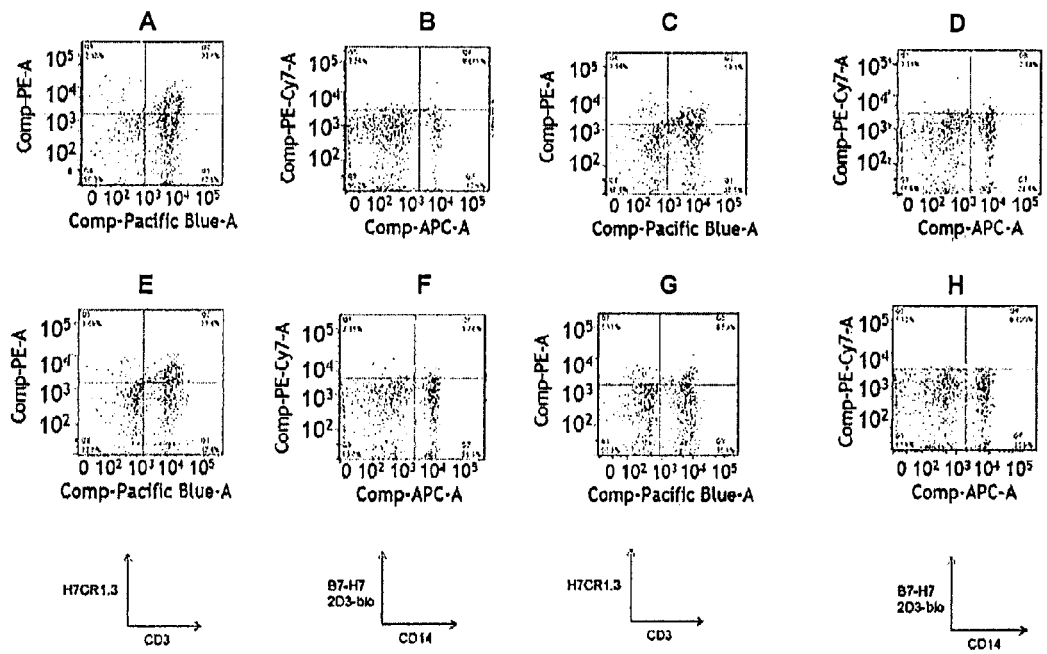
FIGS. 8A-8H are flow cytometery scatter plots of the expression profiles of H7CR and B7-H7 of four healthy PMBC donors (Donor 1, FIGS. 8A and 8B; Donor 2, FIGS. 8C and 8D; Donor 3 (FIG. 8E and FIG. 8F) and Donor 4 (FIG. 8G and FIG. 8H)).
Figure 9:
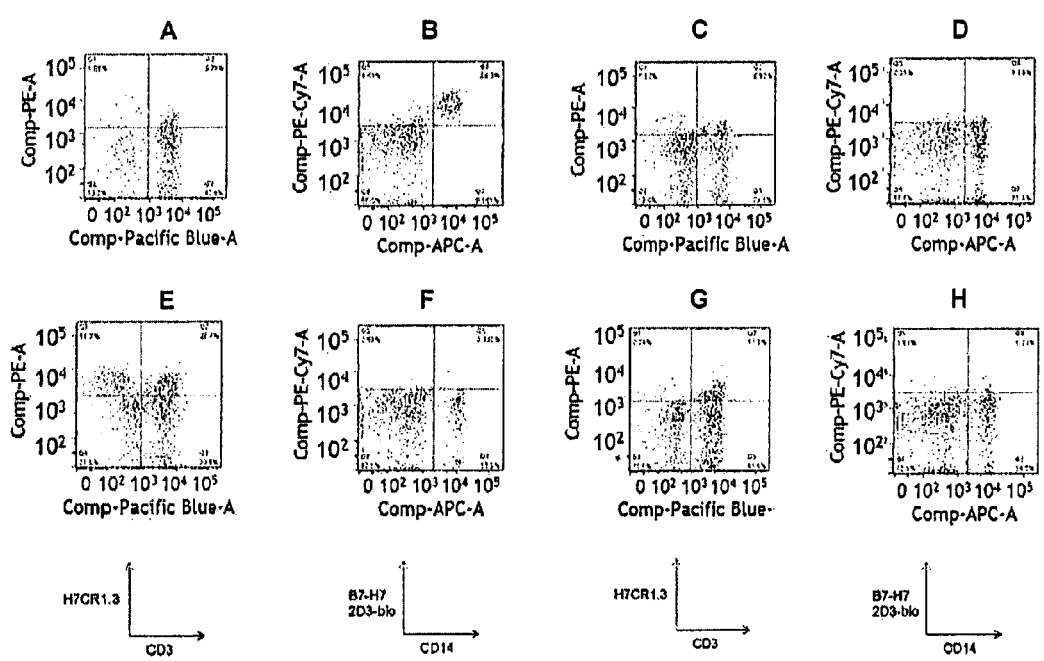
FIGS. 9A-9H are flow cytometery scatter plots showing the expression profiles of H7CR and B7-H7 of four healthy PMBC donors (Donor 1, FIGS. 9A and 9B; Donor 2, FIGS. 9C and 9D; Donor 3, FIGS. 9E and 9F; and Donor 4, FIGS. 9G and 9H).

The anti-H7CR antibodies permitted a determination of the expression profiles of H7CR and B7-H7. FIG. 7 shows that H7CR expression was associated with a naïve T cell phenotype in T and NK cells. FIG. 8 (Panels A-H) shows the expression profiles of H7CR and B7-H7 of four healthy PMBC donors (Donor 1, Panels A and B; Donor 2, Panels C and D; Donor 3 (Panels E and F) and Donor 4 (Panels G and H)). FIG. 9 (Panels A-H) shows the expression profiles of H7CR and B7-H7 of four healthy PMBC donors (Donor 1, Panels A and B; Donor 2, Panels C and D; Donor 3 (Panels E and F) and Donor 4 (Panels G and H)). FIG. 10 (Panels A-AD) shows the expression of H7CR and B7-H7 by human monocytes, CD8+ CD3+ lymphocytes, CD8− CD3+ lymphocytes, CD16+ NK cells, and CD3− CD8− cells. FIG. 11 (Panels A-AD) shows the expression of H7CR and B7-H7 by cynomolgus monkey monocytes, CD8+ CD3+ lymphocytes, CD8− CD3+ lymphocytes, CD16+ NK cells, and CD3− CD8− cells, and indicates that cynomolgus monkey is a relevant species for in vivo and toxicology studies.

An in vitro functional analysis of expression of B7-H7 was conducted. Matured monocyte-derived dendritic cells were evaluated for their ability to express B7-H7 and other activation markers. The results of this study (FIG. 12, Panels A-K) confirm the expression of such markers and show that matured dendritic cells are relevant for in vitro functional testing.

Example 2

Anti-H7CR Antibodies Promote Antigen Specific Memory T Cell Responses

Materials and Methods

Figure 13:
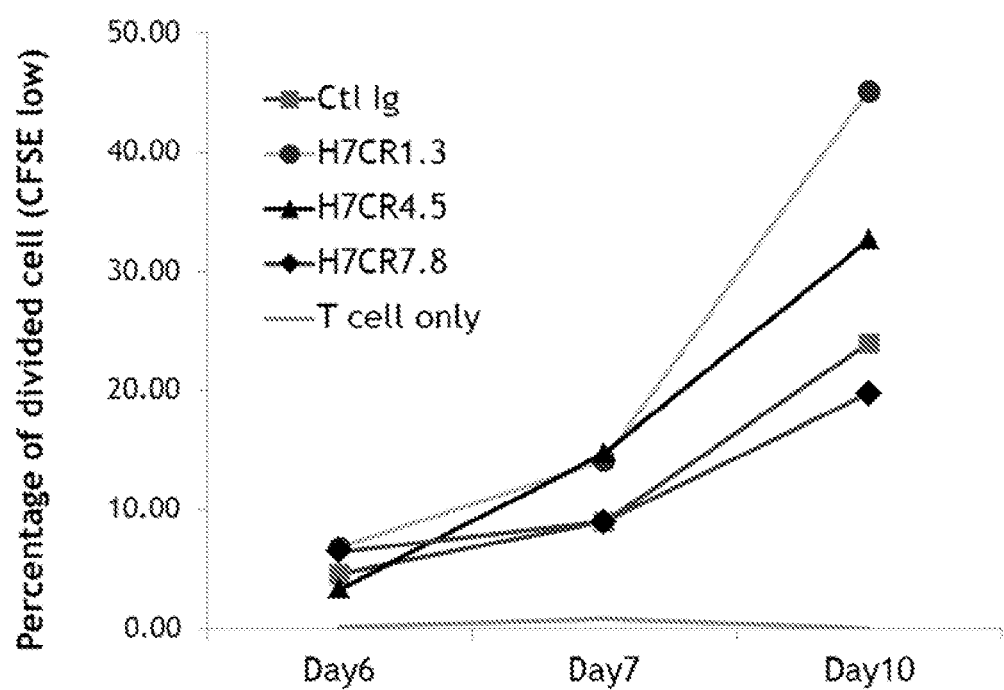
FIG. 13 is a line graph of Percentage of divided cell (CFSE low) versus Days for Ctl Ig (■), H7CR1.3 (●), H7CR4.5 (▲), H7CR7.8 (♦) and T cell only (-) and shows that the anti-H7CR antibodies promote model antigen, Tetanus Toxoid, specific T cell responses.
Figure 23:
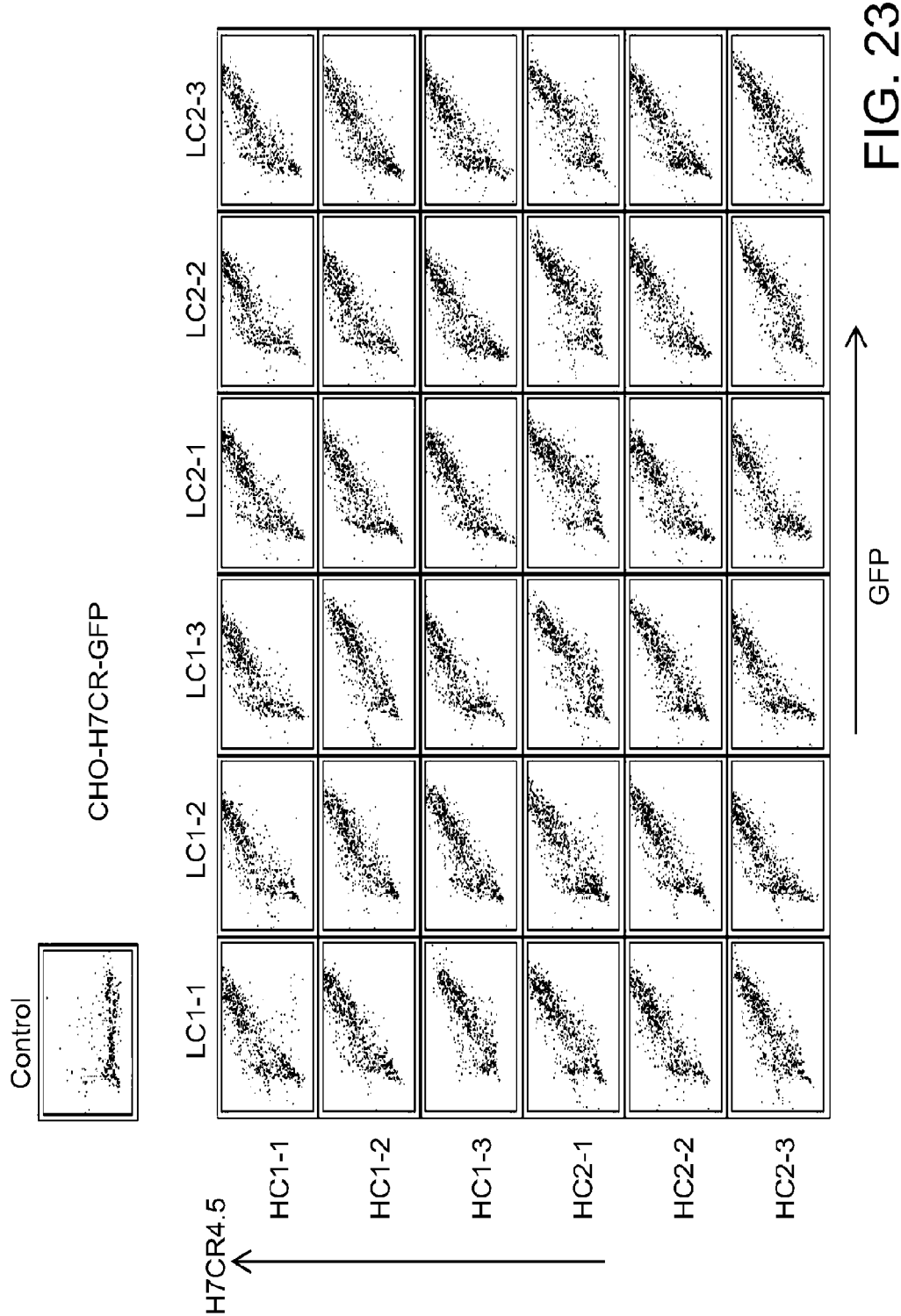
FIG. 23 provides a series of flow cytometry scatter plots of thirty-six humanized H7CR4.5 with the indicated heavy and light chains. Thirty-six variants were incubated with H7CR-GFP fusion protein transfected CHO cells.

In order to further characterize the anti-H7CR antibodies, a tetanus toxoid (TT) memory recall response assay was conducted. Monocyte-derived immature DC were matured by incubation with 1 ng/ml TNFα and 1 μg/ml PGE2 for two days, and were incubated in the presence of 50 μg/ml tetanus toxoid (TT) overnight on the second day of DC maturation. The dendritic cells were washed three times with X-Vivo media and then incubated in the presence of carboxyfluorescein succinimidyl ester (CFSE)-labeled autologous T cells at a ratio of 1:20 for two weeks in the presence of 100 ng/ml TT and 10 μg/ml H7CR1.3, 4.5 or 7.8 monoclonal antibody (FIG. 13), or humanized 1.3 variants (FIG. 23). Cellular proliferation was monitored by CFSE dilution using flow cytometry. In some experiments, intracellular staining of human IFNγ and TNFα were performed. Golgi Blocker Brefeldin A (eBioscience) was added into DC-T cell culture system for 8 hours. Activated human T cells were harvested and washed with cold PBS. Cell surface markers were first stained. Intracellular staining for IFNγ and TNFα was preformed according to manufacturer's protocol (Cytofix/Cytoperm, BD).

Culture supernatants were collected at different time points for total cytokine analysis by Bio-Plex Pro Human Cytokine 17-Plex kit (M5000031YV, BioRad) according to Manufacturer's manual. Data were collected and analysized by Bio-Plex 200 system (BioRad).

Results

Figure 14:
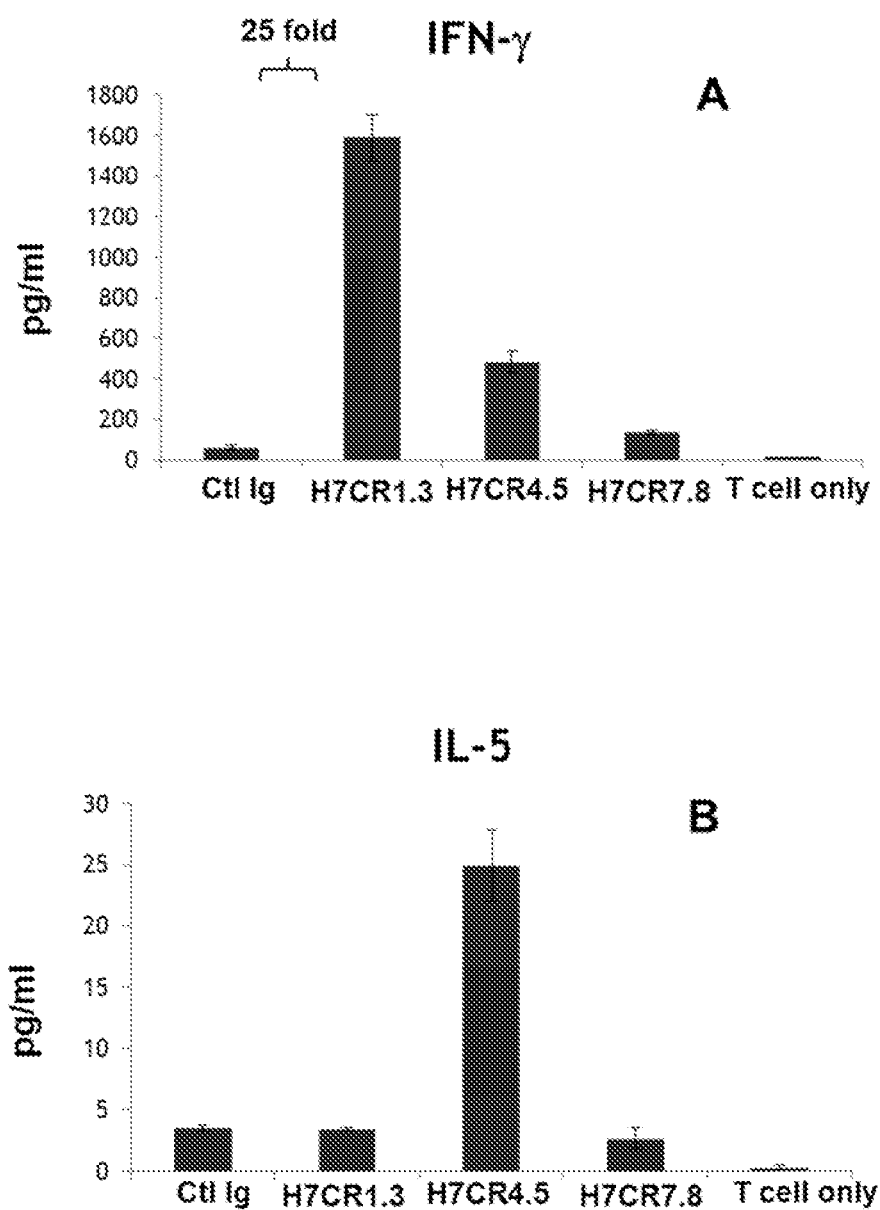
FIGS. 14A-14L present bar graphs that show the nature and levels of cytokines expressed by the cells subjected to a tetanus toxoid protein stimulation and H7CR antibody or control antibody treatment.
Figure 14:
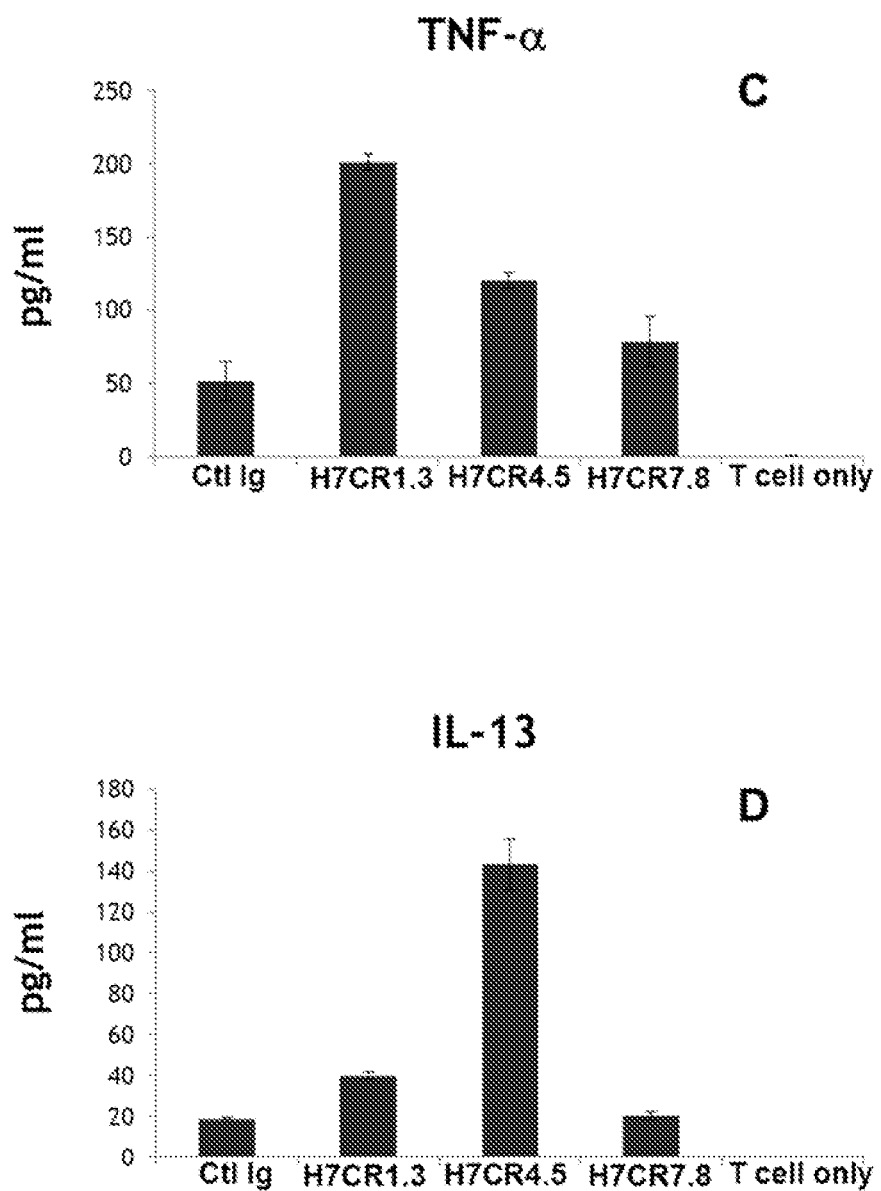
Figure 14:
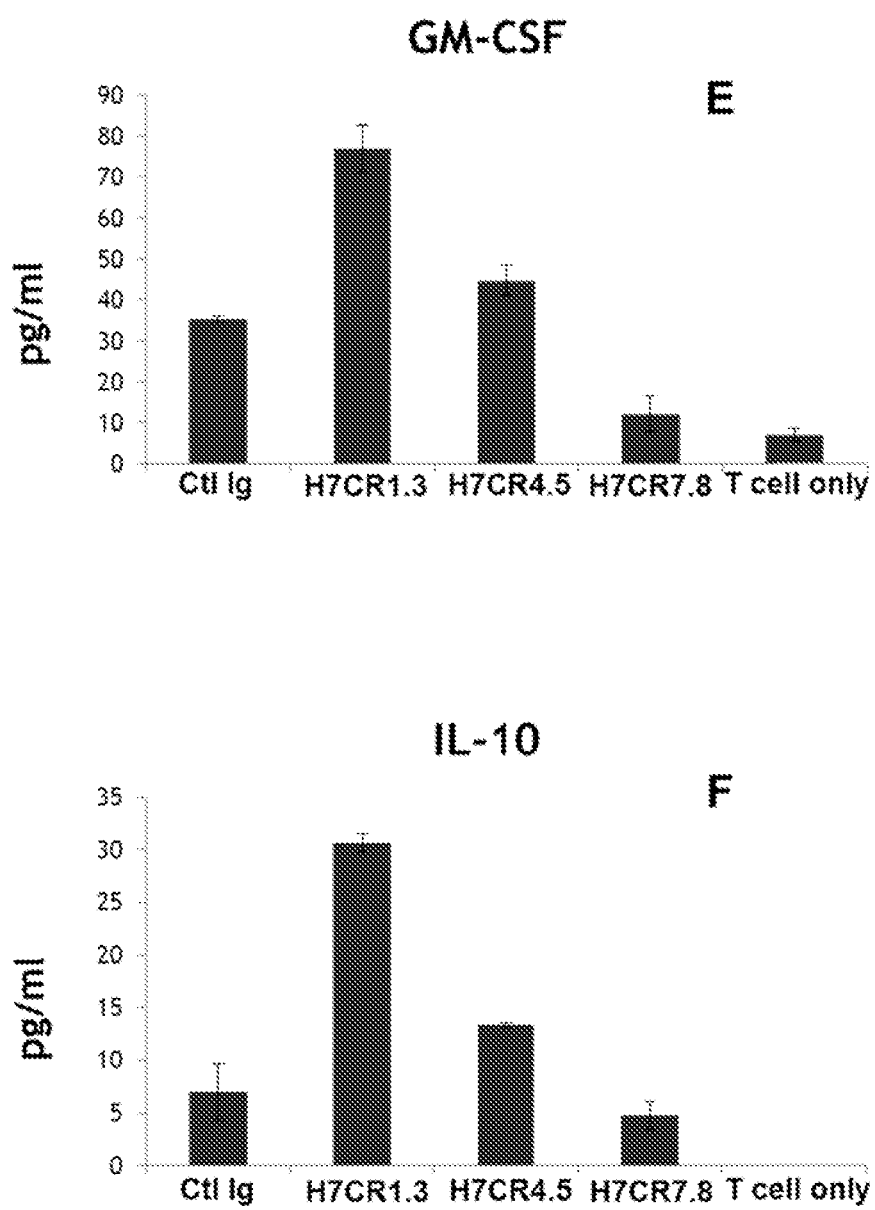
Figure 14:
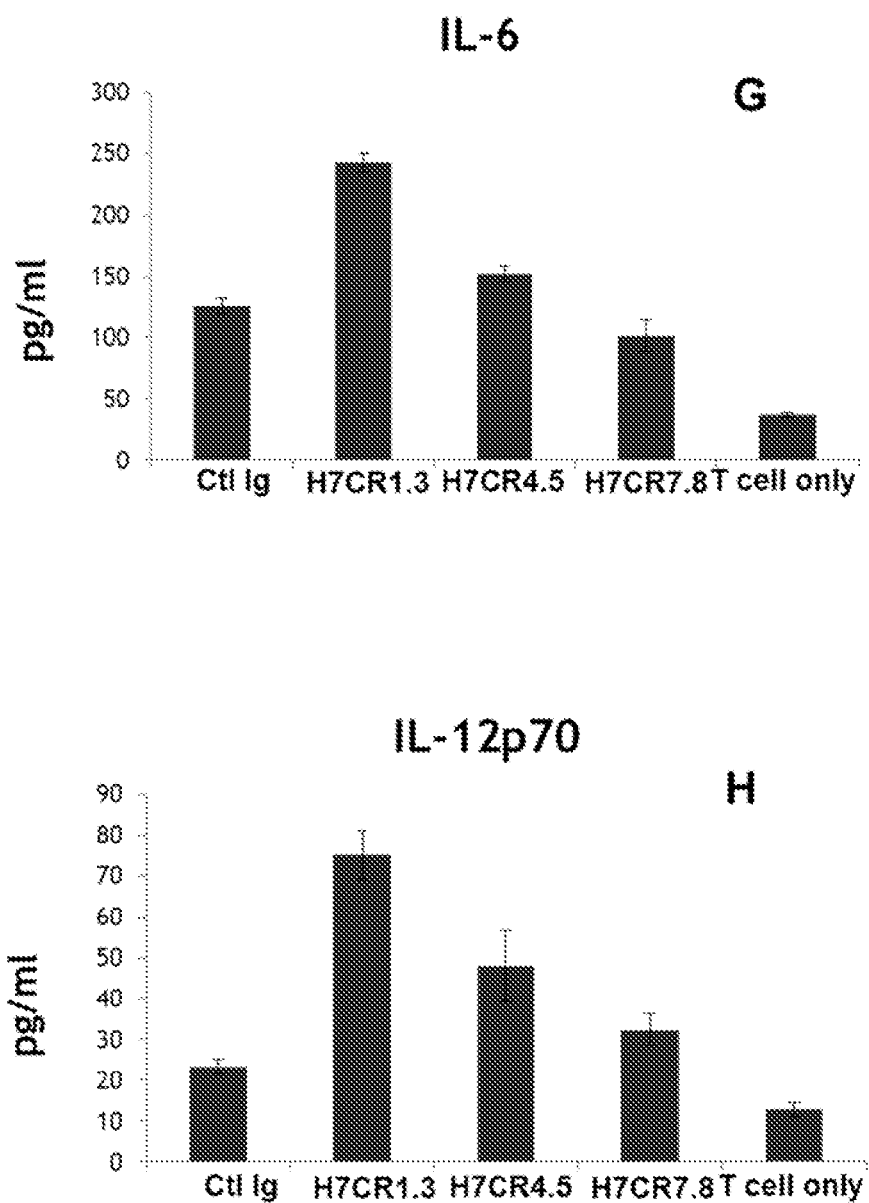
Figure 14:
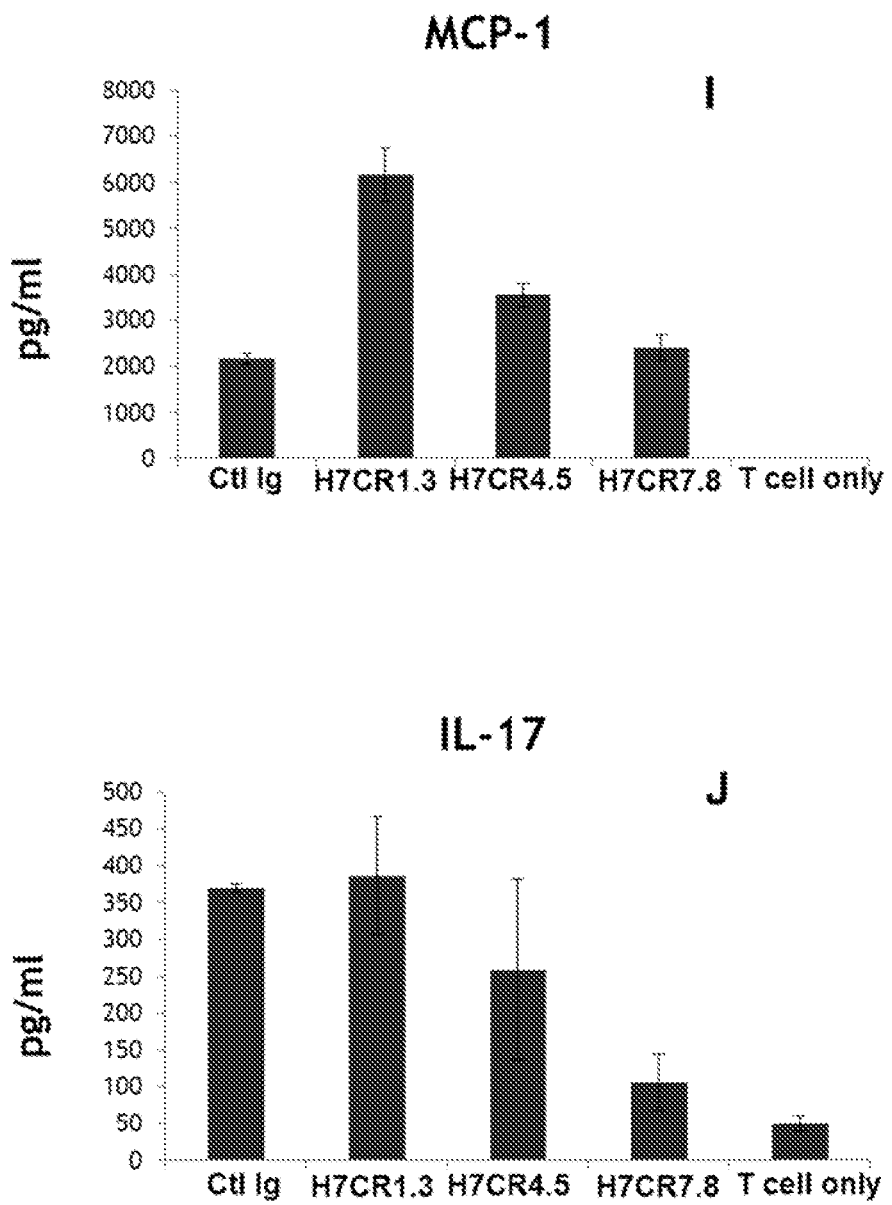
Figure 14:
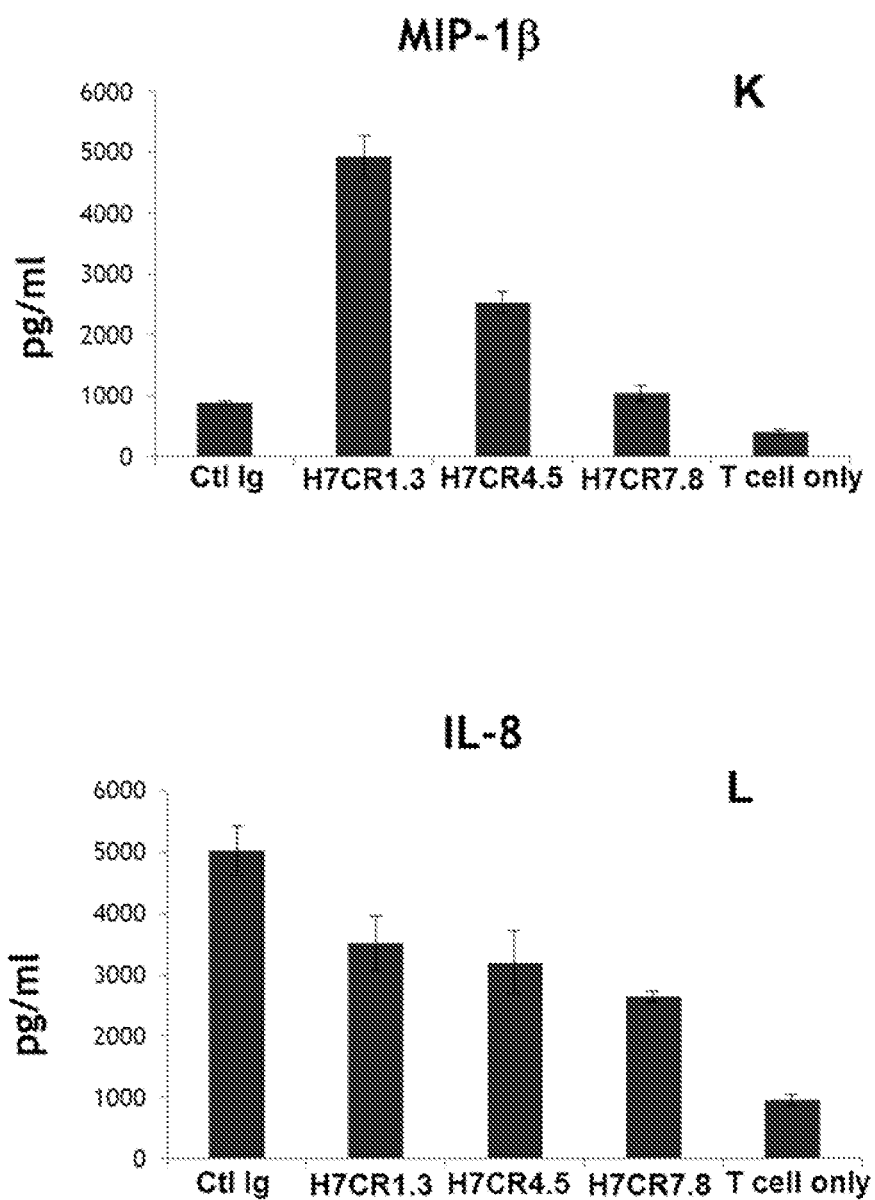

The results of this analysis (FIG. 13) show that the anti-H7CR antibodies promote antigen specific memory T cell responses. The day 7 supernatants were evaluated in order to determine the nature and levels of cytokines expressed by the cells. The results of this analysis are shown in FIG. 14 (Panels A-L). The results show that anti-H7CR antibodies 1.3, 4.5 and 7.8 mediated non-identical cytokine expression profiles. Notably, antibody 1.3 mediated high levels of IFNγ, TNFα, GM-CSF and IL-10 and antibody 4.5 mediated high levels of IL-5 and IL-13.

Figure 15:
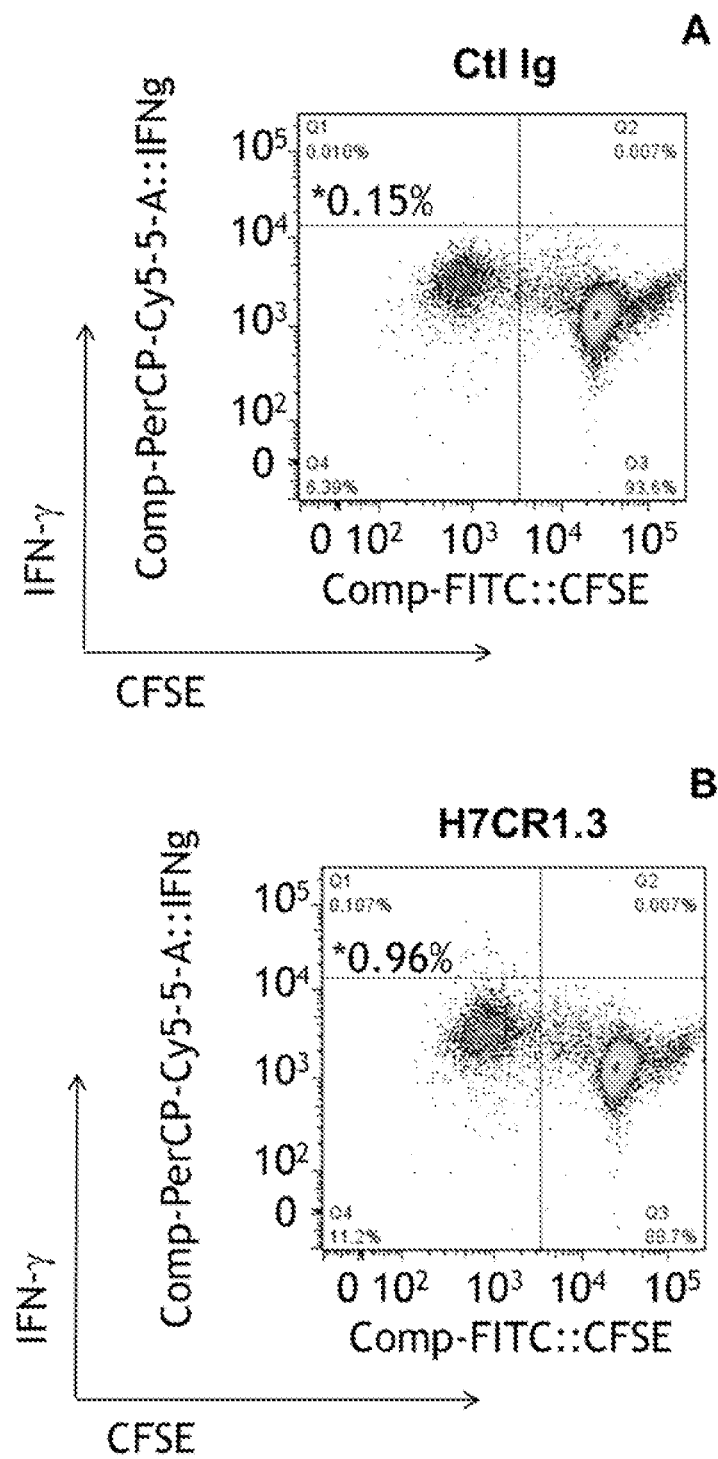
FIGS. 15A and 15B are flow cytometry scatter plots that show that treatment with anti-H7CR antibodies enhanced proliferation and intracellular IFNγ expression in antigen-specific T cells.

Cells were subjected to intracellular staining after 5 hr incubation with Golgi Block (without PMA and Ionmycin) and their intracellular expression of IFN' and carboxyfluorescein succinimidyl ester (CSFE) dilution were assessed. The results of this investigation revealed that treatment with anti-H7CR antibodies enhanced proliferation as represented by CFSE dilution and IFNγ expression in antigen-specific T cells (FIGS. 15A and 15B). The IFNγ+ percentage in divided T cells increased from 0.15% (FIG. 15A; control) to 0.96% (FIG. 15B; antibody 1.3 treated).

Among 1.3 humanized variants (FIG. 23), variant 1, 3 and 5 showed comparable enhancement of CFSE dilution with the parental chimeric 1.3 antibody of the TT-specific T cells.

Example 3

The Interaction of B7-H7:H7CR Regulates Antigen-Specific Human T Cell Responses

Materials and Methods

In order to determine the role of the B7-H7:H7CR pathway on the antigen-specific T cell response, purified human CD4+ T cells were labeled with CF SE, and cultured with autologous monocyte-derived dendritic cells that had been pre-incubated with 50 μg/ml tetanus toxoid ("TT") as antigen. The dendritic cells were washed three times with X-Vivo media and then incubated in the presence of carboxyfluorescein succinimidyl ester (CFSE)-labeled autologous T cells at a ratio of 1:20 for two weeks in the presence of 100 ng/ml TT and 10 μg/ml H7CR monoclonal antibody. Cellular proliferation was monitored by CFSE dilution using flow cytometry.

Results

Figure 16A:
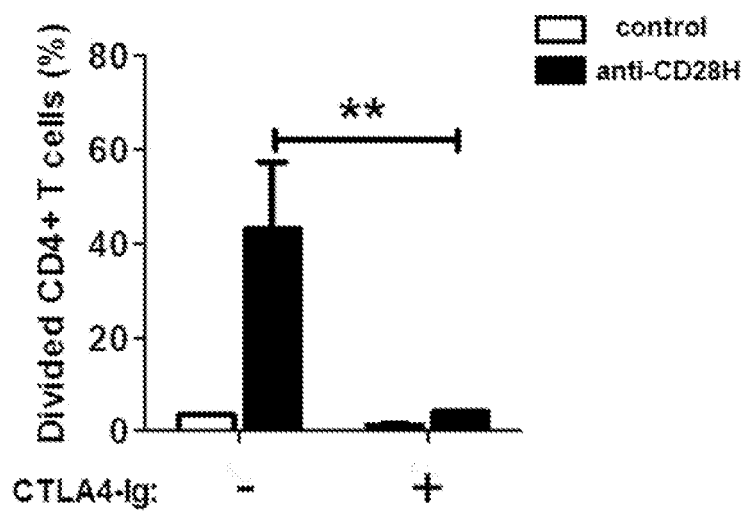
FIGS. 16A-16B are bar graphs that show the effects of anti-H7CR antibodies on human T cell responses.

A TT-specific T cell proliferation was found to be strongly augmented when agonistic anti-H7CR mAb were included in the culture (to amplify H7CR signal on T cells) (FIG. 16A). Inclusion of CTLA4-Ig, a fusion protein blocking B7:CD28 interactions, in the beginning of cell culture greatly inhibited T cell proliferation, even in the presence of agonistic anti-H7CR mAb. These results indicate that H7CR co-stimulation is dependent on endogenous B7:CD28 interaction.

Figure 16B:
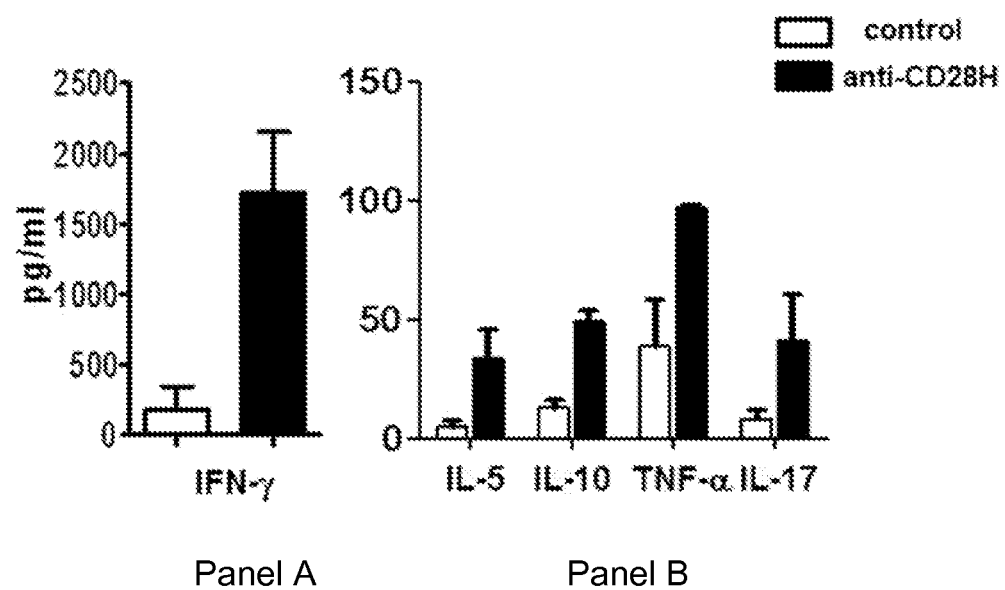

Cells incubated in the presence of the agonistic anti-H7CR mAb exhibited a substantial enhancement of cytokine production, including IFN-γ (FIG. 16B, Panel A) and IL-5, IL-10, TNF-α and IL-17 (FIG. 16B, Panel B). These results indicate that H7CR co-stimulation is not specific for a subset of $CD4^+$ T helper cells. Together, these results indicate that the H7CR signal promotes the growth and differentiation of pan human $CD4^+$ T cells, a feature similar to CD28 co-stimulation.

Example 4

Humanization of Anti-H7CR Antibodies 1.3 and 4.5

Hamster anti-H7CR antibodies 1.3 and 4.5 were humanized using a process that included generating a homology modeled antibody 3D structure and creating a profile of the parental antibody based on structure modeling. A set of humanized heavy and light chain variable region sequences were generated, each of which combined specific regions of the parental antibody sequence with the majority of the human framework sequence. A total of 6 humanized heavy chain sequences and 6 humanized light chain sequences were produced.

Sequence alignments comparing the variable domains of antibody 1.3 to the human germline framework sequence database were generated using Geneious. Preferred acceptor frameworks were identified based on the overall sequence identity across the framework, matching interface position, similarly classed CDR canonical positions, and presence of N-glycosylation sites that would have to be removed.

A structural model of the variable light and heavy chains of the antibodies was generated in Discovery Studio. Template structures were identified by searching the PDB database with the 1.3 light chain and heavy chain variable domain sequences with and without their CDRs. The alignment of the 1.3 sequences to the templates and modeling the structures based on homology were carried out using MODELLER (Sali, A. et al. (1993) "*Comparative Protein Modelling By Satisfaction Of Spatial Restraints,*" J. Molec. Biol. 234(3):779-815).

A number of hybrid sequences that combined different regions of the parental antibody sequence with that of the human frameworks were systematically analyzed using the 3D model to identify the hybrid sequences that were predicted to have the least impact on the defined structure of the CDRs (Chothia, C. et al. (1987) "*Canonical Structures For The Hypervariable Regions Of Immunoglobulins,*" J. Mol. Biol. 196:901-917; Martin, A. C. et al. (1996) "*Structural Families In Loops Of Homologous Proteins: Automatic Classification, Modelling And Application To Antibodies,*" J. Molec. Biol. 263(5):800-815). Particular attention was given to hybrid sequences that contained amino acids from the human framework that were within 5 Å of CDR loops, in the Vernier zone, in the VH/VL interchain interface, or in CDR canonical class determining positions, as these hybrid sequences are judged more likely to have a detrimental effect on the function of the resulting humanized antibody.

A profile of the parental antibody was created based on CDR analysis and structure modeling. Human acceptor frameworks were identified based on sequence and homology comparisons. Humanized antibodies were designed by creating multiple hybrid sequences that fuse parts of the parental antibody sequence with the human framework sequences. Using the 3D model, these humanized sequences were methodically analyzed by eye and by computer modeling to isolate the sequences that would most likely retain antigen binding. The goal was to maximize the amount of human sequence in the final humanized antibody while retaining the original antibody specificity.

Figure 17A:
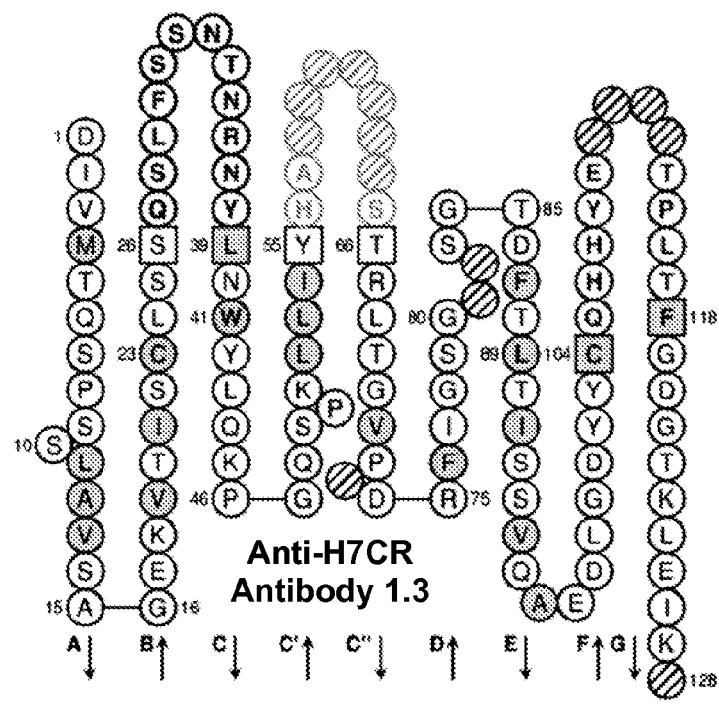
FIGS. 17A-17B show Collier Perles 2D representations of the variable domains of the light chain (FIG. 17A) and heavy chain (FIG. 17B) of antibody 1.3. The three CDR loops of the chains are shown at the top of the diagrams. The hatched circles are missing residues for this mAb. The squared amino acids are the conserved amino acids at that position.
Figure 17B:
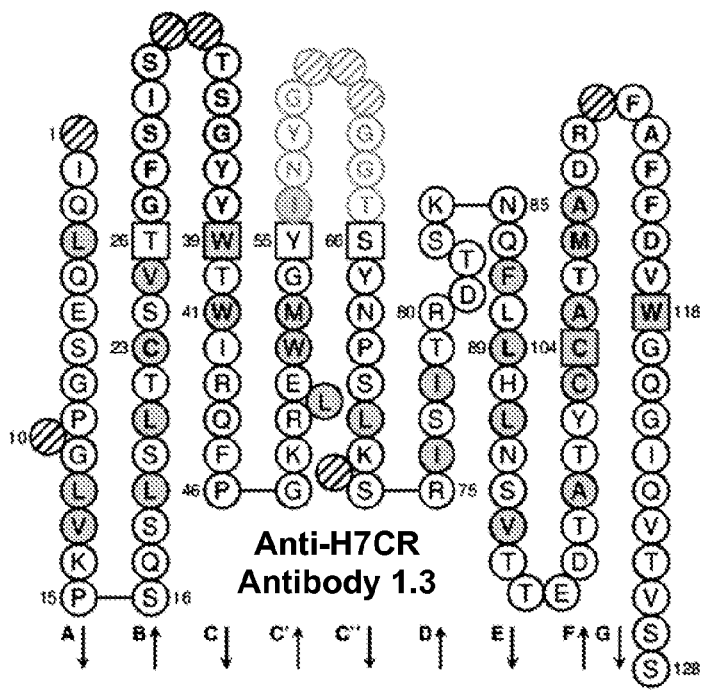
Figure 18A:
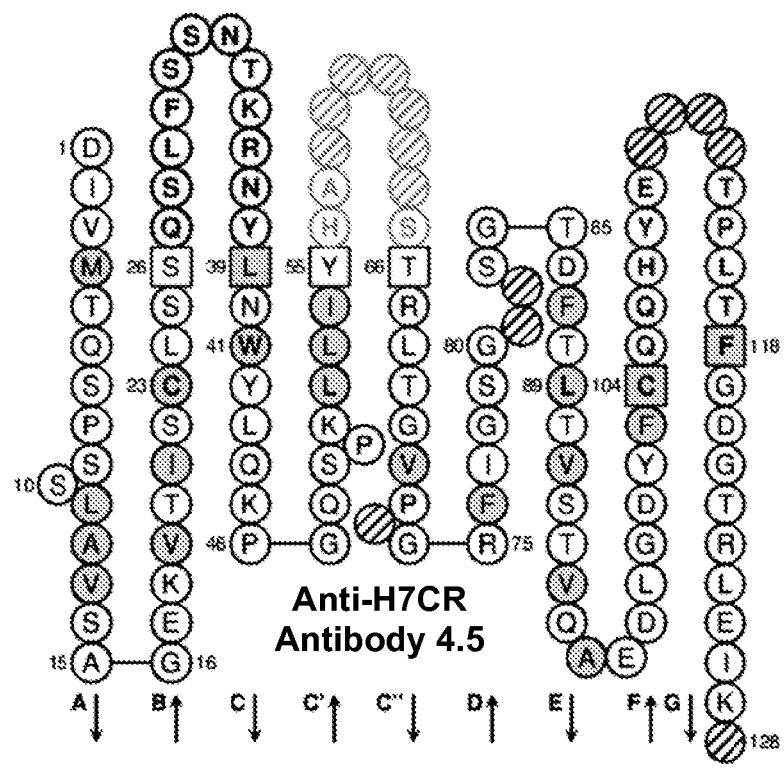
FIGS. 18A-18B show Collier Perles 2D representations of the variable domains of the light chain (FIG. 18A) and heavy chain (FIG. 18B) of antibody 4.5. The three CDR loops of the chains are shown at the top of the diagrams. The hatched circles are missing residues for this mAb. The squared amino acids are the conserved amino acids at that position.
Figure 18B:
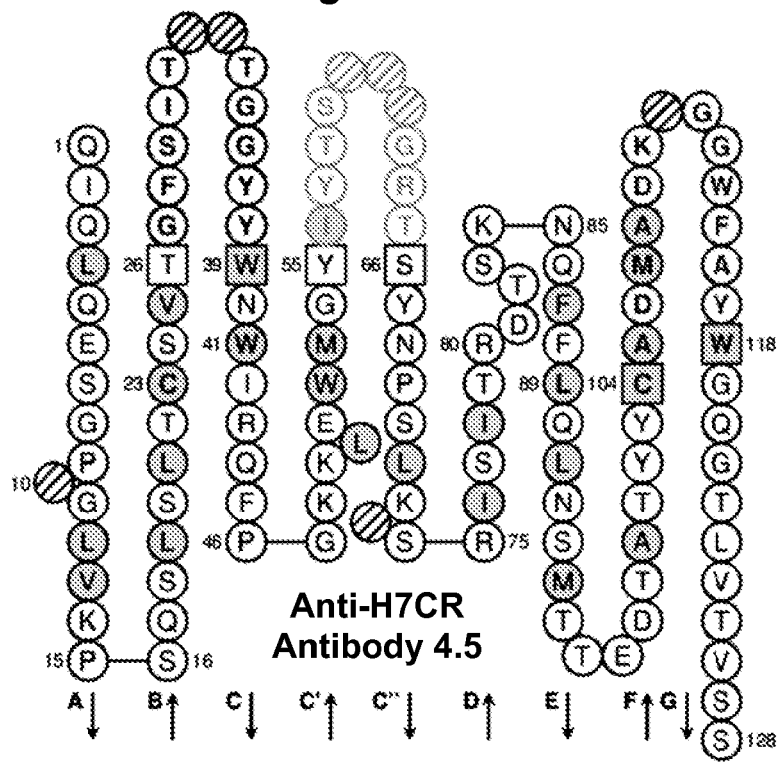

Collier de Perles is a 2D representation of variable domains and provides information on the amino acid positions in beta-strands and loops in the variable domains (Ruiz, M. et al. (2002) "*IMGT Gene Identification And Colliers de Perles Of Human Immunoglobulins With Known 3D Structures,*" Immunogenetics 53(10-11):857-883). Collier de Perles of antibody 1.3 light chain and heavy chain variable regions are shown in FIG. 17A and FIG. 17B, respectively. FIGS. 18A and 18B show the Collier de Perles of the antibody 4.5 light chain and heavy chain variable regions, respectively. The three CDR loops of the chains are shown at the top of the diagrams. There are no free Cys residues or N-linked glycosylation sites in the variable light or heavy chain regions.

Humanization of Antibody 1.3

Sequence alignments comparing hamster antibody 1.3 variable domains to the human germline database were generated. Based on the overall sequence identity, matching interface position, and similarly classed CDR canonical positions, two germline families were identified as possible acceptor frameworks for the light chain: IGKV4-1*01 and IGKV2D-28*01. The J-segment genes were compared to the parental sequence over FR4 and J-segments, and IGKJ2*01 was selected for the light chain. Alignment of the parental 1.3 VL chain to these acceptor frameworks is shown in Table 6, with non-identical residues shown underlined.

TABLE 6

| Variable Light Chain | SEQ ID # | Sequence |
|---|---|---|
| | |           10           20          30          40 |
| Hamster 1.3 | 60 | DIVMTQSPSS LAVSAGEKVT ISCLSSQSLF SSNTNRNYLN |
| IGKV4-1*01 | 61 | DIVMTQSP<u>DS</u> LAVS<u>L</u>GE<u>RAT</u> IN<u>CK</u>SSQS<u>VL</u> <u>YSSNN</u>KNYL<u>A</u> |
| IGKV2D-28*01 | 62 | DIVMTQSP<u>LS</u> <u>LPVTPGEPAS</u> ISC<u>R</u>SSQSL<u>L</u> <u>H</u>SN-<u>GY</u>NYL<u>D</u> |
| | |           50           60          70          80 |
| Hamster 1.3 | 63 | WYLQKPGQSP KLLIYHASTR LTGVPDRFIG SGSGTDFTLT |
| IGKV4-1*01 | 64 | WY<u>QQ</u>KPGQ<u>PP</u> KLLIY<u>W</u>ASTR <u>ES</u>GVPDRF<u>SG</u> SGSGTDFTLT |
| IGKV2D-28*01 | 65 | WYLQKPGQSP <u>Q</u>LLIY<u>LGSN</u>R <u>AS</u>GVPDRF<u>SG</u> SGSGTDFTL<u>K</u> |
| | |           90         100        110 |
| Hamster 1.3 | 66 | ISSVQAEDLG DYYCQHHYET PLTFGDGTKL EIK |
| IGKV4-1*01 | 67 | ISS<u>L</u>QAED<u>VA</u> <u>V</u>YYCQ<u>QYY</u>S<u>T</u> P<u>Y</u>T |
| IGKV2D-28*01 | 68 | IS<u>RVE</u>AED<u>V</u>G <u>V</u>YYC<u>MQALQ</u>T P<u>Y</u>T |
| IGKJ2*01 | 69 |                               FG<u>Q</u>GTKL EIK |

The heavy chain of hamster antibody 1.3 was found to be most similar to the germline IGHV4-31*02. In the top 50 closest germlines to antibody 1.3 heavy chain, none of the CDR H3 have the same length as the 1.3 heavy chain. Therefore, a rearranged heavy chain was selected as the second acceptor framework (AAY33199.1) based on overall similarity, CDR lengths, and CDR canonical structures. The J-segment genes were compared to the Parental sequence over FR4 and J-segments, and IGHJ3*01 was selected for the heavy chain. Alignment of the parental VH chain to these acceptor frameworks is shown in Table 7, with non-identical residues shown underlined.

TABLE 7

| Variable Heavy Chain | SEQ ID # | Sequence |
|---|---|---|
| | |           10           20          30          40 |
| Hamster 1.3 | 70 | QIQLQESGPG LVKPSQSLSL TCSVTGFSIS TSGYYWTWIR |
| IGHV4-31*02 | 71 | Q<u>V</u>QLQESGPG LVKPSQ<u>T</u>LSL TC<u>TV</u><u>SG</u>GSIS <u>SG</u>GYYWSWIR |
| AAY33199.1 | 72 | Q<u>V</u>QLQESGPG LVKP<u>A</u>Q<u>T</u>LSL TC<u>TV</u><u>SG</u>GSIS <u>SVN</u>YYWSWIR |
| | |           50           60          70          80 |
| Hamster 1.3 | 73 | QFPGKRLEWM GYINYGGGTS YNPSLKSRIS ITRDTSKNQF |
| IGHV4-31*02 | 74 | Q<u>H</u>PGK<u>GLEWI</u> GYI<u>YY</u>SG<u>STY</u> YNPSLKSR<u>VT</u> IS<u>V</u>DTSKNQF |
| AAY33199.1 | 75 | Q<u>YP</u>GK<u>GLEWI</u> GYI<u>YY</u>RG<u>STY</u> YNPSLKSR<u>VT</u> IS<u>V</u>DTSKNQF |
| | |           90         100        110       120 |
| Hamster 1.3 | 76 | LLHLNSVTTE DTATYCCATM ADRFAFFDVW GQGIQVTVSS |
| IGHV4-31*02 | 77 | <u>SLKLS</u>SVT<u>AA</u> DTA<u>VYY</u>C<u>A</u>R |
| AAY33199.1 | 78 | <u>SLKLT</u>SVT<u>AA</u> DTA<u>VY</u>HC<u>A</u>R<u>E</u> <u>RTMTGA</u>F<u>DI</u>W GQGT<u>M</u>VTVSS |
| IGHJ3*01 | 79 |                                DA<u>F</u>DVW GQGT<u>M</u>VTVSS |

For the light chain, three humanized chains were created for each of the two acceptor frameworks IGKV4-1*01 and IGKV2D-28*01 to thereby form six humanized 1.3 light chains. The first humanized chain for each acceptor framework (VL1A, VL2A) contains the most human framework (Humanized Light Chain 1). The second humanized chain for each acceptor framework (VL1B, VL2B) contains some amount of parental sequence fused with the human framework sequence, which should help retain the original CDR conformation (Humanized Light Chain 2). The third humanized chain for each of the acceptor frameworks (VL1C, VL2C) contains even more parental sequence fused with the human framework, which should help maintain the original antibody specificity and CDR structure (Humanized Light Chain 3). The amino acid sequences of these chains are as indicated below.

Amino Acid Sequences of the Light Chain Variable Region of the humanized variants of anti-human H7CR antibody 1.3, as derived from the IGKV4-1*01 acceptor framework (CDRs are shown underlined):

1. VL1A IGKV4-1*01 (Humanized 1):
(SEQ ID NO: 17)
DIVMTQSPDS LAVSLGERAT INCKSSQSLF SSNTNRNYLA

WYQQKPGQPP KLLIYHASTR ESGVPDRFSG SGSGTDFTLT

ISSLQAEDVA VYYCQHHYET PLTFGQGTKL EIK

2. VL1B IGKV4-1*01 (Humanized 2):
(SEQ ID NO: 18)
DIVMTQSPDS LAVSLGERAT INCKSSQSLF SSNTNRNYLN

WYQQKPGQSP KLLIYHASTR LSGVPDRFSG SGSGTDFTLT

ISSLQAEDVA DYYCQHHYET PLTFGDGTKL EIK

3. VL1C IGKV4-1*01 (Humanized 3):
(SEQ ID NO: 19)
DIVMTQSPDS LAVSLGERAT INCLSSQSLF SSNTNRNYLN

WYLQKPGQSP KLLIYHASTR LSGVPDRFIG SGSGTDFTLT

ISSLQAEDVG DYYCQHHYET PLTFGDGTKL EIK

Amino Acid Sequences of the Light Chain Variable Region of the humanized variants of anti-human H7CR antibody 1.3, as derived from the IGKV2D-28*01 acceptor framework (CDRs are shown underlined):

1. VL2A IGKV2D-28*01 (Humanized 1):
(SEQ ID NO: 20)
DIVMTQSPLS LPVTPGEPAS ISCRSSQSLF SSNTNRNYLD

WYLQKPGQSP QLLIYHASNR ASGVPDRFSG SGSGTDFTLK

ISRVEAEDVG VYYCQHHYET PLTFGDGTKL EIK

2. VL2B IGKV2D-28*01 (Humanized 2):
(SEQ ID NO: 21)
DIVMTQSPLS LPVTPGEPAS ISCRSSQSLF SSNTNRNYLN

WYLQKPGQSP KLLIYHASTR ASGVPDRFSG SGSGTDFTLK

ISRVEAEDVG VYYCQHHYET PLTFGDGTKL EIK

3. VL2C IGKV2D-28*01 (Humanized 3):
(SEQ ID NO: 22)
DIVMTQSPLS LPVTPGEPAS ISCLSSQSLF SSNTNRNYLN

WYLQKPGQSP KLLIYHASTR LSGVPDRFSG SGSGTDFTLK

ISRVEAEDVG DYYCQHHYET PLTFGDGTKL EIK

For the heavy chain, three humanized chains were created for each of the IGHV4-31*02 and AAY33199.1 acceptor frameworks identified above. In a similar fashion to the light chain, the first humanized chain for each acceptor framework (VH1A, VH2A) contains the most human sequence (Humanized 1). The second humanized chain for each acceptor framework (VH1B, VH2B) should help retain the original CDR conformation (Humanized 2). The third chain for each of the acceptor frameworks (VH1C, VH2C) should help maintain the original antibody specificity and CDR structure (Humanized 3). The amino acid sequences of these chains are as indicated below.

Amino Acid Sequences of the Heavy Chain Variable Region of the humanized variants of anti-human H7CR antibody 1.3, as derived from the IGHV4-31*02 acceptor framework (CDRs are shown underlined):

1. VH1A IGHV4-31*02 (Humanized 1):
(SEQ ID NO: 23)
QVQLQESGPG LVKPSQTLSL TCTVSGFSIS TSGYYWSWIR

QHPGKGLEWI GYINYGGGTY YNPSLKSRVT ISVDTSKNQF

SLKLSSVTAA DTAVYYCATM ADRFAFFDVW GQGTMVTVSS

2. VH1B IGHV4-31*02 (Humanized 2):
(SEQ ID NO: 24)
QVQLQESGPG LVKPSQTLSL TCTVSGFSIS TSGYYWSWIR

QHPGKRLEWI GYINYGGGTS YNPSLKSRVT ISRDTSKNQF

SLKLSSVTAA DTAVYCCATM ADRFAFFDVW GQGTMVTVSS

3. VH1C IGHV4-31*02 (Humanized 3):
(SEQ ID NO: 25)
QVQLQESGPG LVKPSQTLSL TCTVSGFSIS TSGYYWSWIR

QFPGKRLEWM GYINYGGGTS YNPSLKSRVT ISRDTSKNQF

SLKLSSVTAA DTATYCCATM ADRFAFFDVW GQGTMVTVSS

Amino Acid Sequences of the Heavy Chain Variable Region of the humanized variants of anti-human H7CR antibody 1.3, as derived from the AAY33199.1 acceptor framework (CDRs are shown underlined):

1. VH2A AAY33199.1 (Humanized 1):
(SEQ ID NO: 26)
QVQLQESGPG LVKPAQTLSL TCTVSGFSIS TSGYYWSWIR

QYPGKGLEWI GYINYGGGTY YNPSLKSRVT ISVDTSKNQF

SLKLTSVTAA DTAVYHCATM ADRFAFFDVW GQGTMVTVSS

2. VH2B AAY33199.1 (Humanized 2):
(SEQ ID NO: 27)
QVQLQESGPG LVKPAQTLSL TCTVSGFSIS TSGYYWSWIR

QYPGKRLEWI GYINYGGGTS YNPSLKSRVT ISRDTSKNQF

SLKLTSVTAA DTATYCCATM ADRFAFFDVW GQGTMVTVSS

3. VH2C AAY33199.1 (Humanized 3):
(SEQ ID NO: 28)
QVQLQESGPG LVKPAQTLSL TCTVSGFSIS TSGYYWSWIR

QFPGKRLEWM GYINYGGGTS YNPSLKSRVT ISRDTSKNQF

SLKLTSVTAA DTATYCCATM ADRFAFFDVW GQGTMVTVSS

Preferred antibodies and their antigen-binding fragments include any of the 36 combinations of the above-described humanized variants of anti-human H7CR antibody 1.3. Specifically, such antibodies contain the combinations shown in Table 4. All 36 such humanized variants of anti-human H7CR antibody 1.3 were evaluated for their respective ability to bind human H7CR molecules as ectopically expressed on the surface of a CHO cell and 28 out of 36 are found to be able to bind to such human H7CR molecules.

Humanization of Anti-H7CR Antibody 4.5

Sequence alignments comparing hamster antibody 4.5 variable domains to the human germline database were generated. Based on the overall sequence identity, matching interface position, and similarly classed CDR canonical positions, two germline families were identified as possible acceptor frameworks for the light chain: IGKV4-1*01 and IGKV2D-40*01. The J-segment genes were compared to the parental sequence over FR4 and J-segments, and IGKJ5*01 was selected for the light chain. Alignment of the parental 1.3 VL chain to these acceptor frameworks is shown in Table 8, with non-identical residues shown underlined.

TABLE 8

| Variable Light Chain | SEQ ID # | Sequence |
|---|---|---|
| | | 10         20         30         40 |
| Hamster 4.5 | 80 | DIVMTQSPSS LAVSAGEKVT ISCLSSQSLF SSNTKRNYLN |
| IGKV4-1*01 | 81 | DIVMTQSPDS LAVSLGERAT INCKSSQSVL YSSNNKNYLA |
| IGKV2D-40*01 | 82 | DIVMTQTPLS LPVTPGEPAS ISCRSSQSLL DSDDGNTYLD |
| | | 50         60         70         80 |
| Hamster 4.5 | 83 | WYLQKPGQSP KLLIYHASTR LTGVPGRFIG SGSGTDFTLT |
| IGKV4-1*01 | 84 | WYQQKPGQPP KLLIYWASTR ESGVPDRFSG SGSGTDFTLT |
| IGKV2D-40*01 | 85 | WYLQKPGQSP QLLIYTLSYR ASGVPDRFSG SGSGTDFTLK |
| | | 90         100         110 |
| Hamster 4.5 | 86 | VSTVQAEDLG DYFCQQHYET PLTFGDGTRL EIK |
| IGKV4-1*01 | 87 | ISSLQAEDVA VYYCQQYYST PYT |
| IGKV2D-40*01 | 88 | ISRVEAEDVG VYYCMQRIEF P |
| IGKJ5*01 | 89 | ITFGQGTRL EIK |

The heavy chain of hamster antibody 4.5 was found to be most similar to the germline IGHV4-31*02. In the top 50 closest germlines to antibody 4.5 heavy chain, the second acceptor framework that had a similar canonical structure is IGHV2-5*01. The J-segment genes were compared to the Parental sequence over FR4 and J-segments, and IGHJ5*01 was selected for the heavy chain. Alignment of the parental VH chain to these acceptor frameworks is shown in Table 9, with non-identical residues shown underlined.

TABLE 9

| Variable Heavy Chain | SEQ ID # | Sequence |
|---|---|---|
| | | 10         20         30         40 |
| Hamster 4.5 | 90 | QIQLQESGPG LVKPSQSLSL TCSVTGFSIT TGGYYWNWIR |
| IGHV4-31*02 | 91 | QVQLQESGPG LVKPSQTLSL TCTVSGGSIS SGGYYWSWIR |
| IGHV2-5*01 | 92 | QITLKESGPT LVKPTQTLTL TCTFSGFSLS TSGVGVGWIR |
| | | 50         60         70         80 |
| Hamster 4.5 | 93 | QFPGKKLEWM GYIYTSGRTS YNPSLKSRIS ITRDTSKNQF |
| IGHV4-31*02 | 94 | QHPGKGLEWI GYIYYSGSTY YNPSLKSRVT ISVDTSKNQF |
| IGHV2-5*01 | 95 | QPPGKALEWL ALIYWNDDKR YSPSLKSRLT ITKDTSKNQV |
| | | 90         100         110         120 |
| Hamster 4.5 | 96 | FLQLNSMTTE DTATYYCADM ADKGGWFAYW GQGTLVTVSS |
| IGHV4-31*02 | 97 | SLKLSSVTAA DTAVYYCA-- --R |

TABLE 9-continued

| Variable Heavy Chain | SEQ ID # | Sequence |
|---|---|---|
| IGHV2-5*01 | 98 | VLTMTNMDPV DTATYYCA-- --HR |
| IGHJ5*01 | 99 | NWFDSW GQGTLVTVSS |

For the light chain, three humanized chains were created for each of the two acceptor frameworks IGKV4-1*01 and IGKV2D-40*01 to thereby form six humanized 4.5 light chains. The first humanized chain for each acceptor framework (VL1A, VL2A) contains the most human framework (Humanized Light Chain 1). The second humanized chain for each acceptor framework (VL1B, VL2B) contains some amount of parental sequence fused with the human framework sequence, which should help retain the original CDR conformation (Humanized Light Chain 2). The third humanized chain for each of the acceptor frameworks (VL1C, VL2C) contains even more parental sequence fused with the human framework, which should help maintain the original antibody specificity and CDR structure (Humanized Light Chain 3). The amino acid sequences of these chains are as indicated below.

Amino Acid Sequences of the Light Chain Variable Region of the humanized variants of anti-human H7CR antibody 4.5, as derived from the IGKV4-1*01 acceptor framework (CDRs are shown underlined):

1. VL1A IGKV4-1*01 (Humanized 1):
(SEQ ID NO: 33)
DIVMTQSPDS LAVSLGERAT INCKSSQSLF SSNTKRNYLA

WYQQKPGQPP KLLIYHASTR ESGVPDRFSG SGSGTDFTLT

ISSLQAEDVA VYYCQQHYET PLTFGQGTRLEIK

2. VL1B IGKV4-1*01 (Humanized 2):
(SEQ ID NO: 34)
DIVMTQSPDS LAVSLGERAT INCKSSQSLF SSNTKRNYLN

WYQQKPGQPP KLLIYHASTR LSGVPDRFSG SGSGTDFTLT

ISSLQAEDVA DYFCQQHYET PLTFGDGTRL EIK

3. VL1C IGKV4-1*01 (Humanized 3):
(SEQ ID NO: 35)
DIVMTQSPDS LAVSLGERAT INCLSSQSLF SSNTKRNYLN

WYQQKPGQSP KLLIYHASTR LSGVPDRFSG SGSGTDFTLT

ISSLQAEDVA DYFCQQHYET PLTFGDGTRL EIK

Amino Acid Sequences of the Light Chain Variable Region of the humanized variants of anti-human H7CR antibody 4.5, as derived from the IGKV2D-40*01 acceptor framework (CDRs are shown underlined):

1. VL2A IGKV2D-40*01 (Humanized 1):
(SEQ ID NO: 36)
DIVMTQTPLS LPVTPGEPAS ISCRSSQSLF SSNTKRNYLD

WYLQKPGQSP QLLIYHASYR ASGVPDRFSG SGSGTDFTLK

ISRVEAEDVG VYYCQQHYET PLTFGQGTRL EIK

2. VL2B IGKV2D-40*01 (Humanized 2):
(SEQ ID NO: 37)
DIVMTQTPLS LPVTPGEPAS ISCRSSQSLF SSNTKRNYLN

WYLQKPGQSP KLLIYHASTR LSGVPDRFSG SGSGTDFTLK

ISRVEAEDVG DYFCQQHYET PLTFGDGTRL EIK

3. VL2C IGKV2D-40*01 (Humanized 3):
(SEQ ID NO: 38)
DIVMTQTPSS LPVTPGEPAS ISCLSSQSLF SSNTKRNYLN

WYLQKPGQSP KLLIYHASTR LSGVPDRFSG SGSGTDFTLK

ISRVEAEDVG DYFCQQHYET PLTFGDGTRL EIK

For the heavy chain, three humanized chains were created for each of the IGHV4-31*02 and IGHV2-5*01 acceptor frameworks identified above. In a similar fashion to the light chain, the first humanized chain for each acceptor framework (VH1A, VH2A) contains the most human sequence (Humanized 1). The second humanized chain for each acceptor framework (VH1B, VH2B) should help retain the original CDR conformation (Humanized 2). The third chain for each of the acceptor frameworks (VH1C, VH2C) should help maintain the original antibody specificity and CDR structure (Humanized 3). The amino acid sequences of these chains are as indicated below.

Amino Acid Sequences of the Heavy Chain Variable Region of the humanized variants of anti-human H7CR antibody 4.5, as derived from the IGHV4-31*02 acceptor framework (CDRs are shown underlined):

1. VH1A IGHV4-31*02 (Humanized 1):
(SEQ ID NO: 39)
QVQLQESGPG LVKPSQTLSL TCTVSGFSIT TGGYYWSWIR

QHPGKGLEWI GYIYTSGRTY YNPSLKSRVT ISVDTSKNQF

SLKLSSVTAA DTAVYYCADM ADKGGWFAYW GQGTLVTVSS

2. VH1B IGHV4-31*02 (Humanized 2):
(SEQ ID NO: 40)
QVQLQESGPG LVKPSQTLSL TCTVSGFSIT TGGYYWNWIR

QHPGKKLEWI GYIYTSGRTS YNPSLKSRVT ISRDTSKNQF

SLKLSSVTAA DTAVYYCADM ADKGGWFAYW GQGTLVTVSS

-continued

3. VH1C IGHV4-31*02 (Humanized 3):
(SEQ ID NO: 41)
QVQLQESGPG LVKPSQTLSL TCTVSGFSIT TGGYYWNWIR

QFPGKKLEWM GYIYTSGRTS YNPSLKSRVT ISRDTSKNQF

SLKLSSVTAA DTAVYYCADM ADKGGWFAYW GQGTLVTVSS

Amino Acid Sequences of the Heavy Chain Variable Region of the humanized variants of anti-human H7CR antibody 4.5 as derived from the IGHV2-5*01 acceptor framework (CDRs are shown underlined):

1. VH2A IGHV2-5*01 (Humanized 1):
(SEQ ID NO: 42)
QITLKESGPT LVKPTQTLTL TCTFSGFSIT TGGYYVGWIR

QPPGKALEWL ALIYTSGRTR YSPSLKSRLT ITKDTSKNQV

VLTMTNMDPV DTATYYCADM ADKGGWFAYW GQGTLVTVSS

2. VH2B IGHV2-5*01 (Humanized 2):
(SEQ ID NO: 43)
QITLKESGPT LVKPTQTLTL TCTVSGFSIT TGGYYWNWIR

QPPGKKLEWL ALIYTSGRTS YNPSLKSRLT ITKDTSKNQV

VLTMTNMDPV DTATYYCADM ADKGGWFAYW GQGTLVTVSS

3. VH2C IGHV2-5*01 (Humanized 3):
(SEQ ID NO: 44)
QIQLKESGPT LVKPTQTLTL TCTVSGFSIT TGGYYWNWIR

QPPGKKLEWM ALIYTSGRTS YNPSLKSRLT ITKDTSKNQV

VLTMTNMDPV DTATYYCADM ADKGGWFAYW GQGTLVTVSS

Preferred antibodies and their antigen-binding fragments include any of the 36 combinations of the above-described humanized variants of anti-human H7CR antibody 4.5. Specifically, such antibodies include the combinations shown in Table 5. All 36 such humanized variants of anti-human H7CR antibody 4.5 are evaluated for their respective ability to bind human H7CR molecules as endogenously expressed on the surface of a cell and all are found to be able to bind to such human H7CR molecules.

Example 5

Antibody 1.3 Increases T Cell Functionality In Vivo

Materials and Methods

NOD-SCID Il2rg−/− (NSG) mice (Jackson Lab) were intraperitoneally transferred with 15~20 million human PBMCs or 10 million purified naïve CD4+ human T cells. On day 0 and day 2, each mouse was inoculated peritoneally with 300 μg control or H7CR mAb 1.3. 6 days after transfer, splenocytes were harvested. Human T cells were detected by staining for human CD45, CD3, and CD8. To monitor cell division, hPBMCs were labeled with CFSE before transfer.

Results

Flow cytometric analysis revealed that antibody 1.3 expanded human anti-mouse xeno-reactive T cells as evidenced by increased population of CFSE diluted population in both human CD4+ and CD8+ T cells. (FIGS. 19A-19D)

Example 6

Antibody 1.3 Increase CD40L, IFNγ, and CD107a Expression In Vivo: Xeno GvDH Model Materials and Methods NOD-SCID Il2rg−/− (NSG) mice (Jackson Lab) were intraperitoneally transferred with 15~20 million human PBMCs or 10 million purified naïve CD4+ human T cells. On day 0 and day 2, each mouse was inoculated peritoneally with 300 μg control or H7CR mAb 1.3. 6 days after transfer, splenocytes were harvested. Human T cells were detected by staining for human CD45, CD3, and CD8. Splenocytes were restimulated in vitro with PMA plus ionomycin to detect IFN-γ or CD107a-producing cells. To monitor cell division, hPBMCs were labeled with CF SE before transfer.

Results

FIGS. 20A-20H are scatter plots of FACS analysis showing increased expression of CD40L, IFNγ and CD107a in an NGS mouse injected with antibody 1.3. 1.3 antibody significantly enhanced CD4+ T cell expression of membrane-bound CD40L and IFN-γ production, compared with control antibody treated mice. 1.3 antibody treatment also increased the expression of CD107a on CD8+ T cells indicative of cytolytic activity, as well as IFN-γ-production. In summary, 1.3 antibody treatment promoted the expansion and effector function of xeno-reactive CD4+ and CD8+ T cells.

Example 7

Characterization of Variants of Antibody 1.3

Materials and Methods

100 μl 1 μg/ml H7CRECD human IgG1 Fc fusion protein diluted in PBS was immobilized on flat bottom 96 well plate (Costar 9017) overnight at 4° C. Plates were washed twice with PBS+0.1% PS-20 and blocked with 200 μl/well PBS 10% FBS at RT for 1 hr. 100 μl human IgG4 Fc chimeric 1.3 and 14 selected 1.3 humanized variants diluted in PBS 10% FBS were added to each well and incubated at RT for 1 hr. Plates were washed three times and 100 μl 1 μg/ml anti-human IgG4 HRP (Southern Biotech) was added to each well and incubated at RT for 1 hr. Plates were washed six times and 100 μl TMB substrate (SurModics) was added to each well for 5-15 mins. 100 μl stop solution (0.1M Sulfuric acid) was added to each well. Plates were read at Absorbance 450 nm by PerkinElmer EnVision 2104 Multilabel Reader.

The binding affinities for 14 variants of antibody 1.3 were investigated using an ELISA assay to a H7CR fusion protein.

Results

The binding affinity results are shown in Table 10.

TABLE 10

| ANTIBODY | HEAVY CHAIN | LIGHT CHAIN | $EC_{50}$ (nM) |
| --- | --- | --- | --- |
| chimeric |  |  | 0.055 |
| V1 | 1A | 1A | 0.84 |
|  | SEQ ID NO: 23 | SEQ ID NO: 17 |  |
| V2 | 1B | 1A | 0.23 |
|  | SEQ ID NO: 24 | SEQ ID NO: 17 |  |
| V3 | 1C | 1A | 0.38 |
|  | SEQ ID NO: 25 | SEQ ID NO: 17 |  |
| V4 | 2A | 1A | 1.08 |
|  | SEQ ID NO: 26 | SEQ ID NO: 17 |  |

TABLE 10-continued

| ANTIBODY | HEAVY CHAIN | LIGHT CHAIN | EC$_{50}$ (nM) |
|---|---|---|---|
| V5 | 2B SEQ ID NO: 27 | 1A SEQ ID NO: 17 | 0.28 |
| V6 | 2C SEQ ID NO: 28 | 1A SEQ ID NO: 17 | 0.30 |
| V7 | 1B SEQ ID NO: 24 | 1B SEQ ID NO: 18 | 1.01 |
| V8 | 1C SEQ ID NO: 25 | 1B SEQ ID NO: 18 | 0.74 |
| V9 | 2B SEQ ID NO: 27 | 1B SEQ ID NO: 18 | 2.43 |
| V10 | 2C SEQ ID NO: 28 | 1B SEQ ID NO: 18 | 1.18 |
| V11 | 1B SEQ ID NO: 24 | 1C SEQ ID NO: 19 | 1.04 |
| V12 | 1C SEQ ID NO: 25 | 1C SEQ ID NO: 19 | 0.75 |
| V13 | 2B SEQ ID NO: 27 | 1C SEQ ID NO: 19 | 0.45 |
| V14 | 2C SEQ ID NO: 28 | 1C SEQ ID NO: 19 | 0.32 |

FIGS. 21A and 21B are dot plots of resting or stimulated PMBCs treated with (from left to right) humanized antibody 1.3, negative control, OKT3, OKT3+CD28, humanized antibody-immobilized, negative control immobilized, and OKT3—immobilized. No statistically significant increases in cytokine production were observed upon exposure to human chimeric 1.3 antibody. As a result, 1.3 antibody treatment does not induce T cell cytokine storm in this in vitro setting.

The sequences for chimeric 1.3 antibody is as follows:

Heavy chain nucleic acid sequence:
(SEQ ID NO: 100)
ATGGAATGGTCCTGGGTGTTCCTGTTCTTCCTGTCCGTGACCACCGGCGT

GCACTCCCAGATCCAGCTGCAGGAATCTGGCCCTGGCCTCGTGAAGCCTT

CCCAGTCCCTGTCCCTGACCTGCAGCGTGACCGGCTTCTCCATCTCCACC

TCCGGCTACTACTGGACCTGGATCCGGCAGTTCCCTGGCAAGCGGCTGGA

ATGGATGGGCTACATCAACTACGGCGGAGGCACCTCCTACAACCCCAGCC

TGAAGTCCCGGATCTCCATCACCCGGGATACCTCCAAGAACCAGTTCCTG

CTGCACCTGAACTCCGTGACAACCGAGGACACCGCCACCTACTGCTGCGC

TACCATGGCCGACAGATTCGCCTTCTTCGACGTGTGGGGCCAGGGCATCC

AAGTGACCGTGTCCTCCGCTTCCACCAAGGGCCCCTCTGTGTTTCCTCTG

GCCCCTTGCTCCCGGTCCACCTCTGAGTCTACAGCCGCTCTGGGCTGCCT

CGTGAAAGACTACTTCCCCGAGCCCGTGACAGTGTCCTGGAACTCTGGCG

CTCTGACCTCTGGCGTGCACACCTTCCCTGCTGTGCTGCAGTCTAGCGGC

CTGTACTCCCTGTCCTCCGTCGTGACCGTGCCTTCCAGCTCTCTGGGCAC

CAAGACCTACACCTGTAACGTGGACCACAAGCCCTCCAACACCAAGGTGG

ACAAGAGAGTGGAATCTAAGTACGGCCCTCCCTGCCCCCCTTGTCCTGCC

CCTGAATTTCTGGGCGGACCCTCCGTGTTTCTGTTCCCCCCAAAGCCCAA

GGACACCCTGATGATCTCCCGGACCCCCGAAGTGACCTGCGTGGTGGTGG

ATGTGTCCCAGGAAGATCCCGAGGTGCAGTTCAATTGGTACGTGGACGGC

GTGGAAGTGCACAACGCCAAGACCAAGCCTAGAGAGGAACAGTTCAACTC

CACCTACCGGGTGGTGTCCGTGCTGACCGTGCTGCACCAGGATTGGCTGA

ACGGCAAAGAGTACAAGTGCAAGGTGTCCAACAAGGGCCTGCCCTCCAGC

ATCGAAAAGACCATCTCCAAGGCTAAGGGCCAGCCCCGCGAGCCCCAGGT

GTACACACTGCCTCCAAGCCAGGAAGAGATGACCAAGAATCAGGTGTCAC

TGACCTGTCTCGTGAAGGGCTTCTACCCCTCCGATATCGCCGTGGAATGG

GAGTCCAACGGCCAGCCCGAGAACAACTACAAGACCACCCCCCCTGTGCT

GGACTCCGACGGCTCCTTCTTTCTGTACTCTCGCCTGACCGTGGACAAGT

CCCGGTGGCAGGAAGGCAACGTGTTCTCCTGCTCTGTGATGCACGAGGCC

CTGCACAACCACTACACCCAGAAGTCCCTGAGCCTGTCCCCCGGCTGATG

A.

Light chain nucleic acid sequence:
(SEQ ID NO: 101)
ATGTCCGTGCCCACCCAGGTGCTGGGATTGCTGCTGCTGTGGCTGACCGA

CGCCAGATGCGACATCGTGATGACCCAGTCCCCCTCCTCCCTGGCTGTGT

CTGCTGGCGAGAAAGTGACCATCTCCTGCCTGTCCTCCCAGTCCCTGTTC

TCCTCCAACACCAACCGGAACTACCTGAACTGGTATCTGCAGAAGCCCGG

CCAGTCCCCTAAGCTGCTGATCTACCACGCCTCCACCAGACTGACCGGCG

TGCCCGATAGATTCATCGGCTCTGGCTCCGGCACCGACTTTACCCTGACC

ATCAGCTCCGTGCAGGCCGAGGACCTGGGCGACTACTACTGCCAGCACCA

CTACGAGACACCCCTGACCTTTGGCGACGGCACCAAGCTGGAAATCAAGC

GGACCGTGGCCGCTCCCTCCGTGTTCATCTTCCCACCTTCCGACGAGCAG

CTGAAGTCTGGCACCGCCTCTGTCGTGTGCCTGCTGAACAACTTCTACCC

CCGCGAGGCCAAGGTGCAGTGGAAGGTGGACAACGCCCTGCAGTCCGGCA

ACTCCCAGGAATCCGTGACCGAGCAGGACTCCAAGGACAGCACCTACTCC

CTGTCCAGCACCCTGACCCTGTCCAAGGCCGACTACGAGAAGCACAAGGT

GTACGCCTGCGAAGTGACCCACCAGGGCCTGTCTAGCCCCGTGACCAAGT

CTTTCAACCGGGGCGAGTGCTGATGA.

Heavy chain protein sequence:
(SEQ ID NO: 11)
MEWSWVFLFFLSVTTGVHSQIQLQESGPGLVKPSQSLSLTCSVTGFSIST

SGYYWTWIRQFPGKRLEWMGYINYGGGTSYNPSLKSRISITRDTSKNQFL

LHLNSVTTEDTATYCCATMADRFAFFDVWGQGIQVTVSSASTKGPSVFPL

APCSRSTSESTAALGCLVKDYFPEPVTVSWNSGALTSGVHTFPAVLQSSG

LYSLSSVVTVPSSSLGTKTYTCNVDHKPSNTKVDKRVESKYGPPCPPCPA

PEFLGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPSS

IEKTISKAKGQPREPQVYTLPPSQEEMTKNQVSLTCLVKGFYPSDIAVEW

ESNGQPENNYKTTPPVLDSDGSFFLYSRLTVDKSRWQEGNVFSCSVMHEA

LHNHYTQKSLSLSPG**.

Light chain protein sequence:
(SEQ ID NO: 12)
MSVPTQVLGLLLLWLTDARCDIVMTQSPSSLAVSAGEKVTISCLSSQSLF

SSNTNRNYLNWYLQKPGQSPKLLIYHASTRLTGVPDRFIGSGSGTDFTLT

ISSVQAEDLGDYYCQHHYETPLTFGDGTKLEIKRTVAAPSVFIFPPSDEQ

-continued

LKSGTASVVCLLNNFYPREAKVQWKVDNALQSGNSQESVTEQDSKDSTYS

LSSTLTLSKADYEKHKVYACEVTHQGLSSPVTKSFNRGEC**.

Example 8

Humanized H7CR Antibody 4.5 Variants

Materials and Methods

5 μg/ml antibodies from thirty-six variants were incubated with H7CR-GFP fusion protein transfected CHO cells for 30 min at room temperature. Cells were then washed twice with 2 ml flow cytometry buffer, and resuspended in 100 μl flow cytometry buffer. 1 μl anti-hIg PE secondary antibody (Biolegend) was added and incubated with the cells for 15 mins Samples were then washed and resuspended in 100 μl flow cytometry buffer. Flow Cytometry data was acquired using BD Canto (BD Biosciences) in plate format and analyzed by FlowJo software. X axis shows H7CR-GFP expression and Y axis shows variant binding to the transfectants.

Results

Thirty-six humanized variants of H7CR antibody 4.5 were assayed for binding specificity for H7CR. The results are presented in FIG. 23. All thirty-six 4.5 humanized variants maintain binding specificity to H7CR.

TABLE 11

4.5 antibody humanized variants
4.5 humanized variants

| Variant # | Heavy Chain | | Light Chain | |
|---|---|---|---|---|
| 1 | HC1-1 | (SEQ ID NO: 39) | LC1-1 | (SEQ ID NO: 33) |
| 2 | HC1-1 | (SEQ ID NO: 39) | LC1-2 | (SEQ ID NO: 34) |
| 3 | HC1-1 | (SEQ ID NO: 39) | LC1-3 | (SEQ ID NO: 35) |
| 4 | HC1-1 | (SEQ ID NO: 39) | LC2-1 | (SEQ ID NO: 36) |
| 5 | HC1-1 | (SEQ ID NO: 39) | LC2-2 | (SEQ ID NO: 37) |
| 6 | HC1-1 | (SEQ ID NO: 39) | LC2-3 | (SEQ ID NO: 38) |
| 7 | HC1-2 | (SEQ ID NO: 40) | LC1-1 | (SEQ ID NO: 33) |
| 8 | HC1-2 | (SEQ ID NO: 40) | LC1-2 | (SEQ ID NO: 34) |
| 9 | HC1-2 | (SEQ ID NO: 40) | LC1-3 | (SEQ ID NO: 35) |
| 10 | HC1-2 | (SEQ ID NO: 40) | LC2-1 | (SEQ ID NO: 36) |
| 11 | HC1-2 | (SEQ ID NO: 40) | LC2-2 | (SEQ ID NO: 37) |
| 12 | HC1-2 | (SEQ ID NO: 40) | LC2-3 | (SEQ ID NO: 38) |
| 13 | HC1-3 | (SEQ ID NO: 41) | LC1-1 | (SEQ ID NO: 33) |
| 14 | HC1-3 | (SEQ ID NO: 41) | LC1-2 | (SEQ ID NO: 34) |
| 15 | HC1-3 | (SEQ ID NO: 41) | LC1-3 | (SEQ ID NO: 35) |
| 16 | HC1-3 | (SEQ ID NO: 41) | LC2-1 | (SEQ ID NO: 36) |
| 17 | HC1-3 | (SEQ ID NO: 41) | LC2-2 | (SEQ ID NO: 37) |
| 18 | HC1-3 | (SEQ ID NO: 41) | LC2-3 | (SEQ ID NO: 38) |
| 19 | HC2-1 | (SEQ ID NO: 42) | LC1-1 | (SEQ ID NO: 33) |
| 20 | HC2-1 | (SEQ ID NO: 42) | LC1-2 | (SEQ ID NO: 34) |
| 21 | HC2-1 | (SEQ ID NO: 42) | LC1-3 | (SEQ ID NO: 35) |
| 22 | HC2-1 | (SEQ ID NO: 42) | LC2-1 | (SEQ ID NO: 36) |
| 23 | HC2-1 | (SEQ ID NO: 42) | LC2-2 | (SEQ ID NO: 37) |
| 24 | HC2-1 | (SEQ ID NO: 42) | LC2-3 | (SEQ ID NO: 38) |
| 25 | HC2-2 | (SEQ ID NO: 43) | LC1-1 | (SEQ ID NO: 33) |
| 26 | HC2-2 | (SEQ ID NO: 43) | LC1-2 | (SEQ ID NO: 34) |
| 27 | HC2-2 | (SEQ ID NO: 43) | LC1-3 | (SEQ ID NO: 35) |
| 28 | HC2-2 | (SEQ ID NO: 43) | LC2-1 | (SEQ ID NO: 36) |
| 29 | HC2-2 | (SEQ ID NO: 43) | LC2-2 | (SEQ ID NO: 37) |
| 30 | HC2-2 | (SEQ ID NO: 43) | LC2-3 | (SEQ ID NO: 38) |
| 31 | HC2-3 | (SEQ ID NO: 44) | LC1-1 | (SEQ ID NO: 33) |
| 32 | HC2-3 | (SEQ ID NO: 44) | LC1-2 | (SEQ ID NO: 34) |
| 33 | HC2-3 | (SEQ ID NO: 44) | LC1-3 | (SEQ ID NO: 35) |
| 34 | HC2-3 | (SEQ ID NO: 44) | LC2-1 | (SEQ ID NO: 36) |
| 35 | HC2-3 | (SEQ ID NO: 44) | LC2-2 | (SEQ ID NO: 37) |
| 36 | HC2-3 | (SEQ ID NO: 44) | LC2-3 | (SEQ ID NO: 38) |

The sequence data for the chimeric 4.5 antibody is as follows:

Heavy chain nucleic acid sequence:
(SEQ ID NO: 13)
ATGGAATGGTCCTGGGTGTTCCTGTTCTTCCTGTCCGTGACCACCGGCGT
GCACTCCCAGATCCAGCTGCAGGAATCTGGCCCTGGCCTCGTGAAGCCTT
CCCAGTCCCTGTCCCTGACCTGCAGCGTGACCGGCTTCTCTATCACAACC
GGCGGCTACTACTGGAACTGGATCCGGCAGTTCCCCGGCAAGAAACTGGA
ATGGATGGGCTACATCTATACCAGCGGCCGGACCTCCTACAACCCCAGCC
TGAAGTCCCGGATCTCCATCACCCGGGACACCTCCAAGAACCAGTTCTTT
CTGCAGCTGAACTCCATGACCACCGAGGACACCGCCACCTACTACTGCGC
CGACATGGCCGATAAGGGCGGATGGTTCGCTTACTGGGGCCAGGGCACAC
TCGTGACCGTGTCCTCTGCTTCCACCAAGGGCCCCTCCGTGTTTCCTCTG
GCCCCTTGCTCCAGATCCACCTCCGAGTCTACCGCCGCTCTGGGCTGCCT
CGTGAAAGACTACTTCCCCGAGCCCGTGACAGTGTCTTGGAACTCTGGCG
CCCTGACCTCTGGCGTGCACACCTTTCCAGCTGTGCTGCAGTCCTCCGGC
CTGTACTCCCTGTCCTCCGTCGTGACTGTGCCCTCCAGCTCTCTGGGCAC
CAAGACCTACACCTGTAACGTGGACCACAAGCCCTCCAACACCAAGGTGG
ACAAGCGGGTGGAATCTAAGTACGGCCCTCCCTGCCCTCCTTGCCCAGCC
CCTGAATTTCTGGGCGGACCTTCTGTGTTTCTGTTCCCCCCAAAGCCCAA
GGACACCCTGATGATCTCCCGGACCCCCGAAGTGACCTGCGTGGTGGTGG
ATGTGTCCCAGGAAGATCCCGAGGTGCAGTTCAATTGGTACGTGGACGGC
GTGGAAGTGCACAACGCCAAGACCAAGCCTAGAGAGGAACAGTTCAACTC
CACCTACCGGGTGGTGTCCGTGCTGACCGTGCTGCACCAGGATTGGCTGA
ACGGCAAAGAGTACAAGTGCAAGGTGTCCAACAAGGGCCTGCCCAGCTCC
ATCGAAAAGACCATCTCCAAGGCTAAGGGCCAGCCCCGCGAGCCCCAGGT
GTACACACTGCCTCCAAGCCAGGAAGAGATGACCAAGAATCAGGTGTCAC
TGACCTGTCTCGTGAAGGGCTTCTACCCCTCCGATATCGCCGTGGAATGG
GAGTCCAACGGCCAGCCCGAGAACAACTACAAGACCACCCCCCCTGTGCT
GGACTCCGACGGCTCCTTCTTTCTGTACTCTCGCCTGACCGTGGACAAGT
CCCGGTGGCAGGAAGGCAACGTGTTCTCCTGCTCTGTGATGCACGAGGCC
CTGCACAACCACTACACCCAGAAGTCCCTGAGCCTGTCCCCCGGCTGATG
A.

Light chain nucleic acid sequence:
(SEQ ID NO: 14)
ATGTCCGTGCCCACCCAGGTGCTGGGATTGCTGCTGCTGTGGCTGACCGA
CGCCAGATGCGACATCGTGATGACCCAGTCCCCCTCCTCCCTGGCTGTGT
CTGCTGGCGAGAAAGTGACCATCTCCTGCCTGTCCTCCCAGTCCCTGTTC
TCCAGCAACACCAAGCGGAACTACCTGAACTGGTATCTGCAGAAGCCCGG
CCAGTCCCCTAAGCTGCTGATCTACCACGCCTCCACCAGACTGACCGGCG
TGCCCGGAAGATTCATCGGCTCTGGCTCTGGCACCGACTTCACCCTGACC
GTGTCTACCGTGCAGGCCGAGGACCTGGGCGACTACTTCTGCCAGCAGCA
CTACGAGACACCCCTGACCTTTGGCGACGGCACCCGGCTGGAAATCAAGA

```
GAACCGTGGCCGCTCCCTCCGTGTTCATCTTCCCACCTTCCGACGAGCAG

CTGAAGTCCGGCACCGCTTCTGTCGTGTGCCTGCTGAACAACTTCTACCC

CCGCGAGGCCAAGGTGCAGTGGAAGGTGGACAACGCCCTGCAGTCCGGCA

ACTCCCAGGAATCCGTGACCGAGCAGGACTCCAAGGACAGCACCTACTCC

CTGTCCTCTACCCTGACCCTGAGCAAGGCCGACTACGAGAAGCACAAGGT

GTACGCCTGCGAAGTGACCCACCAGGGCCTGTCTAGCCCCGTGACCAAGT

CTTTCAACCGGGGCGAGTGCTGATGA.
```

Heavy chain protein sequence:

(SEQ ID NO: 15)

```
MEWSWVFLFFLSVTTGVHSQIQLQESGPGLVKPSQSLSLTCSVTGFSITT

GGYYWNWIRQFPGKKLEWMGYIYTSGRTSYNPSLKSRISITRDTSKNQFF

LQLNSMTTEDTATYYCADMADKGGWFAYWGQGTLVTVSSASTKGPSVFPL

APCSRSTSESTAALGCLVKDYFPEPVTVSWNSGALTSGVHTFPPAVLQSSG

LYSLSSVVTVPSSSLGTKTYTCNVDHKPSNTKVDKRVESKYGPPCPPCPA

PEFLGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPSS

IEKTISKAKGQPREPQVYTLPPSQEEMTKNQVSLTCLVKGFYPSDIAVEW

ESNGQPENNYKTTPPVLDSDGSFFLYSRLTVDKSRWQEGNVFSCSVMHEA

LHNHYTQKSLSLSPG**.
```

Light chain protein sequence:

(SEQ ID NO: 16)

```
MSVPTQVLGLLLLWLTDARCDIVMTQSPSSLAVSAGEKVTISCLSSQSLF

SSNTKRNYLNWYLQKPGQSPKLLIYHASTRLTGVPGRFIGSGSGTDFTLT

VSTVQAEDLGDYFCQQHYETPLTFGDGTRLEIKRTVAAPSVFIFPPSDEQ

LKSGTASVVCLLNNFYPREAKVQWKVDNALQSGNSQESVTEQDSKDSTYS

LSSTLTLSKADYEKHKVYACEVTHQGLSSPVTKSFNRGEC**.
```

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

We claim:

1. A humanized antibody or an antigen-binding fragment thereof that specifically binds to human H7CR, comprising:

(A) (1) a light chain variable region having the amino acid sequence of any of SEQ ID NOS: 17-22; and
(2) a heavy chain variable region having the amino acid sequence of any of SEQ ID NOS: 23-28; or (B) (1) a light chain variable region having the amino acid sequence of any of SEQ ID NOS: 33-38; and
(2) a heavy chain variable region having the amino acid sequence of any of SEQ ID NOS: 39-44.

2. The antibody or an antigen binding fragment thereof of claim 1, wherein the H7CR which is specifically bound is:
(A) arrayed on the surface of a live cell; or
(B) expressed at an endogenous concentration.

3. The antibody or an antigen binding fragment thereof of claim 2, wherein said live cell is a T cell, an NK cell, or a plasmacytoid dendritic cell.

4. The antibody or an antigen binding fragment thereof of claim 1, wherein the binding of the antibody or the antigen binding fragment thereof to H7CR does not block a binding interaction of B7-H7 and H7CR.

5. The antibody or an antigen binding fragment thereof of claim 1, wherein the antibody or an antigen binding fragment thereof modulates or agonizes H7CR activity.

6. The antibody or an antigen binding fragment thereof of claim 1, wherein said antibody is a bispecific or multispecific antibody.

7. The antibody or an antigen binding fragment thereof of claim 1, wherein said antibody or an antigen binding fragment thereof is detectably labeled or comprises a conjugated toxin, drug, receptor, enzyme, receptor ligand.

8. A pharmaceutical composition comprising a therapeutically effective amount of the antibody or an antigen binding fragment thereof of claim 1, and a physiologically acceptable carrier or excipient.

9. A method for enhancing an immune response in a subject in need thereof, the method comprising: administering to the subject a therapeutically effective amount of the pharmaceutical composition of claim 8.

10. The method of claim 9, wherein said subject has cancer.

11. The method of claim 9, wherein said subject has an infectious disease.

12. The method of claim 11, wherein said infectious disease is a chronic viral disease.

13. The method of claim 9, wherein said pharmaceutical composition agonizes an H7CR function.

14. The antigen-binding fragment of the anti-H7CR antibody of claim 1, wherein the antigen-binding fragment specifically binds to human H7CR as antigen.

15. The antigen-binding antibody fragment of claim 14, wherein the antigen-binding fragment specifically binds to human H7CR which is:
(A) arrayed on the surface of a live cell; or
(B) expressed at an endogenous concentration.

16. The antigen-binding antibody fragment of claim 15, wherein said live cell is a T cell, an NK cell, or a plasmacytoid dendritic cell.

17. The antigen-binding antibody fragment of claim 14, wherein the binding of the antigen-binding fragment to H7CR does not block a binding interaction of B7-H7 and H7CR.

18. The antigen-binding antibody fragment of claim 14, which is an antigen-binding fragment of a bispecific or a multispecific antibody.

19. An antigen-binding antibody fragment of a humanized anti-H7CR antibody that specifically binds to human H7CR as antigen, wherein the antigen-binding fragment comprises six CDRs, which comprise:
(A) three light chain CDRs having SEQ ID NOS: 29, 32, 45 and three heavy chain CDRs having SEQ ID NOS: 49, 52, and 56;
(B) three light chain CDRs having SEQ ID NOS: 30, 32, 46 and three heavy chain CDRs having SEQ ID NOS: 50, 53, and 57; or
(C) three light chain CDRs having SEQ ID NOS: 29, 32, 47 and three heavy chain CDRs having SEQ ID NOS: 50, 54, and 58.

20. The antigen-binding antibody fragment of claim 19, which is an antigen-binding fragment of a bispecific or multispecific antibody.

21. The antigen-binding antibody fragment of claim 19, which is detectably labeled or comprises a conjugated toxin, drug, receptor, enzyme, or receptor ligand.

22. A pharmaceutical composition comprising a therapeutically effective amount of the antigen-binding fragment of an anti-H7CR antibody of claim 14, and a physiologically acceptable carrier or excipient.

23. A method for enhancing an immune response in a subject in need thereof, the method comprising: administering to said subject a therapeutically effective amount of the pharmaceutical composition of claim 22.

24. The method of claim 23, wherein said subject has cancer.

25. The method of claim 23, wherein said subject has an infectious disease.

26. The method of claim 25, wherein said infectious disease is a chronic viral disease.

27. The method of claim 23, wherein said pharmaceutical composition agonizes an H7CR function.

28. An antigen-binding fragment of an anti-H7CR antibody that specifically binds to human H7CR, wherein said antigen-binding fragment comprises:
(A) (1) a light chain variable region having the amino acid sequence of SEQ ID NO: 5; and
(2) a heavy chain variable region having the amino acid sequence of SEQ ID NO: 6;
(B) (1) a light chain variable region having the amino acid sequence of SEQ ID NO: 7; and
(2) a heavy chain variable region having the amino acid sequence of SEQ ID NO: 8; or
(C) (1) a light chain variable region having the amino acid sequence of SEQ ID NO: 9; and
(2) a heavy chain variable region having the amino acid sequence of SEQ ID NO: 10.

29. A humanized antibody or an antigen-binding fragment thereof that specifically binds to human H7CR, comprising:
(1) a light chain variable region comprising amino acid sequence SEQ ID NO: 17 and a heavy chain variable region comprising amino acid sequence SEQ ID NO: 23;
(2) a light chain variable region comprising amino acid sequence SEQ ID NO: 17 and a heavy chain variable region comprising amino acid sequence SEQ ID NO: 24;
(3) a light chain variable region comprising amino acid sequence SEQ ID NO: 17 and a heavy chain variable region comprising amino acid sequence SEQ ID NO: 25;
(4) a light chain variable region comprising amino acid sequence SEQ ID NO: 17 and a heavy chain variable region comprising amino acid sequence SEQ ID NO: 26;
(5) a light chain variable region comprising amino acid sequence SEQ ID NO: 17 and a heavy chain variable region comprising amino acid sequence SEQ ID NO: 27;
(6) a light chain variable region comprising amino acid sequence SEQ ID NO: 17 and a heavy chain variable region comprising amino acid sequence SEQ ID NO: 28;

(7) a light chain variable region comprising amino acid sequence SEQ ID NO: 18 and a heavy chain variable region comprising amino acid sequence SEQ ID NO: 24;
(8) a light chain variable region comprising amino acid sequence SEQ ID NO: 18 and a heavy chain variable region comprising amino acid sequence SEQ ID NO: 25;
(9) a light chain variable region comprising amino acid sequence SEQ ID NO: 18 and a heavy chain variable region comprising amino acid sequence SEQ ID NO: 27;
(10) a light chain variable region comprising amino acid sequence SEQ ID NO: 18 and a heavy chain variable region comprising amino acid sequence SEQ ID NO: 28;
(11) a light chain variable region comprising amino acid sequence SEQ ID NO: 19 and a heavy chain variable region comprising amino acid sequence SEQ ID NO: 24;
(12) a light chain variable region comprising amino acid sequence SEQ ID NO: 19 and a heavy chain variable region comprising amino acid sequence SEQ ID NO: 25;
(13) a light chain variable region comprising amino acid sequence SEQ ID NO: 19 and a heavy chain variable region comprising amino acid sequence SEQ ID NO: 27; or
(14) a light chain variable region comprising amino acid sequence SEQ ID NO: 19 and a heavy chain variable region comprising amino acid sequence SEQ ID NO: 28.

30. A humanized antibody or an antigen binding fragment of an antibody that specifically binds a human H7CR, wherein the antibody or the antigen-binding fragment comprises a light chain variable region that comprises a light chain CDR1 of SEQ ID NO: 29, a light chain CDR2 of SEQ ID NO: 32 and a light chain CDR3 of SEQ ID NO: 45; and a heavy chain variable region that comprises a heavy chain CDR1 of SEQ ID NO: 49; a heavy chain CDR2 of SEQ ID NO: 52 and a heavy chain CDR3 of SEQ ID NO: 56.

31. The antibody or an antigen binding fragment thereof of claim 30, which is a bi specific or multi specific antibody.

32. The antibody or an antigen binding fragment thereof of claim 30, which is detectably labeled or comprises a conjugated toxin, drug, receptor, enzyme, or receptor ligand.

33. The antibody or an antigen binding fragment thereof of claim 30, wherein the binding of the antibody or the antigen binding fragment thereof to H7CR does not block a binding interaction of B7-H7 and H7CR.

34. A humanized antibody or an antigen binding fragment thereof that specifically binds to human H7CR, wherein said antibody or an antigen-binding fragment thereof comprises a light chain variable region comprising a light chain CDR1 of SEQ ID NO: 31, a light chain CDR2 of SEQ ID NO: 32, and a light chain CDR3 of SEQ ID NO: 48 and a heavy chain variable region comprising a heavy chain CDR1 of SEQ ID NO: 51, a heavy chain CDR2 of SEQ ID NO: 55 and a heavy chain CDR3 of SEQ ID NO: 59.

* * * * *

UNITED STATES PATENT AND TRADEMARK OFFICE
CERTIFICATE OF CORRECTION

Page 1 of 1

| | |
|---|---|
| PATENT NO. | : 9,790,277 B2 |
| APPLICATION NO. | : 14/654109 |
| DATED | : October 17, 2017 |
| INVENTOR(S) | : Solomon Langermann et al. |

It is certified that error appears in the above-identified patent and that said Letters Patent is hereby corrected as shown below:

In the Specification

Delete paragraph under STATEMENT REGARDING FEDERALLY SPONSORED RESEARCH OR DEVELOPMENT, Column 1 of the above-identified patent and replace it with the following:

STATEMENT REGARDING FEDERALLY SPONSORED RESEARCH OR DEVELOPMENT
This invention was made with government support under grant numbers CA097085, AI072592 and CA113341 awarded by the National Institutes of Health. The government has certain rights in the invention.

Signed and Sealed this
Tenth Day of April, 2018

Andrei Iancu
*Director of the United States Patent and Trademark Office*

SEQUENCE LISTING

```
<160> NUMBER OF SEQ ID NOS: 101

<210> SEQ ID NO 1
<211> LENGTH: 414
<212> TYPE: PRT
<213> ORGANISM: Homo sapiens

<400> SEQUENCE: 1

Met Lys Ala Gln Thr Ala Leu Ser Phe Phe Leu Ile Leu Ile Thr Ser
1               5                   10                  15

Leu Ser Gly Ser Gln Gly Ile Phe Pro Leu Ala Phe Phe Ile Tyr Val
                20                  25                  30

Pro Met Asn Glu Gln Ile Val Ile Gly Arg Leu Asp Glu Asp Ile Ile
            35                  40                  45

Leu Pro Ser Ser Phe Glu Arg Gly Ser Glu Val Val Ile His Trp Lys
        50                  55                  60

Tyr Gln Asp Ser Tyr Lys Val His Ser Tyr Tyr Lys Gly Ser Asp His
65                  70                  75                  80

Leu Glu Ser Gln Asp Pro Arg Tyr Ala Asn Arg Thr Ser Leu Phe Tyr
                85                  90                  95

Asn Glu Ile Gln Asn Gly Asn Ala Ser Leu Phe Phe Arg Arg Val Ser
            100                 105                 110

Leu Leu Asp Glu Gly Ile Tyr Thr Cys Tyr Val Gly Thr Ala Ile Gln
        115                 120                 125

Val Ile Thr Asn Lys Val Val Leu Lys Val Gly Val Phe Leu Thr Pro
    130                 135                 140

Val Met Lys Tyr Glu Lys Arg Asn Thr Asn Ser Phe Leu Ile Cys Ser
145                 150                 155                 160

Val Leu Ser Val Tyr Pro Arg Pro Ile Ile Thr Trp Lys Met Asp Asn
                165                 170                 175
```

```
Thr Pro Ile Ser Glu Asn Asn Met Glu Thr Gly Ser Leu Asp Ser
            180                 185                 190
Phe Ser Ile Asn Ser Pro Leu Asn Ile Thr Gly Ser Asn Ser Ser Tyr
        195                 200                 205
Glu Cys Thr Ile Glu Asn Ser Leu Leu Lys Gln Thr Trp Thr Gly Arg
    210                 215                 220
Trp Thr Met Lys Asp Gly Leu His Lys Met Gln Ser Glu His Val Ser
225                 230                 235                 240
Leu Ser Cys Gln Pro Val Asn Asp Tyr Phe Ser Pro Asn Gln Asp Phe
                245                 250                 255
Lys Val Thr Trp Ser Arg Met Lys Ser Gly Thr Phe Ser Val Leu Ala
            260                 265                 270
Tyr Tyr Leu Ser Ser Ser Gln Asn Thr Ile Ile Asn Glu Ser Arg Phe
        275                 280                 285
Ser Trp Asn Lys Glu Leu Ile Asn Gln Ser Asp Phe Ser Met Asn Leu
    290                 295                 300
Met Asp Leu Asn Leu Ser Asp Ser Gly Glu Tyr Leu Cys Asn Ile Ser
305                 310                 315                 320
Ser Asp Glu Tyr Thr Leu Leu Thr Ile His Thr Val His Val Glu Pro
                325                 330                 335
Ser Gln Glu Thr Ala Ser His Asn Lys Gly Leu Trp Ile Leu Val Pro
            340                 345                 350
Ser Ala Ile Leu Ala Ala Phe Leu Leu Ile Trp Ser Val Lys Cys Cys
        355                 360                 365
Arg Ala Gln Leu Glu Ala Arg Arg Ser Arg His Pro Ala Asp Gly Ala
    370                 375                 380
Gln Gln Glu Arg Cys Cys Val Pro Pro Gly Glu Arg Cys Pro Ser Ala
385                 390                 395                 400
Pro Asp Asn Gly Glu Glu Asn Val Pro Leu Ser Gly Lys Val
                405                 410

<210> SEQ ID NO 2
<211> LENGTH: 1242
<212> TYPE: DNA
<213> ORGANISM: Homo sapiens

<400> SEQUENCE: 2
atgaaggcac agacagcact gtctttcttc ctcattctca taacatctct gagtggatct      60
caaggcatat cccctttggc tttcttcatt tatgttccta tgaatgaaca atcgtcatt     120 ggaagacttg atgaagatat aattctccct tcttcatttg agaggggatc cgaagtcgta     180
atacactgga gtatcaaga tagctataag gttcatagtt actacaaagg cagtgaccat     240
ttggaaagcc aagatcccag atatgcaaac aggacatccc ttttctataa tgagattcaa     300
aatgggaatg cgtcactatt tttcagaaga gtaagccttc tggacgaagg aatttacacc     360
tgctatgtag aacagcaat tcaagtgatt acaaacaaag tggtgctaaa ggtgggagtt     420
tttctcacac ccgtgatgaa gtatgaaaag aggaacacaa acagcttctt aatatgcagc     480
gtgttaagtg tttatcctcg tccaattatc acgtggaaaa tggacaacac acctatctct     540
gaaaacaaca tggaagaaac agggtctttg gattcttttt ctattaacag cccactgaat     600
attacaggat caattcatc ttatgaatgt acaattgaaa attcactgct gaagcaaaca     660
tggacagggc gctggacgat gaaagatggc cttcataaaa tgcaaagtga acacgtttca     720
ctctcatgtc aacctgtaaa tgattatttt tcaccaaacc aagacttcaa agttacttgg     780
```

|  |  |
|---|---|
| tccagaatga aaagtgggac tttctctgtc ctggcttact atctgagctc ctcacaaaat | 840 |
| acaattatca atgaatcccg attctcatgg aacaaagagc tgataaacca gagtgacttc | 900 |
| tctatgaatt tgatggatct taatctttca gacagtgggg aatatttatg caatatttct | 960 |
| tcggatgaat atactttact taccatccac acagtgcatg tagaaccgag ccaagaaaca | 1020 |
| gcttcccata caaaggctt atggattttg gtgccctctg cgattttggc agcttttctg | 1080 |
| ctgatttgga gcgtaaaatg ttgcagagcc cagctagaag ccaggaggag cagacaccct | 1140 |
| gctgatggag cccaacaaga aagatgttgt gtccctcctg gtgagcgctg tcccagtgca | 1200 |
| cccgataatg gcgaagaaaa tgtgcctctt tcaggaaaag ta | 1242 |

<210> SEQ ID NO 3
<211> LENGTH: 282
<212> TYPE: PRT
<213> ORGANISM: Homo sapiens

<400> SEQUENCE: 3

Met Gly Ser Pro Gly Met Val Leu Gly Leu Leu Val Gln Ile Trp Ala
1               5                   10                  15

Leu Gln Glu Ala Ser Ser Leu Ser Val Gln Gln Gly Pro Asn Leu Leu
            20                  25                  30

Gln Val Arg Gln Gly Ser Gln Ala Thr Leu Val Cys Gln Val Asp Gln
        35                  40                  45

Ala Thr Ala Trp Glu Arg Leu Arg Val Lys Trp Thr Lys Asp Gly Ala
    50                  55                  60

Ile Leu Cys Gln Pro Tyr Ile Thr Asn Gly Ser Leu Ser Leu Gly Val
65                  70                  75                  80

Cys Gly Pro Gln Gly Arg Leu Ser Trp Gln Ala Pro Ser His Leu Thr
                85                  90                  95

Leu Gln Leu Asp Pro Val Ser Leu Asn His Ser Gly Ala Tyr Val Cys
            100                 105                 110

Trp Ala Val Glu Ile Pro Glu Leu Glu Ala Glu Gly Asn Ile
        115                 120                 125

Thr Arg Leu Phe Val Asp Pro Asp Pro Thr Gln Asn Arg Asn Arg
    130                 135                 140

Ile Ala Ser Phe Pro Gly Phe Leu Phe Val Leu Leu Gly Val Gly Ser
145                 150                 155                 160

Met Gly Val Ala Ala Ile Val Trp Gly Ala Trp Phe Trp Gly Arg Arg
                165                 170                 175

Ser Cys Gln Gln Arg Asp Ser Gly Asn Ser Pro Gly Asn Ala Phe Tyr
            180                 185                 190

Ser Asn Val Leu Tyr Arg Pro Arg Gly Ala Pro Lys Lys Ser Glu Asp
        195                 200                 205

Cys Ser Gly Glu Gly Lys Asp Gln Arg Gly Gln Ser Ile Tyr Ser Thr
    210                 215                 220

Ser Phe Pro Gln Pro Ala Pro Arg Gln Pro His Leu Ala Ser Arg Pro
225                 230                 235                 240

Cys Pro Ser Pro Arg Pro Cys Pro Ser Pro Arg Pro Gly His Pro Val
                245                 250                 255

Ser Met Val Arg Val Ser Pro Arg Ser Pro Thr Gln Gln Pro Arg
            260                 265                 270

Pro Lys Gly Phe Pro Lys Val Gly Glu Glu
        275                 280

<210> SEQ ID NO 4
<211> LENGTH: 846
<212> TYPE: DNA
<213> ORGANISM: Homo sapiens

<400> SEQUENCE: 4

```
atgggqtccc cgggcatggt gctgggcctc ctggtgcaga tctgggccct gcaagaagcc      60
tcaagcctga gcgtgcagca ggggcccaac ttgctgcagg tgaggcaggg cagtcaggcg     120
accctggtct gccaggtgga ccaggccaca gcctgggaac ggctccgtgt taagtggaca     180
aaggatgggg ccatcctgtg tcaaccgtac atcaccaacg gcagcctcag cctggggggtc   240
tgcgggcccc agggacggct ctcctggcag gcacccagcc atctcaccct gcagctggac     300
cctgtgagcc tcaaccacag cggggcgtac gtgtgctggg cggccgtaga gattcctgag     360
ttggaggagg ctgagggcaa cataacaagg ctctttgtgg acccagatga ccccacacag     420
aacagaaacc ggatcgcaag cttcccagga ttcctcttcg tgctgctggg ggtgggaagc     480
atgggtgtgg ctgcgatcgt gtggggtgcc tggttctggg gccgccgcag ctgccagcaa     540
agggactcag gtaacagccc aggaaatgca ttctacagca acgtcctata ccggccccgg     600
ggggccccaa agaagagtga ggactgctct ggagagggga aggaccagag gggccagagc     660
atttattcaa cctccttccc gcaaccggcc ccccgccagc cgcacctggc gtcaagaccc     720
tgccccagcc cgagaccctg cccagcccc aggcccggcc accccgtctc tatggtcagg      780
gtctctccta gaccaagccc cacccagcag ccgaggccaa aagggttccc caaagtggga     840
gaggag                                                                846
```

<210> SEQ ID NO 5
<211> LENGTH: 113
<212> TYPE: PRT
<213> ORGANISM: Artificial Sequence
<220> FEATURE:
<223> OTHER INFORMATION: Anti-Human H7CR Antibody

<400> SEQUENCE: 5

Asp Ile Val Met Thr Gln Ser Pro Ser Ser Leu Ala Val Ser Ala Gly
1               5                   10                  15

Glu Lys Val Thr Ile Ser Cys Leu Ser Ser Gln Ser Leu Phe Ser Ser
            20                  25                  30

Asn Thr Asn Arg Asn Tyr Leu Asn Trp Tyr Leu Gln Lys Pro Gly Gln
        35                  40                  45

Ser Pro Lys Leu Leu Ile Tyr His Ala Ser Thr Arg Leu Thr Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Gly Asp Tyr Tyr Cys Gln His
                85                  90                  95

His Tyr Glu Thr Pro Leu Thr Phe Gly Asp Gly Thr Lys Leu Glu Ile
            100                 105                 110

Lys

<210> SEQ ID NO 6
<211> LENGTH: 120
<212> TYPE: PRT
<213> ORGANISM: Artificial Sequence
<220> FEATURE:
<223> OTHER INFORMATION: Anti-Human H7CR Antibody

<400> SEQUENCE: 6

Gln Ile Gln Leu Gln Glu Ser Gly Pro Gly Leu Val Lys Pro Ser Gln
1               5                   10                  15

Ser Leu Ser Leu Thr Cys Ser Val Thr Gly Phe Ser Ile Ser Thr Ser
            20                  25                  30

Gly Tyr Tyr Trp Thr Trp Ile Arg Gln Phe Pro Gly Lys Arg Leu Glu
        35                  40                  45

Trp Met Gly Tyr Ile Asn Tyr Gly Gly Thr Ser Tyr Asn Pro Ser
50                  55                  60

Leu Lys Ser Arg Ile Ser Ile Thr Arg Asp Thr Ser Lys Asn Gln Phe
65                  70                  75                  80

Leu Leu His Leu Asn Ser Val Thr Thr Glu Asp Thr Ala Thr Tyr Cys
            85                  90                  95

Cys Ala Thr Met Ala Asp Arg Phe Ala Phe Phe Asp Val Trp Gly Gln
            100                 105                 110

Gly Ile Gln Val Thr Val Ser Ser
        115                 120

<210> SEQ ID NO 7
<211> LENGTH: 113
<212> TYPE: PRT
<213> ORGANISM: Artificial Sequence
<220> FEATURE:
<223> OTHER INFORMATION: Anti-Human H7CR Antibody

<400> SEQUENCE: 7

Asp Ile Val Met Thr Gln Ser Pro Ser Ser Leu Ala Val Ser Ala Gly
1               5                   10                  15

Glu Lys Val Thr Ile Ser Cys Leu Ser Ser Gln Ser Leu Phe Ser Ser
            20                  25                  30

Asn Thr Lys Arg Asn Tyr Leu Asn Trp Tyr Leu Gln Lys Pro Gly Gln
        35                  40                  45

Ser Pro Lys Leu Leu Ile Tyr His Ala Ser Thr Arg Leu Thr Gly Val
    50                  55                  60

Pro Gly Arg Phe Ile Gly Ser Gly Ser Gly Thr Asp Phe Thr Leu Thr
65                  70                  75                  80

Val Ser Thr Val Gln Ala Glu Asp Leu Gly Asp Tyr Phe Cys Gln Gln
            85                  90                  95

His Tyr Glu Thr Pro Leu Thr Phe Gly Asp Gly Thr Arg Leu Glu Ile
        100                 105                 110

Lys

<210> SEQ ID NO 8
<211> LENGTH: 120
<212> TYPE: PRT
<213> ORGANISM: Artificial Sequence
<220> FEATURE:
<223> OTHER INFORMATION: Anti-Human H7CR Antibody

<400> SEQUENCE: 8

Gln Ile Gln Leu Gln Glu Ser Gly Pro Gly Leu Val Lys Pro Ser Gln
1               5                   10                  15

Ser Leu Ser Leu Thr Cys Ser Val Thr Gly Phe Ser Ile Thr Thr Gly
            20                  25                  30

Gly Tyr Tyr Trp Asn Trp Ile Arg Gln Phe Pro Gly Lys Lys Leu Glu
        35                  40                  45

Trp Met Gly Tyr Ile Tyr Thr Ser Gly Arg Thr Ser Tyr Asn Pro Ser
50                  55                  60

Leu Lys Ser Arg Ile Ser Ile Thr Arg Asp Thr Ser Lys Asn Gln Phe
65                  70                  75                  80

Phe Leu Gln Leu Asn Ser Met Thr Thr Glu Asp Thr Ala Thr Tyr Tyr
                85                  90                  95

Cys Ala Asp Met Ala Asp Lys Gly Gly Trp Phe Ala Tyr Trp Gly Gln
            100                 105                 110

Gly Thr Leu Val Thr Val Ser Ser
        115                 120

<210> SEQ ID NO 9
<211> LENGTH: 113
<212> TYPE: PRT
<213> ORGANISM: Artificial Sequence
<220> FEATURE:
<223> OTHER INFORMATION: Anti-Human H7CR Antibody

<400> SEQUENCE: 9

Asp Ile Val Met Thr Gln Ser Pro Ser Ser Leu Thr Val Ser Ala Gly
1               5                   10                  15

Glu Lys Val Thr Ile Ser Cys Leu Ser Ser Gln Ser Leu Phe Ser Ser
                20                  25                  30

Asn Thr Asn Arg Asn Tyr Leu Ser Trp Tyr Leu Gln Arg Pro Gly Gln
            35                  40                  45

Ser Pro Lys Leu Leu Ile Tyr His Ala Ser Thr Arg Leu Thr Gly Val
        50                  55                  60

Pro Gly Arg Phe Ile Gly Ser Gly Ser Gly Thr Asp Phe Thr Leu Thr
65                  70                  75                  80

Val Ser Thr Val Gln Ala Gly Asp Leu Gly Asp Tyr Phe Cys Gln Gln
                85                  90                  95

His Tyr Val Thr Pro Leu Thr Phe Gly Asp Gly Thr Arg Leu Glu Ile
            100                 105                 110

Lys

<210> SEQ ID NO 10
<211> LENGTH: 120
<212> TYPE: PRT
<213> ORGANISM: Artificial Sequence
<220> FEATURE:
<223> OTHER INFORMATION: Anti-Human H7CR Antibody

<400> SEQUENCE: 10

Gln Ile Gln Leu Gln Glu Ser Gly Pro Gly Leu Val Lys Pro Ser Gln
1               5                   10                  15

Ser Leu Ser Leu Thr Cys Ser Val Thr Gly Phe Ser Ile Thr Thr Gly
                20                  25                  30

Gly Tyr Tyr Trp Asn Trp Ile Arg Gln Phe Pro Gly Lys Lys Leu Glu
            35                  40                  45

Trp Met Gly Tyr Ile Tyr Ser Ser Gly Arg Thr Ser Tyr Asn Pro Ser
        50                  55                  60

Leu Lys Ser Arg Ile Ser Ile Thr Arg Asp Thr Ser Lys Asn Gln Phe
65                  70                  75                  80

Phe Leu Gln Leu Asn Ser Val Thr Thr Glu Asp Thr Ala Thr Tyr Tyr
                85                  90                  95

Cys Ala Asp Met Ala Asp Lys Gly Gly Trp Phe Asp Tyr Trp Gly Gln
            100                 105                 110

Gly Thr Leu Val Thr Val Ser Ser
        115                 120

<210> SEQ ID NO 11
<211> LENGTH: 465
<212> TYPE: PRT
<213> ORGANISM: Artificial Sequence
<220> FEATURE:
<223> OTHER INFORMATION: Humanized antibody

<400> SEQUENCE: 11

```
Met Glu Trp Ser Trp Val Phe Leu Phe Phe Leu Ser Val Thr Thr Gly
1               5                   10                  15

Val His Ser Gln Ile Gln Leu Gln Glu Ser Gly Pro Gly Leu Val Lys
            20                  25                  30

Pro Ser Gln Ser Leu Ser Leu Thr Cys Ser Val Thr Gly Phe Ser Ile
        35                  40                  45

Ser Thr Ser Gly Tyr Tyr Trp Thr Trp Ile Arg Gln Phe Pro Gly Lys
    50                  55                  60

Arg Leu Glu Trp Met Gly Tyr Ile Asn Tyr Gly Gly Thr Ser Tyr
65                  70                  75                  80

Asn Pro Ser Leu Lys Ser Arg Ile Ser Ile Thr Arg Asp Thr Ser Lys
                85                  90                  95

Asn Gln Phe Leu Leu His Leu Asn Ser Val Thr Thr Glu Asp Thr Ala
            100                 105                 110

Thr Tyr Cys Cys Ala Thr Met Ala Asp Arg Phe Ala Phe Phe Asp Val
        115                 120                 125

Trp Gly Gln Gly Ile Gln Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365
```

```
Thr Leu Pro Pro Ser Gln Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
                420                 425                 430

Lys Ser Arg Trp Gln Glu Gly Asn Val Phe Ser Cys Ser Val Met His
                435                 440                 445

Glu Ala Leu His Asn His Tyr Thr Gln Lys Ser Leu Ser Leu Ser Pro
        450                 455                 460

Gly
465

<210> SEQ ID NO 12
<211> LENGTH: 240
<212> TYPE: PRT
<213> ORGANISM: Artificial Sequence
<220> FEATURE:
<223> OTHER INFORMATION: Humanized antibody

<400> SEQUENCE: 12

Met Ser Val Pro Thr Gln Val Leu Gly Leu Leu Leu Leu Trp Leu Thr
1               5                   10                  15

Asp Ala Arg Cys Asp Ile Val Met Thr Gln Ser Pro Ser Ser Leu Ala
                20                  25                  30

Val Ser Ala Gly Glu Lys Val Thr Ile Ser Cys Leu Ser Ser Gln Ser
            35                  40                  45

Leu Phe Ser Ser Asn Thr Asn Arg Asn Tyr Leu Asn Trp Tyr Leu Gln
    50                  55                  60

Lys Pro Gly Gln Ser Pro Lys Leu Leu Ile Tyr His Ala Ser Thr Arg
65                  70                  75                  80

Leu Thr Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Gly Asp Tyr
                100                 105                 110

Tyr Cys Gln His His Tyr Glu Thr Pro Leu Thr Phe Gly Asp Gly Thr
            115                 120                 125

Lys Leu Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 13
```

```
<211> LENGTH: 1401
<212> TYPE: DNA
<213> ORGANISM: Artificial Sequence
<220> FEATURE:
<223> OTHER INFORMATION: Chimeric antibody coding sequence

<400> SEQUENCE: 13
atggaatggt cctgggtgtt cctgttcttc ctgtccgtga ccaccggcgt gcactcccag      60
atccagctgc aggaatctgg ccctggcctc gtgaagcctt cccagtccct gtccctgacc     120
tgcagcgtga ccggcttctc tatcacaacc ggcggctact actggaactg gatccggcag     180
ttccccggca agaaactgga atggatgggc tacatctata ccagcggccg gacctcctac     240
aaccccagcc tgaagtcccg gatctccatc acccgggaca cctccaagaa ccagttcttt     300
ctgcagctga actccatgac caccgaggac accgccacct actactgcgc cgacatggcc     360
gataagggcg gatggttcgc ttactggggc cagggcacac tcgtgaccgt gtcctctgct     420
tccaccaagg gccctccgt gtttcctctg gccccttgct ccagatccac ctccgagtct      480
accgccgctc tgggctgcct cgtgaaagac tacttccccg agcccgtgac agtgtcttgg     540
aactctggcg ccctgacctc tggcgtgcac acctttccag ctgtgctgca gtcctccggc     600
ctgtactccc tgtcctccgt cgtgactgtg ccctccagct ctctgggcac caagacctac     660
acctgtaacg tggaccacaa gccctccaac accaaggtgg acaagcgggt ggaatctaag     720
tacggccctc cctgccctcc ttgcccagcc cctgaatttc tgggcggacc ttctgtgttt     780
ctgttccccc caaagcccaa ggacaccctg atgatctccc ggaccccga agtgacctgc      840 gtggtggtgg atgtgtccca ggaagatccc gaggtgcagt tcaattggta cgtggacggc     900
gtggaagtgc acaacgccaa gaccaagcct agagaggaac agttcaactc cacctaccgg     960
gtggtgtccg tgctgaccgt gctgcaccag gattggctga acggcaaaga gtacaagtgc    1020
aaggtgtcca acaagggcct gcccagctcc atcgaaaaga ccatctccaa ggctaagggc    1080
cagccccgcg agccccaggt gtacacactg cctccaagcc aggaagagat gaccaagaat    1140
caggtgtcac tgacctgtct cgtgaagggc ttctacccct ccgatatcgc cgtggaatgg    1200
gagtccaacg gccagcccga gaacaactac aagaccaccc cccctgtgct ggactccgac    1260
ggctccttct ttctgtactc tcgcctgacc gtggacaagt cccggtggca ggaaggcaac    1320
gtgttctcct gctctgtgat gcacgaggcc ctgcacaacc actacaccca gaagtccctg    1380
agcctgtccc ccggctgatg a                                              1401

<210> SEQ ID NO 14
<211> LENGTH: 726
<212> TYPE: DNA
<213> ORGANISM: Artificial Sequence
<220> FEATURE:
<223> OTHER INFORMATION: Chimeric antibody coding sequence

<400> SEQUENCE: 14
atgtccgtgc ccacccaggt gctgggattg ctgctgctgt ggctgaccga cgccagatgc      60
gacatcgtga tgacccagtc ccctcctcc ctggctgtgt ctgctggcga aaagtgacc      120 atctcctgcc tgtcctccca gtccctgttc tccagcaaca ccaagcggaa ctacctgaac     180
tggtatctgc agaagcccgg ccagtcccct aagctgctga tctaccacgc ctccaccaga     240
ctgaccggcg tgcccggaag attcatcggc tctggctctg gcaccgactt caccctgacc     300
gtgtctaccg tgcaggccga ggacctgggc gactacttct gccagcagca ctacgagaca     360
cccctgacct ttggcgacgg cacccggctg gaaatcaaga gaaccgtggc cgctcccctcc     420
```

```
gtgttcatct tcccaccttc cgacgagcag ctgaagtccg gcaccgcttc tgtcgtgtgc    480
ctgctgaaca acttctaccc ccgcgaggcc aaggtgcagt ggaaggtgga caacgccctg    540
cagtccggca actcccagga atccgtgacc gagcaggact ccaaggacag cacctactcc    600
ctgtcctcta ccctgaccct gagcaaggcc gactacgaga agcacaaggt gtacgcctgc    660
gaagtgaccc ccagggcct gtctagcccc gtgaccaagt ctttcaaccg gggcgagtgc    720
tgatga                                                              726
```

<210> SEQ ID NO 15
<211> LENGTH: 465
<212> TYPE: PRT
<213> ORGANISM: Artificial Sequence
<220> FEATURE:
<223> OTHER INFORMATION: Chimeric antibody heavy chain sequence

<400> SEQUENCE: 15

```
Met Glu Trp Ser Trp Val Phe Leu Phe Phe Leu Ser Val Thr Thr Gly
  1               5                  10                  15

Val His Ser Gln Ile Gln Leu Gln Glu Ser Gly Pro Gly Leu Val Lys
             20                  25                  30

Pro Ser Gln Ser Leu Ser Leu Thr Cys Ser Val Thr Gly Phe Ser Ile
         35                  40                  45

Thr Thr Gly Gly Tyr Tyr Trp Asn Trp Ile Arg Gln Phe Pro Gly Lys
     50                  55                  60

Lys Leu Glu Trp Met Gly Tyr Ile Tyr Thr Ser Gly Arg Thr Ser Tyr
 65                  70                  75                  80

Asn Pro Ser Leu Lys Ser Arg Ile Ser Ile Thr Arg Asp Thr Ser Lys
                 85                  90                  95

Asn Gln Phe Phe Leu Gln Leu Asn Ser Met Thr Thr Glu Asp Thr Ala
            100                 105                 110

Thr Tyr Tyr Cys Ala Asp Met Ala Asp Lys Gly Gly Trp Phe Ala Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300
```

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Gln Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly
465

<210> SEQ ID NO 16
<211> LENGTH: 240
<212> TYPE: PRT
<213> ORGANISM: Artificial Sequence
<220> FEATURE:
<223> OTHER INFORMATION: Chimeric antibiody light chain

<400> SEQUENCE: 16

Met Ser Val Pro Thr Gln Val Leu Gly Leu Leu Leu Leu Trp Leu Thr
1               5                   10                  15

Asp Ala Arg Cys Asp Ile Val Met Thr Gln Ser Pro Ser Ser Leu Ala
            20                  25                  30

Val Ser Ala Gly Glu Lys Val Thr Ile Ser Cys Leu Ser Ser Gln Ser
        35                  40                  45

Leu Phe Ser Ser Asn Thr Lys Arg Asn Tyr Leu Asn Trp Tyr Leu Gln
    50                  55                  60

Lys Pro Gly Gln Ser Pro Lys Leu Leu Ile Tyr His Ala Ser Thr Arg
65                  70                  75                  80

Leu Thr Gly Val Pro Gly Arg Phe Ile Gly Ser Gly Ser Gly Thr Asp
            85                  90                  95

Phe Thr Leu Thr Val Ser Thr Val Gln Ala Glu Asp Leu Gly Asp Tyr
            100                 105                 110

Phe Cys Gln Gln His Tyr Glu Thr Pro Leu Thr Phe Gly Asp Gly Thr
            115                 120                 125

Arg Leu Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
            165                 170                 175

Asp Asn Ala Leu Gln Ser Gly Asn Ser Gln Glu Ser Val Thr Glu Gln
            180                 185                 190

-continued

```
Asp Ser Lys Asp Ser Thr Tyr Ser Leu Ser Ser Thr Leu Thr Leu Ser
            195                 200                 205
Lys Ala Asp Tyr Glu Lys His Lys Val Tyr Ala Cys Glu Val Thr His
        210                 215                 220
Gln Gly Leu Ser Ser Pro Val Thr Lys Ser Phe Asn Arg Gly Glu Cys
225                 230                 235                 240

<210> SEQ ID NO 17
<211> LENGTH: 113
<212> TYPE: PRT
<213> ORGANISM: Artificial Sequence
<220> FEATURE:
<223> OTHER INFORMATION: Variant of humanized anti-human H7CR Antibody

<400> SEQUENCE: 17

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Leu Phe Ser Ser
            20                  25                  30
Asn Thr Asn Arg Asn Tyr Leu Ala Trp Tyr Gln Gln Lys Pro Gly Gln
        35                  40                  45
Pro Pro Lys Leu Leu Ile Tyr His Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln His
                85                  90                  95
His Tyr Glu Thr Pro Leu Thr Phe Gly Gln Gly Thr Lys Leu Glu Ile
            100                 105                 110
Lys

<210> SEQ ID NO 18
<211> LENGTH: 113
<212> TYPE: PRT
<213> ORGANISM: Artificial Sequence
<220> FEATURE:
<223> OTHER INFORMATION: Variant of humanized anti-human H7CR Antibody

<400> SEQUENCE: 18

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Leu Phe Ser Ser
            20                  25                  30
Asn Thr Asn Arg Asn Tyr Leu Asn Trp Tyr Gln Gln Lys Pro Gly Gln
        35                  40                  45
Ser Pro Lys Leu Leu Ile Tyr His Ala Ser Thr Arg Leu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Asp Tyr Tyr Cys Gln His
                85                  90                  95
His Tyr Glu Thr Pro Leu Thr Phe Gly Asp Gly Thr Lys Leu Glu Ile
            100                 105                 110
Lys

<210> SEQ ID NO 19
<211> LENGTH: 113
```

```
<212> TYPE: PRT
<213> ORGANISM: Artificial Sequence
<220> FEATURE:
<223> OTHER INFORMATION: Variant of humanized anti-human H7CR Antibody

<400> SEQUENCE: 19

Asp Ile Val Met Thr Gln Ser Pro Asp Ser Leu Ala Val Ser Leu Gly
1               5                   10                  15

Glu Arg Ala Thr Ile Asn Cys Leu Ser Ser Gln Ser Leu Phe Ser Ser
            20                  25                  30

Asn Thr Asn Arg Asn Tyr Leu Asn Trp Tyr Leu Gln Lys Pro Gly Gln
        35                  40                  45

Ser Pro Lys Leu Leu Ile Tyr His Ala Ser Thr Arg Leu Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Gly Asp Tyr Tyr Cys Gln His
                85                  90                  95

His Tyr Glu Thr Pro Leu Thr Phe Gly Asp Gly Thr Lys Leu Glu Ile
            100                 105                 110

Lys

<210> SEQ ID NO 20
<211> LENGTH: 113
<212> TYPE: PRT
<213> ORGANISM: Artificial Sequence
<220> FEATURE:
<223> OTHER INFORMATION: Variant of humanized anti-human H7CR Antibody

<400> SEQUENCE: 20

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Phe Ser Ser
            20                  25                  30

Asn Thr Asn Arg Asn Tyr Leu Asp Trp Tyr Leu Gln Lys Pro Gly Gln
        35                  40                  45

Ser Pro Gln Leu Leu Ile Tyr His Ala Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln His
                85                  90                  95

His Tyr Glu Thr Pro Leu Thr Phe Gly Asp Gly Thr Lys Leu Glu Ile
            100                 105                 110

Lys

<210> SEQ ID NO 21
<211> LENGTH: 113
<212> TYPE: PRT
<213> ORGANISM: Artificial Sequence
<220> FEATURE:
<223> OTHER INFORMATION: Variant of humanized anti-human H7CR Antibody

<400> SEQUENCE: 21

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Phe Ser Ser
            20                  25                  30
```

```
Asn Thr Asn Arg Asn Tyr Leu Asn Trp Tyr Leu Gln Lys Pro Gly Gln
            35                  40                  45

Ser Pro Lys Leu Leu Ile Tyr His Ala Ser Thr Arg Ala Ser Gly Val
 50                      55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln His
                 85                  90                  95

His Tyr Glu Thr Pro Leu Thr Phe Gly Asp Gly Thr Lys Leu Glu Ile
            100                 105                 110

Lys

<210> SEQ ID NO 22
<211> LENGTH: 113
<212> TYPE: PRT
<213> ORGANISM: Artificial Sequence
<220> FEATURE:
<223> OTHER INFORMATION: Variant of humanized anti-human H7CR Antibody

<400> SEQUENCE: 22

Asp Ile Val Met Thr Gln Ser Pro Leu Ser Leu Pro Val Thr Pro Gly
 1               5                  10                  15

Glu Pro Ala Ser Ile Ser Cys Leu Ser Ser Gln Ser Leu Phe Ser Ser
             20                  25                  30

Asn Thr Asn Arg Asn Tyr Leu Asn Trp Tyr Leu Gln Lys Pro Gly Gln
            35                  40                  45

Ser Pro Lys Leu Leu Ile Tyr His Ala Ser Thr Arg Leu Ser Gly Val
 50                      55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Asp Tyr Tyr Cys Gln His
                 85                  90                  95

His Tyr Glu Thr Pro Leu Thr Phe Gly Asp Gly Thr Lys Leu Glu Ile
            100                 105                 110

Lys

<210> SEQ ID NO 23
<211> LENGTH: 120
<212> TYPE: PRT
<213> ORGANISM: Artificial Sequence
<220> FEATURE:
<223> OTHER INFORMATION: Variant of humanized anti-human H7CR Antibody

<400> SEQUENCE: 23

Gln Val Gln Leu Gln Glu Ser Gly Pro Gly Leu Val Lys Pro Ser Gln
 1               5                  10                  15

Thr Leu Ser Leu Thr Cys Thr Val Ser Gly Phe Ser Ile Ser Thr Ser
             20                  25                  30

Gly Tyr Tyr Trp Ser Trp Ile Arg Gln His Pro Gly Lys Gly Leu Glu
            35                  40                  45

Trp Ile Gly Tyr Ile Asn Tyr Gly Gly Thr Tyr Tyr Asn Pro Ser
 50                      55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Thr Met Ala Asp Arg Phe Ala Phe Phe Asp Val Trp Gly Gln
```

Gly Thr Met Val Thr Val Ser Ser
        115                 120

<210> SEQ ID NO 24
<211> LENGTH: 120
<212> TYPE: PRT
<213> ORGANISM: Artificial Sequence
<220> FEATURE:
<223> OTHER INFORMATION: Variant of humanized anti-human H7CR Antibody

<400> SEQUENCE: 24

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Ser Thr Ser
            20                  25                  30

Gly Tyr Tyr Trp Ser Trp Ile Arg Gln His Pro Gly Lys Arg Leu Glu
        35                  40                  45

Trp Ile Gly Tyr Ile Asn Tyr Gly Gly Gly Thr Ser Tyr Asn Pro Ser
    50                  55                  60

Leu Lys Ser Arg Val Thr Ile Ser Arg Asp Thr Ser Lys Asn Gln Phe
65                  70                  75                  80

Ser Leu Lys Leu Ser Ser Val Thr Ala Ala Asp Thr Ala Val Tyr Cys
                85                  90                  95

Cys Ala Thr Met Ala Asp Arg Phe Ala Phe Phe Asp Val Trp Gly Gln
            100                 105                 110

Gly Thr Met Val Thr Val Ser Ser
        115                 120

<210> SEQ ID NO 25
<211> LENGTH: 120
<212> TYPE: PRT
<213> ORGANISM: Artificial Sequence
<220> FEATURE:
<223> OTHER INFORMATION: Variant of humanized anti-human H7CR Antibody

<400> SEQUENCE: 25

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Ser Thr Ser
            20                  25                  30

Gly Tyr Tyr Trp Ser Trp Ile Arg Gln Phe Pro Gly Lys Arg Leu Glu
        35                  40                  45

Trp Met Gly Tyr Ile Asn Tyr Gly Gly Gly Thr Ser Tyr Asn Pro Ser
    50                  55                  60

Leu Lys Ser Arg Val Thr Ile Ser Arg Asp Thr Ser Lys Asn Gln Phe
65                  70                  75                  80

Ser Leu Lys Leu Ser Ser Val Thr Ala Ala Asp Thr Ala Thr Tyr Cys
                85                  90                  95

Cys Ala Thr Met Ala Asp Arg Phe Ala Phe Phe Asp Val Trp Gly Gln
            100                 105                 110

Gly Thr Met Val Thr Val Ser Ser
        115                 120

<210> SEQ ID NO 26
<211> LENGTH: 120
<212> TYPE: PRT
<213> ORGANISM: Artificial Sequence
<220> FEATURE:

<223> OTHER INFORMATION: Variant of humanized anti-human H7CR Antibody

<400> SEQUENCE: 26

```
Gln Val Gln Leu Gln Glu Ser Gly Pro Gly Leu Val Lys Pro Ala Gln
1               5                   10                  15

Thr Leu Ser Leu Thr Cys Thr Val Ser Gly Phe Ser Ile Ser Thr Ser
            20                  25                  30

Gly Tyr Tyr Trp Ser Trp Ile Arg Gln Tyr Pro Gly Lys Gly Leu Glu
        35                  40                  45

Trp Ile Gly Tyr Ile Asn Tyr Gly Gly Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Thr Ser Val Thr Ala Ala Asp Thr Ala Val Tyr His
            85                  90                  95

Cys Ala Thr Met Ala Asp Arg Phe Ala Phe Phe Asp Val Trp Gly Gln
            100                 105                 110

Gly Thr Met Val Thr Val Ser Ser
        115                 120
```

<210> SEQ ID NO 27
<211> LENGTH: 120
<212> TYPE: PRT
<213> ORGANISM: Artificial Sequence
<220> FEATURE:
<223> OTHER INFORMATION: Variant of humanized anti-human H7CR Antibody

<400> SEQUENCE: 27

```
Gln Val Gln Leu Gln Glu Ser Gly Pro Gly Leu Val Lys Pro Ala Gln
1               5                   10                  15

Thr Leu Ser Leu Thr Cys Thr Val Ser Gly Phe Ser Ile Ser Thr Ser
            20                  25                  30

Gly Tyr Tyr Trp Ser Trp Ile Arg Gln Tyr Pro Gly Lys Arg Leu Glu
        35                  40                  45

Trp Ile Gly Tyr Ile Asn Tyr Gly Gly Thr Ser Tyr Asn Pro Ser
    50                  55                  60

Leu Lys Ser Arg Val Thr Ile Ser Arg Asp Thr Ser Lys Asn Gln Phe
65                  70                  75                  80

Ser Leu Lys Leu Thr Ser Val Thr Ala Ala Asp Thr Ala Thr Tyr Cys
            85                  90                  95

Cys Ala Thr Met Ala Asp Arg Phe Ala Phe Phe Asp Val Trp Gly Gln
            100                 105                 110

Gly Thr Met Val Thr Val Ser Ser
        115                 120
```

<210> SEQ ID NO 28
<211> LENGTH: 120
<212> TYPE: PRT
<213> ORGANISM: Artificial Sequence
<220> FEATURE:
<223> OTHER INFORMATION: Variant of humanized anti-human H7CR Antibody

<400> SEQUENCE: 28

```
Gln Val Gln Leu Gln Glu Ser Gly Pro Gly Leu Val Lys Pro Ala Gln
1               5                   10                  15

Thr Leu Ser Leu Thr Cys Thr Val Ser Gly Phe Ser Ile Ser Thr Ser
            20                  25                  30

Gly Tyr Tyr Trp Ser Trp Ile Arg Gln Phe Pro Gly Lys Arg Leu Glu
```

```
                35                  40                  45
Trp Met Gly Tyr Ile Asn Tyr Gly Gly Gly Thr Ser Tyr Asn Pro Ser
         50                  55                  60

Leu Lys Ser Arg Val Thr Ile Ser Arg Asp Thr Ser Lys Asn Gln Phe
 65                  70                  75                  80

Ser Leu Lys Leu Thr Ser Val Thr Ala Ala Asp Thr Ala Thr Tyr Cys
                 85                  90                  95

Cys Ala Thr Met Ala Asp Arg Phe Ala Phe Phe Asp Val Trp Gly Gln
            100                 105                 110

Gly Thr Met Val Thr Val Ser Ser
        115                 120
```

<210> SEQ ID NO 29
<211> LENGTH: 12
<212> TYPE: PRT
<213> ORGANISM: Artificial Sequence
<220> FEATURE:
<223> OTHER INFORMATION: Anti-Human H7CR Antibody

<400> SEQUENCE: 29

```
Gln Ser Leu Phe Ser Ser Asn Thr Asn Arg Asn Tyr
 1               5                  10
```

<210> SEQ ID NO 30
<211> LENGTH: 12
<212> TYPE: PRT
<213> ORGANISM: Artificial Sequence
<220> FEATURE:
<223> OTHER INFORMATION: Anti-Human H7CR Antibody

<400> SEQUENCE: 30

```
Gln Ser Leu Phe Ser Ser Asn Thr Lys Arg Asn Tyr
 1               5                  10
```

<210> SEQ ID NO 31
<211> LENGTH: 12
<212> TYPE: PRT
<213> ORGANISM: Artificial Sequence
<220> FEATURE:
<223> OTHER INFORMATION: LC CDR1 Consensus sequence
<220> FEATURE:
<221> NAME/KEY: MISC_FEATURE
<222> LOCATION: (9)..(9)
<223> OTHER INFORMATION: Xaa = N or K or a substitution having an equal
      or greater substitution score

<400> SEQUENCE: 31

```
Gln Ser Leu Phe Ser Ser Asn Thr Xaa Arg Asn Tyr
 1               5                  10
```

<210> SEQ ID NO 32
<211> LENGTH: 3
<212> TYPE: PRT
<213> ORGANISM: Artificial Sequence
<220> FEATURE:
<223> OTHER INFORMATION: LC CDR2 Consensus Sequence:

<400> SEQUENCE: 32

```
His Ala Ser
 1
```

<210> SEQ ID NO 33
<211> LENGTH: 113
<212> TYPE: PRT
<213> ORGANISM: Artificial Sequence

```
<220> FEATURE:
<223> OTHER INFORMATION: Variant of humanized anti-human H7CR Antibody

<400> SEQUENCE: 33

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Ser Ser
            20                  25                  30

Asn Thr Lys Arg Asn Tyr Leu Ala Trp Tyr Gln Gln Lys Pro Gly Gln
        35                  40                  45

Pro Pro Lys Leu Leu Ile Tyr His Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Glu Thr Pro Leu Thr Phe Gly Gln Gly Thr Arg Leu Glu Ile
            100                 105                 110

Lys

<210> SEQ ID NO 34
<211> LENGTH: 113
<212> TYPE: PRT
<213> ORGANISM: Artificial Sequence
<220> FEATURE:
<223> OTHER INFORMATION: Variant of humanized anti-human H7CR Antibody

<400> SEQUENCE: 34

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Ser Ser
            20                  25                  30

Asn Thr Lys Arg Asn Tyr Leu Asn Trp Tyr Gln Gln Lys Pro Gly Gln
        35                  40                  45

Pro Pro Lys Leu Leu Ile Tyr His Ala Ser Thr Arg Leu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Asp Tyr Phe Cys Gln Gln
                85                  90                  95

His Tyr Glu Thr Pro Leu Thr Phe Gly Asp Gly Thr Arg Leu Glu Ile
            100                 105                 110

Lys

<210> SEQ ID NO 35
<211> LENGTH: 113
<212> TYPE: PRT
<213> ORGANISM: Artificial Sequence
<220> FEATURE:
<223> OTHER INFORMATION: Variant of humanized anti-human H7CR Antibody

<400> SEQUENCE: 35

Asp Ile Val Met Thr Gln Ser Pro Asp Ser Leu Ala Val Ser Leu Gly
1               5                   10                  15

Glu Arg Ala Thr Ile Asn Cys Leu Ser Ser Gln Ser Leu Phe Ser Ser
            20                  25                  30

Asn Thr Lys Arg Asn Tyr Leu Asn Trp Tyr Gln Gln Lys Pro Gly Gln
        35                  40                  45
```

Ser Pro Lys Leu Leu Ile Tyr His Ala Ser Thr Arg Leu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Asp Tyr Phe Cys Gln Gln
                85                  90                  95

His Tyr Glu Thr Pro Leu Thr Phe Gly Asp Gly Thr Arg Leu Glu Ile
            100                 105                 110

Lys

<210> SEQ ID NO 36
<211> LENGTH: 113
<212> TYPE: PRT
<213> ORGANISM: Artificial Sequence
<220> FEATURE:
<223> OTHER INFORMATION: Variant of humanized anti-human H7CR Antibody

<400> SEQUENCE: 36

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Phe Ser Ser
            20                  25                  30

Asn Thr Lys Arg Asn Tyr Leu Asp Trp Tyr Leu Gln Lys Pro Gly Gln
        35                  40                  45

Ser Pro Gln Leu Leu Ile Tyr His Ala Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

His Tyr Glu Thr Pro Leu Thr Phe Gly Gln Gly Thr Arg Leu Glu Ile
            100                 105                 110

Lys

<210> SEQ ID NO 37
<211> LENGTH: 113
<212> TYPE: PRT
<213> ORGANISM: Artificial Sequence
<220> FEATURE:
<223> OTHER INFORMATION: Variant of humanized anti-human H7CR Antibody

<400> SEQUENCE: 37

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Phe Ser Ser
            20                  25                  30

Asn Thr Lys Arg Asn Tyr Leu Asn Trp Tyr Leu Gln Lys Pro Gly Gln
        35                  40                  45

Ser Pro Lys Leu Leu Ile Tyr His Ala Ser Thr Arg Leu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Asp Tyr Phe Cys Gln Gln
                85                  90                  95

His Tyr Glu Thr Pro Leu Thr Phe Gly Asp Gly Thr Arg Leu Glu Ile
            100                 105                 110

Lys

<210> SEQ ID NO 38
<211> LENGTH: 113
<212> TYPE: PRT
<213> ORGANISM: Artificial Sequence
<220> FEATURE:
<223> OTHER INFORMATION: Variant of humanized anti-human H7CR Antibody

<400> SEQUENCE: 38

Asp Ile Val Met Thr Gln Thr Pro Ser Ser Leu Pro Val Thr Pro Gly
1               5                   10                  15

Glu Pro Ala Ser Ile Ser Cys Leu Ser Ser Gln Ser Leu Phe Ser Ser
            20                  25                  30

Asn Thr Lys Arg Asn Tyr Leu Asn Trp Tyr Leu Gln Lys Pro Gly Gln
        35                  40                  45

Ser Pro Lys Leu Leu Ile Tyr His Ala Ser Thr Arg Leu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Asp Tyr Phe Cys Gln Gln
                85                  90                  95

His Tyr Glu Thr Pro Leu Thr Phe Gly Asp Gly Thr Arg Leu Glu Ile
            100                 105                 110

Lys

<210> SEQ ID NO 39
<211> LENGTH: 120
<212> TYPE: PRT
<213> ORGANISM: Artificial Sequence
<220> FEATURE:
<223> OTHER INFORMATION: Variant of humanized anti-human H7CR Antibody

<400> SEQUENCE: 39

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Thr Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Thr Ser Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Asp Met Ala Asp Lys Gly Gly Trp Phe Ala Tyr Trp Gly Gln
            100                 105                 110

Gly Thr Leu Val Thr Val Ser Ser
        115                 120

<210> SEQ ID NO 40
<211> LENGTH: 120
<212> TYPE: PRT
<213> ORGANISM: Artificial Sequence
<220> FEATURE:
<223> OTHER INFORMATION: Variant of humanized anti-human H7CR Antibody

<400> SEQUENCE: 40

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Thr Gly
            20                  25                  30

Gly Tyr Tyr Trp Asn Trp Ile Arg Gln His Pro Gly Lys Lys Leu Glu
        35                  40                  45

Trp Ile Gly Tyr Ile Tyr Thr Ser Gly Arg Thr Ser Tyr Asn Pro Ser
50                  55                  60

Leu Lys Ser Arg Val Thr Ile Ser Arg Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Asp Met Ala Asp Lys Gly Gly Trp Phe Ala Tyr Trp Gly Gln
            100                 105                 110

Gly Thr Leu Val Thr Val Ser Ser
            115                 120

<210> SEQ ID NO 41
<211> LENGTH: 120
<212> TYPE: PRT
<213> ORGANISM: Artificial Sequence
<220> FEATURE:
<223> OTHER INFORMATION: Variant of humanized anti-human H7CR Antibody

<400> SEQUENCE: 41

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Thr Gly
            20                  25                  30

Gly Tyr Tyr Trp Asn Trp Ile Arg Gln Phe Pro Gly Lys Lys Leu Glu
        35                  40                  45

Trp Met Gly Tyr Ile Tyr Thr Ser Gly Arg Thr Ser Tyr Asn Pro Ser
50                  55                  60

Leu Lys Ser Arg Val Thr Ile Ser Arg Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Asp Met Ala Asp Lys Gly Gly Trp Phe Ala Tyr Trp Gly Gln
            100                 105                 110

Gly Thr Leu Val Thr Val Ser Ser
            115                 120

<210> SEQ ID NO 42
<211> LENGTH: 120
<212> TYPE: PRT
<213> ORGANISM: Artificial Sequence
<220> FEATURE:
<223> OTHER INFORMATION: Variant of humanized anti-human H7CR Antibody

<400> SEQUENCE: 42

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Ile Thr Thr Gly
            20                  25                  30

Gly Tyr Tyr Val Gly Trp Ile Arg Gln Pro Pro Gly Lys Ala Leu Glu
        35                  40                  45

Trp Leu Ala Leu Ile Tyr Thr Ser Gly Arg Thr Arg Tyr Ser Pro Ser
50                  55                  60
```

```
Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
             85                  90                  95

Cys Ala Asp Met Ala Asp Lys Gly Gly Trp Phe Ala Tyr Trp Gly Gln
            100                 105                 110

Gly Thr Leu Val Thr Val Ser Ser
        115                 120

<210> SEQ ID NO 43
<211> LENGTH: 120
<212> TYPE: PRT
<213> ORGANISM: Artificial Sequence
<220> FEATURE:
<223> OTHER INFORMATION: Variant of humanized anti-human H7CR Antibody

<400> SEQUENCE: 43

Gln Ile Thr Leu Lys Glu Ser Gly Pro Thr Leu Val Lys Pro Thr Gln
 1               5                  10                  15

Thr Leu Thr Leu Thr Cys Thr Val Ser Gly Phe Ser Ile Thr Thr Gly
             20                  25                  30

Gly Tyr Tyr Trp Asn Trp Ile Arg Gln Pro Pro Gly Lys Lys Leu Glu
             35                 40                  45

Trp Leu Ala Leu Ile Tyr Thr Ser Gly Arg Thr Ser Tyr Asn Pro Ser
    50                  55                  60

Leu Lys Ser Arg Leu Thr Ile Thr Lys Asp Thr Ser Lys Asn Gln Val
 65                 70                  75                  80

Val Leu Thr Met Thr Asn Met Asp Pro Val Asp Thr Ala Thr Tyr Tyr
             85                  90                  95

Cys Ala Asp Met Ala Asp Lys Gly Gly Trp Phe Ala Tyr Trp Gly Gln
            100                 105                 110

Gly Thr Leu Val Thr Val Ser Ser
        115                 120

<210> SEQ ID NO 44
<211> LENGTH: 120
<212> TYPE: PRT
<213> ORGANISM: Artificial Sequence
<220> FEATURE:
<223> OTHER INFORMATION: Variant of humanized anti-human H7CR Antibody

<400> SEQUENCE: 44

Gln Ile Gln Leu Lys Glu Ser Gly Pro Thr Leu Val Lys Pro Thr Gln
 1               5                  10                  15

Thr Leu Thr Leu Thr Cys Thr Val Ser Gly Phe Ser Ile Thr Thr Gly
             20                  25                  30

Gly Tyr Tyr Trp Asn Trp Ile Arg Gln Pro Pro Gly Lys Lys Leu Glu
             35                 40                  45

Trp Met Ala Leu Ile Tyr Thr Ser Gly Arg Thr Ser Tyr Asn Pro Ser
    50                  55                  60

Leu Lys Ser Arg Leu Thr Ile Thr Lys Asp Thr Ser Lys Asn Gln Val
 65                 70                  75                  80

Val Leu Thr Met Thr Asn Met Asp Pro Val Asp Thr Ala Thr Tyr Tyr
             85                  90                  95

Cys Ala Asp Met Ala Asp Lys Gly Gly Trp Phe Ala Tyr Trp Gly Gln
            100                 105                 110

Gly Thr Leu Val Thr Val Ser Ser
```

```
<210> SEQ ID NO 45
<211> LENGTH: 9
<212> TYPE: PRT
<213> ORGANISM: Artificial Sequence
<220> FEATURE:
<223> OTHER INFORMATION: Anti-Human H7CR Antibody

<400> SEQUENCE: 45

Gln His His Tyr Glu Thr Pro Leu Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Anti-Human H7CR Antibody

<400> SEQUENCE: 46

Gln Gln His Tyr Glu Thr Pro Leu Thr
1               5

<210> SEQ ID NO 47
<211> LENGTH: 9
<212> TYPE: PRT
<213> ORGANISM: Artificial Sequence
<220> FEATURE:
<223> OTHER INFORMATION: Anti-Human H7CR Antibody

<400> SEQUENCE: 47

Gln Gln His Tyr Val Thr Pro Leu Thr
1               5

<210> SEQ ID NO 48
<211> LENGTH: 9
<212> TYPE: PRT
<213> ORGANISM: Artificial Sequence
<220> FEATURE:
<223> OTHER INFORMATION: LC CDR3 Consensus Sequence
<220> FEATURE:
<221> NAME/KEY: MISC_FEATURE
<222> LOCATION: (2)..(2)
<223> OTHER INFORMATION: Xaa is H or Q or a substitution having an equal
      or greater substitution score (i.e., greater than or equal 0): R,
      N, Q, E, or H
<220> FEATURE:
<221> NAME/KEY: MISC_FEATURE
<222> LOCATION: (5)..(5)
<223> OTHER INFORMATION: Xaa is E or V or a substitution having an equal
      or greater substitution score (i.e., greater than or equal to -2):
      A, Q, E, K, M, P, S, T, Y, or V

<400> SEQUENCE: 48

Gln Xaa His Tyr Xaa Thr Pro Leu Thr
1               5

<210> SEQ ID NO 49
<211> LENGTH: 8
<212> TYPE: PRT
<213> ORGANISM: Artificial Sequence
<220> FEATURE:
<223> OTHER INFORMATION: Anti-Human H7CR Antibody

<400> SEQUENCE: 49

Gly Phe Ser Ile Ser Thr Ser Gly
1               5
```

<210> SEQ ID NO 50
<211> LENGTH: 8
<212> TYPE: PRT
<213> ORGANISM: Artificial Sequence
<220> FEATURE:
<223> OTHER INFORMATION: Anti-Human H7CR Antibody

<400> SEQUENCE: 50

Gly Phe Ser Ile Thr Thr Gly Gly
1               5

<210> SEQ ID NO 51
<211> LENGTH: 8
<212> TYPE: PRT
<213> ORGANISM: Artificial Sequence
<220> FEATURE:
<223> OTHER INFORMATION: Heavy chain CDR1 consensus sequence
<220> FEATURE:
<221> NAME/KEY: MISC_FEATURE
<222> LOCATION: (5)..(5)
<223> OTHER INFORMATION: Xaa is S or T or a substitution having an equal
      or greater substitution score (i.e., greater than/equal to +1): S
      or T
<220> FEATURE:
<221> NAME/KEY: MISC_FEATURE
<222> LOCATION: (7)..(7)
<223> OTHER INFORMATION: Xaa is S or G or a substitution having an equal
      or greater substitution score (i.e., greater than/equal to 0): A,
      N, G, or S

<400> SEQUENCE: 51

Gly Phe Asp Ile Xaa Thr Xaa Gly
1               5

<210> SEQ ID NO 52
<211> LENGTH: 7
<212> TYPE: PRT
<213> ORGANISM: Artificial Sequence
<220> FEATURE:
<223> OTHER INFORMATION: Anti-Human H7CR Antibody

<400> SEQUENCE: 52

Ile Asn Tyr Gly Gly Gly Thr
1               5

<210> SEQ ID NO 53
<211> LENGTH: 7
<212> TYPE: PRT
<213> ORGANISM: Artificial Sequence
<220> FEATURE:
<223> OTHER INFORMATION: Anti-Human H7CR Antibody

<400> SEQUENCE: 53

Ile Tyr Thr Ser Gly Arg Thr
1               5

<210> SEQ ID NO 54
<211> LENGTH: 7
<212> TYPE: PRT
<213> ORGANISM: Artificial Sequence
<220> FEATURE:
<223> OTHER INFORMATION: Anti-Human H7CR Antibody

<400> SEQUENCE: 54

Ile Tyr Ser Ser Gly Arg Thr
1               5

<210> SEQ ID NO 55

```
<211> LENGTH: 7
<212> TYPE: PRT
<213> ORGANISM: Artificial Sequence
<220> FEATURE:
<223> OTHER INFORMATION: Heavy chain CDR2 Consensus Sequence
<220> FEATURE:
<221> NAME/KEY: MISC_FEATURE
<222> LOCATION: (2)..(2)
<223> OTHER INFORMATION: Xaa is N or Y or a substitution having an equal
      or greater substitution score (i.e., greater than/equal to -2): A,
      R, N, Q, E, H, K, M, S, T, Y
<220> FEATURE:
<221> NAME/KEY: MISC_FEATURE
<222> LOCATION: (3)..(3)
<223> OTHER INFORMATION: Xaa is Y, T or S or a substitution having an
      equal or greater substitution score (i.e., greater than/equal to
      -2): A, R, N, C, Q, E, H, I, L, K, M, F, S, T, Y, or V
<220> FEATURE:
<221> NAME/KEY: MISC_FEATURE
<222> LOCATION: (4)..(4)
<223> OTHER INFORMATION: Xaa is S or G or a substitution having an equal
      or greater substitution score (i.e., greater than/equal to 0): A,
      N, G, or S
<220> FEATURE:
<221> NAME/KEY: MISC_FEATURE
<222> LOCATION: (6)..(6)
<223> OTHER INFORMATION: Xaa is G or R or a substitution having an
      equal or greater substitution score (i.e., greater than/equal to
      -2): A, R, N, D, Q, E, G, H, K, P, S, or T

<400> SEQUENCE: 55

Ile Xaa Xaa Xaa Gly Xaa Thr
1               5

<210> SEQ ID NO 56
<211> LENGTH: 12
<212> TYPE: PRT
<213> ORGANISM: Artificial Sequence
<220> FEATURE:
<223> OTHER INFORMATION: Anti-Human H7CR Antibody

<400> SEQUENCE: 56

Ala Thr Met Ala Asp Arg Phe Ala Phe Phe Asp Val
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Anti-Human H7CR Antibody

<400> SEQUENCE: 57

Ala Asp Met Ala Asp Lys Gly Gly Trp Phe Ala Tyr
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Anti-Human H7CR Antibody

<400> SEQUENCE: 58

Ala Asp Met Ala Asp Lys Gly Gly Trp Phe Asp Tyr
1               5                   10

<210> SEQ ID NO 59
<211> LENGTH: 12
<212> TYPE: PRT
<213> ORGANISM: Artificial Sequence
```

```
<220> FEATURE:
<223> OTHER INFORMATION: Heavy chain CDR3 Consensus Sequence:
<220> FEATURE:
<221> NAME/KEY: MISC_FEATURE
<222> LOCATION: (2)..(2)
<223> OTHER INFORMATION: Xaa is T or D or a substitution having an equal
      or greater substitution score (i.e., greater than/equal to -1): N,
      D, Q, E, K, P, S, or T
<220> FEATURE:
<221> NAME/KEY: MISC_FEATURE
<222> LOCATION: (6)..(6)
<223> OTHER INFORMATION: Xaa is R or K or a substitution having an equal
      or greater substitution score  (i.e., greater than/equal to +2):
      R, or K
<220> FEATURE:
<221> NAME/KEY: MISC_FEATURE
<222> LOCATION: (7)..(7)
<223> OTHER INFORMATION: Xaa is F or G or a substitution having an equal
      or greater substitution score (i.e., greater than/equal to -3): A,
      R, N, D, C, Q, E, G, H, K, M, F, S, T, W, Y, or V
<220> FEATURE:
<221> NAME/KEY: MISC_FEATURE
<222> LOCATION: (8)..(8)
<223> OTHER INFORMATION: Xaa is A or G or a substitution having an equal
      or greater substitution score (i.e., greater than/equal to 0): A,
      G, or S
<220> FEATURE:
<221> NAME/KEY: MISC_FEATURE
<222> LOCATION: (9)..(9)
<223> OTHER INFORMATION: Xaa is F or W or a substitution having an equal
      or greater substitution score (i.e., greater than/equal to +1): F,
      W, or Y
<220> FEATURE:
<221> NAME/KEY: MISC_FEATURE
<222> LOCATION: (11)..(11)
<223> OTHER INFORMATION: Xaa is A or D or a substitution having an equal
      or greater substitution score (i.e., greater than/equal to ): A,
      R, N, D, C, Q, E, G, H, I, L, K, M, F, P, S, T, W, Y, or V
<220> FEATURE:
<221> NAME/KEY: MISC_FEATURE
<222> LOCATION: (11)..(11)
<223> OTHER INFORMATION: Xaa is A or D or a substitution having an equal
      or greater substitution score: A, R, N, D, C, Q, E, G, H, I, L, K,
      M, F, P, S, T, W, Y, or V
<220> FEATURE:
<221> NAME/KEY: MISC_FEATURE
<222> LOCATION: (12)..(12)
<223> OTHER INFORMATION: Xaa is V or Y or a substitution having an equal
      or greater substitution score (i.e., greater than/equal to -2): A,
      R, N, D, C, Q, E, G, H, I, L, K, M, F, P, S, T, W, Y, or V

<400> SEQUENCE: 59

Ala Xaa Met Ala Asp Xaa Xaa Xaa Xaa Phe Xaa Xaa
1               5                   10

<210> SEQ ID NO 60
<211> LENGTH: 40
<212> TYPE: PRT
<213> ORGANISM: Artificial Sequence
<220> FEATURE:
<223> OTHER INFORMATION: Humanized Antibody

<400> SEQUENCE: 60

Asp Ile Val Met Thr Gln Ser Pro Ser Ser Leu Ala Val Ser Ala Gly
1               5                   10                  15

Glu Lys Val Thr Ile Ser Cys Leu Ser Ser Gln Ser Leu Phe Ser Ser
            20                  25                  30

Asn Thr Asn Arg Asn Tyr Leu Asn
            35                  40

<210> SEQ ID NO 61
<211> LENGTH: 40
<212> TYPE: PRT
```

<213> ORGANISM: Artificial Sequence
<220> FEATURE:
<223> OTHER INFORMATION: Variant of humanized anti-human H7CR Antibody

<400> SEQUENCE: 61

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala
        35                  40

<210> SEQ ID NO 62
<211> LENGTH: 39
<212> TYPE: PRT
<213> ORGANISM: Artificial Sequence
<220> FEATURE:
<223> OTHER INFORMATION: Variant of humanized anti-human H7CR Antibody

<400> SEQUENCE: 62

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp
        35

<210> SEQ ID NO 63
<211> LENGTH: 40
<212> TYPE: PRT
<213> ORGANISM: Artificial Sequence
<220> FEATURE:
<223> OTHER INFORMATION: Humanized antibody

<400> SEQUENCE: 63

Trp Tyr Leu Gln Lys Pro Gly Gln Ser Pro Lys Leu Leu Ile Tyr His
1               5                   10                  15

Ala Ser Thr Arg Leu Thr Gly Val Pro Asp Arg Phe Ile Gly Ser Gly
            20                  25                  30

Ser Gly Thr Asp Phe Thr Leu Thr
        35                  40

<210> SEQ ID NO 64
<211> LENGTH: 40
<212> TYPE: PRT
<213> ORGANISM: Artificial Sequence
<220> FEATURE:
<223> OTHER INFORMATION: Variant of humanized anti-human H7CR Antibody

<400> SEQUENCE: 64

Trp Tyr Gln Gln Lys Pro Gly Gln Pro Pro Lys Leu Leu Ile Tyr Trp
1               5                   10                  15

Ala Ser Thr Arg Glu Ser Gly Val Pro Asp Arg Phe Ser Gly Ser Gly
            20                  25                  30

Ser Gly Thr Asp Phe Thr Leu Thr
        35                  40

<210> SEQ ID NO 65
<211> LENGTH: 40
<212> TYPE: PRT
<213> ORGANISM: Artificial Sequence
<220> FEATURE:
<223> OTHER INFORMATION: Variant of humanized anti-human H7CR Antibody

```
<400> SEQUENCE: 65

Trp Tyr Leu Gln Lys Pro Gly Gln Ser Pro Gln Leu Leu Ile Tyr Leu
1               5                   10                  15

Gly Ser Asn Arg Ala Ser Gly Val Pro Asp Arg Phe Ser Gly Ser Gly
            20                  25                  30

Ser Gly Thr Asp Phe Thr Leu Lys
        35                  40

<210> SEQ ID NO 66
<211> LENGTH: 33
<212> TYPE: PRT
<213> ORGANISM: Artificial Sequence
<220> FEATURE:
<223> OTHER INFORMATION: Variant of humanized anti-human H7CR Antibody

<400> SEQUENCE: 66

Ile Ser Ser Val Gln Ala Glu Asp Leu Gly Asp Tyr Tyr Cys Gln His
1               5                   10                  15

His Tyr Glu Thr Pro Leu Thr Phe Gly Asp Gly Thr Lys Leu Glu Ile
            20                  25                  30

Lys

<210> SEQ ID NO 67
<211> LENGTH: 23
<212> TYPE: PRT
<213> ORGANISM: Artificial Sequence
<220> FEATURE:
<223> OTHER INFORMATION: Variant of humanized anti-human H7CR Antibody

<400> SEQUENCE: 67

Ile Ser Ser Leu Gln Ala Glu Asp Val Ala Val Tyr Tyr Cys Gln Gln
1               5                   10                  15

Tyr Tyr Ser Thr Pro Tyr Thr
            20

<210> SEQ ID NO 68
<211> LENGTH: 23
<212> TYPE: PRT
<213> ORGANISM: Artificial Sequence
<220> FEATURE:
<223> OTHER INFORMATION: Variant of humanized anti-human H7CR Antibody

<400> SEQUENCE: 68

Ile Ser Arg Val Glu Ala Glu Asp Val Gly Val Tyr Tyr Cys Met Gln
1               5                   10                  15

Ala Leu Gln Thr Pro Tyr Thr
            20

<210> SEQ ID NO 69
<211> LENGTH: 10
<212> TYPE: PRT
<213> ORGANISM: Artificial Sequence
<220> FEATURE:
<223> OTHER INFORMATION: Humanized antibody

<400> SEQUENCE: 69

Phe Gly Gln Gly Thr Lys Leu Glu Ile Lys
1               5                   10

<210> SEQ ID NO 70
<211> LENGTH: 40
<212> TYPE: PRT
```

<213> ORGANISM: Artificial Sequence
<220> FEATURE:
<223> OTHER INFORMATION: Humanized antibody

<400> SEQUENCE: 70

Gln Ile Gln Leu Gln Glu Ser Gly Pro Gly Leu Val Lys Pro Ser Gln
1               5                   10                  15

Ser Leu Ser Leu Thr Cys Ser Val Thr Gly Phe Ser Ile Ser Thr Ser
            20                  25                  30

Gly Tyr Tyr Trp Thr Trp Ile Arg
        35                  40

<210> SEQ ID NO 71
<211> LENGTH: 40
<212> TYPE: PRT
<213> ORGANISM: Artificial Sequence
<220> FEATURE:
<223> OTHER INFORMATION: Variant of humanized anti-human H7CR Antibody

<400> SEQUENCE: 71

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg
        35                  40

<210> SEQ ID NO 72
<211> LENGTH: 40
<212> TYPE: PRT
<213> ORGANISM: Homo sapiens

<400> SEQUENCE: 72

Gln Val Gln Leu Gln Glu Ser Gly Pro Gly Leu Val Lys Pro Ala Gln
1               5                   10                  15

Thr Leu Ser Leu Thr Cys Thr Val Ser Gly Gly Ser Ile Ser Ser Val
            20                  25                  30

Asn Tyr Tyr Trp Ser Trp Ile Arg
        35                  40

<210> SEQ ID NO 73
<211> LENGTH: 40
<212> TYPE: PRT
<213> ORGANISM: Artificial Sequence
<220> FEATURE:
<223> OTHER INFORMATION: Variant of humanized anti-human H7CR Antibody

<400> SEQUENCE: 73

Gln Phe Pro Gly Lys Arg Leu Glu Trp Met Gly Tyr Ile Asn Tyr Gly
1               5                   10                  15

Gly Gly Thr Ser Tyr Asn Pro Ser Leu Lys Ser Arg Ile Ser Ile Thr
            20                  25                  30

Arg Asp Thr Ser Lys Asn Gln Phe
        35                  40

<210> SEQ ID NO 74
<211> LENGTH: 40
<212> TYPE: PRT
<213> ORGANISM: Artificial Sequence
<220> FEATURE:
<223> OTHER INFORMATION: Variant of humanized anti-human H7CR Antibody

<400> SEQUENCE: 74

Gln His Pro Gly Lys Gly Leu Glu Trp Ile Gly Tyr Ile Tyr Tyr Ser
1               5                   10                  15

Gly Ser Thr Tyr Tyr Asn Pro Ser Leu Lys Ser Arg Val Thr Ile Ser
            20                  25                  30

Val Asp Thr Ser Lys Asn Gln Phe
        35                  40

<210> SEQ ID NO 75
<211> LENGTH: 40
<212> TYPE: PRT
<213> ORGANISM: Homo sapiens

<400> SEQUENCE: 75

Gln Tyr Pro Gly Lys Gly Leu Glu Trp Ile Gly Tyr Ile Tyr Tyr Arg
1               5                   10                  15

Gly Ser Thr Tyr Tyr Asn Pro Ser Leu Lys Ser Arg Val Thr Ile Ser
            20                  25                  30

Val Asp Thr Ser Lys Asn Gln Phe
        35                  40

<210> SEQ ID NO 76
<211> LENGTH: 40
<212> TYPE: PRT
<213> ORGANISM: Artificial Sequence
<220> FEATURE:
<223> OTHER INFORMATION: Humanized antibody

<400> SEQUENCE: 76

Leu Leu His Leu Asn Ser Val Thr Thr Glu Asp Thr Ala Thr Tyr Cys
1               5                   10                  15

Cys Ala Thr Met Ala Asp Arg Phe Ala Phe Phe Asp Val Trp Gly Gln
            20                  25                  30

Gly Ile Gln Val Thr Val Ser Ser
        35                  40

<210> SEQ ID NO 77
<211> LENGTH: 19
<212> TYPE: PRT
<213> ORGANISM: Artificial Sequence
<220> FEATURE:
<223> OTHER INFORMATION: Variant of humanized anti-human H7CR Antibody

<400> SEQUENCE: 77

Ser Leu Lys Leu Ser Ser Val Thr Ala Ala Asp Thr Ala Val Tyr Tyr
1               5                   10                  15

Cys Ala Arg

<210> SEQ ID NO 78
<211> LENGTH: 40
<212> TYPE: PRT
<213> ORGANISM: Homo sapiens

<400> SEQUENCE: 78

Ser Leu Lys Leu Thr Ser Val Thr Ala Ala Asp Thr Ala Val Tyr His
1               5                   10                  15

Cys Ala Arg Glu Arg Thr Met Thr Gly Ala Phe Asp Ile Trp Gly Gln
            20                  25                  30

Gly Thr Met Val Thr Val Ser Ser
        35                  40

```
<210> SEQ ID NO 79
<211> LENGTH: 16
<212> TYPE: PRT
<213> ORGANISM: Artificial Sequence
<220> FEATURE:
<223> OTHER INFORMATION: Humanized antibody

<400> SEQUENCE: 79

Asp Ala Phe Asp Val Trp Gly Gln Gly Thr Met Val Thr Val Ser Ser
1               5                   10                  15

<210> SEQ ID NO 80
<211> LENGTH: 40
<212> TYPE: PRT
<213> ORGANISM: Artificial Sequence
<220> FEATURE:
<223> OTHER INFORMATION: Humanized antibody

<400> SEQUENCE: 80

Asp Ile Val Met Thr Gln Ser Pro Ser Ser Leu Ala Val Ser Ala Gly
1               5                   10                  15

Glu Lys Val Thr Ile Ser Cys Leu Ser Ser Gln Ser Leu Phe Ser Ser
            20                  25                  30

Asn Thr Lys Arg Asn Tyr Leu Asn
        35                  40

<210> SEQ ID NO 81
<211> LENGTH: 40
<212> TYPE: PRT
<213> ORGANISM: Artificial Sequence
<220> FEATURE:
<223> OTHER INFORMATION: Variant of humanized anti-human H7CR Antibody

<400> SEQUENCE: 81

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala
        35                  40

<210> SEQ ID NO 82
<211> LENGTH: 40
<212> TYPE: PRT
<213> ORGANISM: Artificial Sequence
<220> FEATURE:
<223> OTHER INFORMATION: Variant of humanized anti-human H7CR Antibody

<400> SEQUENCE: 82

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp
        35                  40

<210> SEQ ID NO 83
<211> LENGTH: 40
<212> TYPE: PRT
<213> ORGANISM: Artificial Sequence
<220> FEATURE:
<223> OTHER INFORMATION: Humanized antibody

<400> SEQUENCE: 83
```

```
Trp Tyr Leu Gln Lys Pro Gly Gln Ser Pro Lys Leu Leu Ile Tyr His
1               5                  10                  15

Ala Ser Thr Arg Leu Thr Gly Val Pro Gly Arg Phe Ile Gly Ser Gly
                20                  25                  30

Ser Gly Thr Asp Phe Thr Leu Thr
        35                  40
```

<210> SEQ ID NO 84
<211> LENGTH: 40
<212> TYPE: PRT
<213> ORGANISM: Artificial Sequence
<220> FEATURE:
<223> OTHER INFORMATION: Variant of humanized anti-human H7CR Antibody

<400> SEQUENCE: 84

```
Trp Tyr Gln Gln Lys Pro Gly Gln Pro Pro Lys Leu Leu Ile Tyr Trp
1               5                  10                  15

Ala Ser Thr Arg Glu Ser Gly Val Pro Asp Arg Phe Ser Gly Ser Gly
                20                  25                  30

Ser Gly Thr Asp Phe Thr Leu Thr
        35                  40
```

<210> SEQ ID NO 85
<211> LENGTH: 40
<212> TYPE: PRT
<213> ORGANISM: Artificial Sequence
<220> FEATURE:
<223> OTHER INFORMATION: Variant of humanized anti-human H7CR Antibody

<400> SEQUENCE: 85

```
Trp Tyr Leu Gln Lys Pro Gly Gln Ser Pro Gln Leu Leu Ile Tyr Thr
1               5                  10                  15

Leu Ser Tyr Arg Ala Ser Gly Val Pro Asp Arg Phe Ser Gly Ser Gly
                20                  25                  30

Ser Gly Thr Asp Phe Thr Leu Lys
        35                  40
```

<210> SEQ ID NO 86
<211> LENGTH: 33
<212> TYPE: PRT
<213> ORGANISM: Artificial Sequence
<220> FEATURE:
<223> OTHER INFORMATION: Humanized antibody

<400> SEQUENCE: 86

```
Val Ser Thr Val Gln Ala Glu Asp Leu Gly Asp Tyr Phe Cys Gln Gln
1               5                  10                  15

His Tyr Glu Thr Pro Leu Thr Phe Gly Asp Gly Thr Arg Leu Glu Ile
                20                  25                  30

Lys
```

<210> SEQ ID NO 87
<211> LENGTH: 23
<212> TYPE: PRT
<213> ORGANISM: Artificial Sequence
<220> FEATURE:
<223> OTHER INFORMATION: Variant of humanized anti-human H7CR Antibody

<400> SEQUENCE: 87

```
Ile Ser Ser Leu Gln Ala Glu Asp Val Ala Val Tyr Tyr Cys Gln Gln
1               5                  10                  15

Tyr Tyr Ser Thr Pro Tyr Thr
```

20

<210> SEQ ID NO 88
<211> LENGTH: 21
<212> TYPE: PRT
<213> ORGANISM: Artificial Sequence
<220> FEATURE:
<223> OTHER INFORMATION: Variant of humanized anti-human H7CR Antibody

<400> SEQUENCE: 88

Ile Ser Arg Val Glu Ala Glu Asp Val Gly Val Tyr Tyr Cys Met Gln
1               5                   10                  15

Arg Ile Glu Phe Pro
            20

<210> SEQ ID NO 89
<211> LENGTH: 12
<212> TYPE: PRT
<213> ORGANISM: Artificial Sequence
<220> FEATURE:
<223> OTHER INFORMATION: Humanized antibody

<400> SEQUENCE: 89

Ile Thr Phe Gly Gln Gly Thr Arg Leu Glu Ile Lys
1               5                   10

<210> SEQ ID NO 90
<211> LENGTH: 40
<212> TYPE: PRT
<213> ORGANISM: Artificial Sequence
<220> FEATURE:
<223> OTHER INFORMATION: Humanized antibody

<400> SEQUENCE: 90

Gln Ile Gln Leu Gln Glu Ser Gly Pro Gly Leu Val Lys Pro Ser Gln
1               5                   10                  15

Ser Leu Ser Leu Thr Cys Ser Val Thr Gly Phe Ser Ile Thr Thr Gly
            20                  25                  30

Gly Tyr Tyr Trp Asn Trp Ile Arg
        35                  40

<210> SEQ ID NO 91
<211> LENGTH: 40
<212> TYPE: PRT
<213> ORGANISM: Artificial Sequence
<220> FEATURE:
<223> OTHER INFORMATION: Variant of humanized anti-human H7CR Antibody

<400> SEQUENCE: 91

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg
        35                  40

<210> SEQ ID NO 92
<211> LENGTH: 40
<212> TYPE: PRT
<213> ORGANISM: Artificial Sequence
<220> FEATURE:
<223> OTHER INFORMATION: Variant of humanized anti-human H7CR Antibody

<400> SEQUENCE: 92

-continued

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Val Gly Val Gly Trp Ile Arg
        35                  40

<210> SEQ ID NO 93
<211> LENGTH: 40
<212> TYPE: PRT
<213> ORGANISM: Artificial Sequence
<220> FEATURE:
<223> OTHER INFORMATION: Humanized antibody

<400> SEQUENCE: 93

Gln Phe Pro Gly Lys Lys Leu Glu Trp Met Gly Tyr Ile Tyr Thr Ser
1               5                   10                  15

Gly Arg Thr Ser Tyr Asn Pro Ser Leu Lys Ser Arg Ile Ser Ile Thr
                20                  25                  30

Arg Asp Thr Ser Lys Asn Gln Phe
        35                  40

<210> SEQ ID NO 94
<211> LENGTH: 40
<212> TYPE: PRT
<213> ORGANISM: Artificial Sequence
<220> FEATURE:
<223> OTHER INFORMATION: Variant of humanized anti-human H7CR Antibody

<400> SEQUENCE: 94

Gln His Pro Gly Lys Gly Leu Glu Trp Ile Gly Tyr Ile Tyr Tyr Ser
1               5                   10                  15

Gly Ser Thr Tyr Tyr Asn Pro Ser Leu Lys Ser Arg Val Thr Ile Ser
                20                  25                  30

Val Asp Thr Ser Lys Asn Gln Phe
        35                  40

<210> SEQ ID NO 95
<211> LENGTH: 40
<212> TYPE: PRT
<213> ORGANISM: Artificial Sequence
<220> FEATURE:
<223> OTHER INFORMATION: Variant of humanized anti-human H7CR Antibody

<400> SEQUENCE: 95

Gln Pro Pro Gly Lys Ala Leu Glu Trp Leu Ala Leu Ile Tyr Trp Asn
1               5                   10                  15

Asp Asp Lys Arg Tyr Ser Pro Ser Leu Lys Ser Arg Leu Thr Ile Thr
                20                  25                  30

Lys Asp Thr Ser Lys Asn Gln Val
        35                  40

<210> SEQ ID NO 96
<211> LENGTH: 40
<212> TYPE: PRT
<213> ORGANISM: Artificial Sequence
<220> FEATURE:
<223> OTHER INFORMATION: Humanized antibody

<400> SEQUENCE: 96

Phe Leu Gln Leu Asn Ser Met Thr Thr Glu Asp Thr Ala Thr Tyr Tyr
1               5                   10                  15

Cys Ala Asp Met Ala Asp Lys Gly Gly Trp Phe Ala Tyr Trp Gly Gln
            20                  25                  30

Gly Thr Leu Val Thr Val Ser Ser
        35                  40

<210> SEQ ID NO 97
<211> LENGTH: 23
<212> TYPE: PRT
<213> ORGANISM: Artificial Sequence
<220> FEATURE:
<223> OTHER INFORMATION: Variant of humanized anti-human H7CR Antibody
<220> FEATURE:
<221> NAME/KEY: UNSURE
<222> LOCATION: (19)..(22)

<400> SEQUENCE: 97

Ser Leu Lys Leu Ser Ser Val Thr Ala Ala Asp Thr Ala Val Tyr Tyr
1               5                   10                  15

Cys Ala Xaa Xaa Xaa Xaa Arg
            20

<210> SEQ ID NO 98
<211> LENGTH: 24
<212> TYPE: PRT
<213> ORGANISM: Artificial Sequence
<220> FEATURE:
<223> OTHER INFORMATION: Variant of humanized anti-human H7CR Antibody
<220> FEATURE:
<221> NAME/KEY: UNSURE
<222> LOCATION: (19)..(22)

<400> SEQUENCE: 98

Val Leu Thr Met Thr Asn Met Asp Pro Val Asp Thr Ala Thr Tyr Tyr
1               5                   10                  15

Cys Ala Xaa Xaa Xaa Xaa His Arg
            20

<210> SEQ ID NO 99
<211> LENGTH: 16
<212> TYPE: PRT
<213> ORGANISM: Artificial Sequence
<220> FEATURE:
<223> OTHER INFORMATION: Humanized antibody

<400> SEQUENCE: 99

Asn Trp Phe Asp Ser Trp Gly Gln Gly Thr Leu Val Thr Val Ser Ser
1               5                   10                  15

<210> SEQ ID NO 100
<211> LENGTH: 1401
<212> TYPE: DNA
<213> ORGANISM: Artificial Sequence
<220> FEATURE:
<223> OTHER INFORMATION: Chimeric antibody chain coding sequence

<400> SEQUENCE: 100
atggaatggt cctgggtgtt cctgttcttc ctgtccgtga ccaccggcgt gcactcccag      60
atccagctgc aggaatctgg ccctggcctc gtgaagcctt cccagtccct gtccctgacc     120
tgcagcgtga ccggcttctc catctccacc tccggctact actggacctg gatccggcag     180
ttccctggca gcggctggat ggatgggc tacatcaact acggcggagg cacctcctac      240
aaccccagcc tgaagtcccg gatctccatc acccgggata cctccaagaa ccagttcctg     300
ctgcacctga actccgtgac aaccgaggac accgccacct actgctgcgc taccatggcc     360

```
gacagattcg ccttcttcga cgtgtgggc cagggcatcc aagtgaccgt gtcctccgct      420
tccaccaagg gcccctctgt gtttcctctg gcccttgct cccggtccac ctctgagtct      480
acagccgctc tgggctgcct cgtgaaagac tacttcccg agcccgtgac agtgtcctgg      540
aactctggcg ctctgacctc tggcgtgcac accttcctg ctgtgctgca gtctagcggc      600
ctgtactccc tgtcctccgt cgtgaccgtg ccttccagct ctctgggcac caagacctac      660
acctgtaacg tggaccacaa gccctccaac accaaggtgg acaagagagt ggaatctaag      720
tacggccctc cctgccccc ttgtcctgcc cctgaatttc tgggcggacc ctccgtgttt      780
ctgttccccc caaagcccaa ggacaccctg atgatctccc ggacccccga agtgacctgc      840
gtggtggtgg atgtgtccca ggaagatccc gaggtgcagt tcaattggta cgtggacggc      900
gtggaagtgc acaacgccaa gaccaagcct agagaggaac agttcaactc cacctaccgg      960
gtggtgtccg tgctgaccgt gctgcaccag gattggctga acggcaaaga gtacaagtgc     1020
aaggtgtcca acaagggcct gcctccagc atcgaaaaga ccatctccaa ggctaagggc     1080
cagccccgcg agcccaggt gtacacactg cctccaagcc aggaagagat gaccaagaat     1140
caggtgtcac tgacctgtct cgtgaagggc ttctaccct ccgatatcgc cgtggaatgg     1200
gagtccaacg gccagcccga gaacaactac aagaccaccc cccctgtgct ggactccgac     1260
ggctccttct ttctgtactc tcgcctgacc gtggacaagt cccggtggca ggaaggcaac     1320
gtgttctcct gctctgtgat gcacgaggcc ctgcacaacc actacaccca gaagtccctg     1380
agcctgtccc ccggctgatg a                                               1401

<210> SEQ ID NO 101
<211> LENGTH: 726
<212> TYPE: DNA
<213> ORGANISM: Artificial Sequence
<220> FEATURE:
<223> OTHER INFORMATION: Chimeric antibody chain coding sequence

<400> SEQUENCE: 101
atgtccgtgc ccacccaggt gctgggattg ctgctgctgt ggctgaccga cgccagatgc       60
gacatcgtga tgacccagtc cccctcctcc tggctgtgt ctgctggcga gaaagtgacc      120
atctcctgcc tgtcctccca gtccctgttc tcctccaaca ccaaccggaa ctacctgaac      180
tggtatctgc agaagcccgg ccagtcccct aagctgctga tctaccacgc ctccaccaga      240
ctgaccggcg tgcccgatag attcatcggc tctggctccg gcaccgactt tacctgacc      300
atcagctccg tgcaggccga ggacctgggc gactactact gccagcacca ctacgagaca      360
cccctgacct ttggcgacgg caccaagctg gaaatcaagc ggaccgtggc cgctccctcc      420
gtgttcatct cccaccttc cgacgagcag ctgaagtctg gcaccgcctc tgtcgtgtgc      480
ctgctgaaca acttctaccc ccgcgaggcc aaggtgcagt ggaaggtgga caacgccctg      540
cagtccggca actcccagga atccgtgacc gagcaggact ccaaggacag cacctactcc      600
ctgtccagca ccctgaccct gtccaaggcc gactacgaga gcacaaggt gtacgcctgc      660
gaagtgaccc accagggcct gtctagcccc gtgaccaagt ctttcaaccg gggcgagtgc      720
tgatga                                                                726
```